United States Patent
Bradley et al.

(10) Patent No.: US 12,157,893 B2
(45) Date of Patent: Dec. 3, 2024

(54) METHODS TO IMPROVE SITE-DIRECTED INTEGRATION FREQUENCY

(71) Applicant: MONSANTO TECHNOLOGY LLC, St. Louis, MO (US)

(72) Inventors: John Bradley, St. Louis, MO (US); Larry A. Gilbertson, St. Louis, MO (US); Ervin Nagy, Lake Saint Louis, MO (US); Christine Shyu, St. Louis, MO (US); Peizhen Yang, St. Louis, MO (US); Xudong Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 374 days.

(21) Appl. No.: 17/523,755

(22) Filed: Nov. 10, 2021

(65) Prior Publication Data

US 2022/0162625 A1    May 26, 2022

Related U.S. Application Data

(60) Provisional application No. 63/112,438, filed on Nov. 11, 2020.

(51) Int. Cl.
*C12N 15/82* (2006.01)

(52) U.S. Cl.
CPC ............... *C12N 15/8213* (2013.01)

(58) Field of Classification Search
None
See application file for complete search history.

(56) References Cited

U.S. PATENT DOCUMENTS

| | | | |
|---|---|---|---|
| 5,106,739 A | 4/1992 | Comai et al. | |
| 5,159,135 A | 10/1992 | Umbeck | |
| 5,188,958 A | 2/1993 | Moloney et al. | |
| 5,322,938 A | 6/1994 | McPherson et al. | |
| 5,352,605 A | 10/1994 | Fraley et al. | |
| 5,359,142 A | 10/1994 | McPherson et al. | |
| 5,378,619 A | 1/1995 | Rogers | |
| 5,463,174 A | 10/1995 | Moloney et al. | |
| 5,530,196 A | 6/1996 | Fraley et al. | |
| 5,591,616 A | 1/1997 | Hiei et al. | |
| 5,641,876 A | 6/1997 | McElroy et al. | |
| 5,731,179 A | 3/1998 | Komari et al. | |
| 5,750,871 A | 5/1998 | Moloney et al. | |
| 5,824,877 A | 10/1998 | Hinchee et al. | |
| 5,837,848 A | 11/1998 | Ely et al. | |
| 5,850,019 A | 12/1998 | Maiti et al. | |
| 6,051,753 A | 4/2000 | Comari et al. | |
| 6,140,078 A | 10/2000 | Sanders et al. | |
| 6,175,060 B1 | 1/2001 | Lefebvre et al. | |
| 6,177,611 B1 | 1/2001 | Rice | |
| 6,194,636 B1 | 2/2001 | McElroy et al. | |
| 6,232,526 B1 | 5/2001 | McElroy et al. | |
| 6,252,138 B1 | 6/2001 | Karimi et al. | |
| 6,265,638 B1 | 7/2001 | Bidney et al. | |
| 6,294,714 B1 | 9/2001 | Matsunaga et al. | |
| 6,384,301 B1 | 5/2002 | Martinell et al. | |
| 6,426,446 B1 | 7/2002 | McElroy et al. | |
| 6,429,357 B1 | 8/2002 | McElroy et al. | |
| 6,429,362 B1 | 8/2002 | Crane | |
| 6,433,252 B1 | 8/2002 | Kriz et al. | |
| 6,437,217 B1 | 8/2002 | McElroy et al. | |
| 6,635,806 B1 | 10/2003 | Kriz et al. | |
| 7,575,917 B2 | 8/2009 | Gilbertson et al. | |
| 9,062,316 B2 * | 6/2015 | Flasinski | C12N 15/113 |
| 2003/0110532 A1 | 6/2003 | Armstrong et al. | |
| 2004/0216189 A1 | 10/2004 | Houmard et al. | |
| 2005/0183170 A1 | 8/2005 | Fillatti et al. | |
| 2007/0271627 A1 | 11/2007 | Ye et al. | |
| 2019/0169640 A1 | 6/2019 | Gregory et al. | |
| 2019/0211344 A1 | 7/2019 | Krieger et al. | |
| 2019/0276842 A1 | 9/2019 | Doudna et al. | |
| 2020/0032289 A1 | 1/2020 | Anderson et al. | |
| 2020/0224160 A1 | 7/2020 | Ding et al. | |
| 2020/0270632 A1 | 8/2020 | Roy et al. | |

FOREIGN PATENT DOCUMENTS

| | | | | |
|---|---|---|---|---|
| WO | WO-2016007948 A1 * | 1/2016 | ............... | A01H 1/02 |
| WO | WO 2019/084148 A1 | 5/2019 | | |
| WO | WO 2021/026165 A1 | 2/2021 | | |

OTHER PUBLICATIONS

Lee K, Eggenberger AL, Banakar R, McCaw ME, Zhu H, Main M, Kang M, Gelvin SB, Wang K. CRISPR/Cas9-mediated targeted T-DNA integration in rice. Plant Mol Biol. Mar. 2019;99(4-5):317-328. doi: 10.1007/s11103-018-00819-1. Epub Jan. 15, 2019. PMID: 30645710. (Year: 2019).*

Albert et al., "Site-specific integration of DNA into wild-type and mutant loX sites placed in the plant genome," *The Plant Journal*, 7(4): 649-659 (1995).

Altschul et al., "Basic local alignment search tool." Journal of Molecular Biology, 215(3): 403-410 (1990).

Aronson et al., "In planta protein-protein interactions assessed using a nanovirus-based replication and expression system," *The Plant Journal*, 31(6): 767-775 (2002).

Baltes et al., "DNA Replicons for Plant Genome Engineering," *The Plant Cell*, 26(1): 151-163 (2014).

Beurdeley et al., "Compact designer TALENs for efficient genome engineering," *Nature Communications*, 4: 1762 (2013).

Bevan et al., "A chimaeric antibiotic resistance gene as a selectable marker for plant cell transformation," *Nature*, 304: 184-187 (1983).

(Continued)

*Primary Examiner* — Allison M Fox
*Assistant Examiner* — Qinhua Gu
(74) *Attorney, Agent, or Firm* — Arnold & Porter Kaye Scholer LLP

(57) ABSTRACT

The present disclosure relates to compositions and methods for improving site-directed integration frequency in the genome of plant cells.

20 Claims, 28 Drawing Sheets

Specification includes a Sequence Listing.

(56) References Cited

OTHER PUBLICATIONS

Campbell et al., "Codon Usage in Higher Plants, Green Algae, and Cyanobacteria," *Plant Physiology*, 92(1): 1-11 (1990).
Cermak et al., "Efficient design and assembly of custom TALEN and other TAL effector-based constructs for DNA targeting," *Nucleic Acids Research*, 39(12): e82 (2011).
Chandler et al., "Two regulatory genes of the maize anthocyanin pathway are homologous: isolation of B utilizing R genomic sequences," *Plant Cell*, 1(12): 1175-1183 (1989).
Chenna et al., "Multiple sequence alignment with the Clustal series of programs," *Nucleic Acids Research*, 31: 3497-3500 (2003).
Depicker et al., "Nopaline synthase: transcript mapping and DNA sequence," *Journal of Molecular and Applied Genetics*, 1(6): 561-73 (1982).
Doyle et al., "TAL Effector-Nucleotide Targeter (TALE-NT) 2.0: tools for TAL effector design and target prediction," *Nucleic Acids Research*, 40(W1): W117-122 (2012).
Ebert et al., "Identification of an essential upstream element in the nopaline synthase promoter by stable and transient assays," *Proc. Nat'l. Acad. Sci. USA*, 84: 5745-5749 (1987).
Fairhead et al., "New Vectors for Combinatorial Deletions in Yeast Chromosomes and for Gap-repair Cloning using 'Split-marker' Recombination," Yeast Functional Analysis Reports, 12:1439-1457 (1996)).
Freshney, "Animal Cell Culture: A Practical Approach," John Wiley & Sons, Inc, Hoboken, NJ (1986).
Fu et al., "Split marker transformation increases homologous integration frequency in Cryptococcus neoforrnans," Fungal Genetics and Biology, 43:200-212 (2006).
Gabsalilow et al., "Site- and strand-specific nicking of DNA by fusion proteins derived from MutH and I-SceI or TALE repeats," *Nucleic Acids Research*, 41(7): e83 (2013).
GE Healthcare Life Sciences, "18-1142-75 Recombinant Protein Purification: Principles and Methods Handbook" (2011).
GenBank Accession AC235177.1, "Glycine max strain Williams 82 clone GM_WBb0007H11, complete sequence," NCBI, (Mar. 2009).
GenBank Accession V00087, "*Agrobacterium tumefaciens* gene encoding nopaline synthetase. (Resident in plasmid pTiT37)," NCBI, (Mar. 1996).
Harlow et al., "Antibodies, a Laboratory Manual" Cold Spring Harbor Laboratory, Cold Spring Harbor, NY (1988).
International Search Report and Written Opinion dated Apr. 11, 2022, issued in International Application No. PCT/US2021/058839.
Koukolíková-Nicola et al., "Involvement of circular intermediates in the transfer of T-DNA from Agrobacterium tumefaciens to plant cells," *Nature*, 313: 191-196 (1985).
Larkin MA et al., "Clustal W and Clustal X version 2.0," Bioinformatics 23: 2947-48 (2007).

Lawton et al., "Expression of a soybean β-conclycinin gene under the control of the Cauliflower Mosaic Virus 35S and 19S promoters in transformed petunia tissues," *Plant Molecular Biology*, 9: 315-324 (1987).
Liu et al., "CasX enzymes comprise a distinct family of RNA-guided genome editors," *Nature*, 566(7743): 28-223 (2019).
Murray et al., "Codon usage in plant genes," *Nucleic Acids Research*, 17(2): 477-498 (1989).
Nakamura et al., "Codon usage tabulated from international DNA sequence databases," *Nucleic Acids Research*, 28(1): 292 (2000).
Odell et al., "Identification of DNA sequences required for activity of the cauliflower mosaic virus 35S promoter," *Nature*, 313: 810-812 (1985).
Schramm et al., "Recruitment of RNA polymerase III to its target promoters," *Genes & Development*, 16: 2593-2620 (2002).
Singer et al., "Formation of Complex Extrachromosomal T-DNA Structures in Agrobacterium tumefaciens-Infected Plants," *Plant Physiology*, 160(1): 511-522 (2012).
Smith et al., "Comparisons of Biosequences," *Advances in Applied Mathematics*, 2:482-489 (1981).
Thompson et al., "Clustal W: Improving the sensitivity of progressive multiple sequence alignment through sequence weighting, position-specific gap penalties and weight matrix choice," *Nucleic Acids Research*, 22(22): 4673-4680 (1994).
Toro et al., "Role of the overdrive sequence in T-DNA border cleavage in Agrobacterium," *PNAS*, 85(22): 8558-8562(1988).
Yang et al., "Maize sucrose synthase-I promoter directs phloem cell-specific expression of Gus gene in transgenic tobacco plants," *Proceedings of the National Academy of Sciences, USA*, 87(11): 4144-4148 (1990).
Yanik et al. "TALE-PvuII fusion proteins—novel tools for gene targeting," *PLoS One*, 8(12): e82539 (2013).
Ye et al., "Plant development inhibitory genes in binary vector backbone improve quality event efficiency in soybean transformation," *Transgenic Research*, 17(5): 827-838 (2008).
Zetsche et al., "Cpf1 Is a Single RNA-Guided Endonuclease of a Class 2 CRISPR-Cas System," *Cell*, 163(3):759-771 (2015).
Zhang et al., "PowerBLAST: a new network BLAST application for interactive or automated sequence analysis and annotation," Genome Research, 7(6) 649-656 (1997).
Jillette et al., Nat Commun. 10(1):4968. doi: 10.1038/s41467-019-12891-2, Split selectable markers, Oct. 31, 2019.
Lou et al., Mol Biotechnol. 60(5):380-385. doi: 10.1007/s12033-018-0080-9. Targeted Gene Deletion in Cordyceps militaris Using the Split-Marker Approach, May 2018.
You et al. Arch Microbiol.191(7):615-22. doi: 10.1007/s00203-009-0489-4. Gene-specific disruption in the filamentous fungus *Cercospora nicotianae* using a split-marker approach, Jul. 2009.

\* cited by examiner

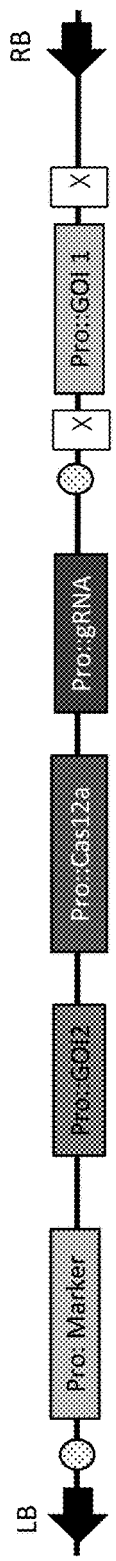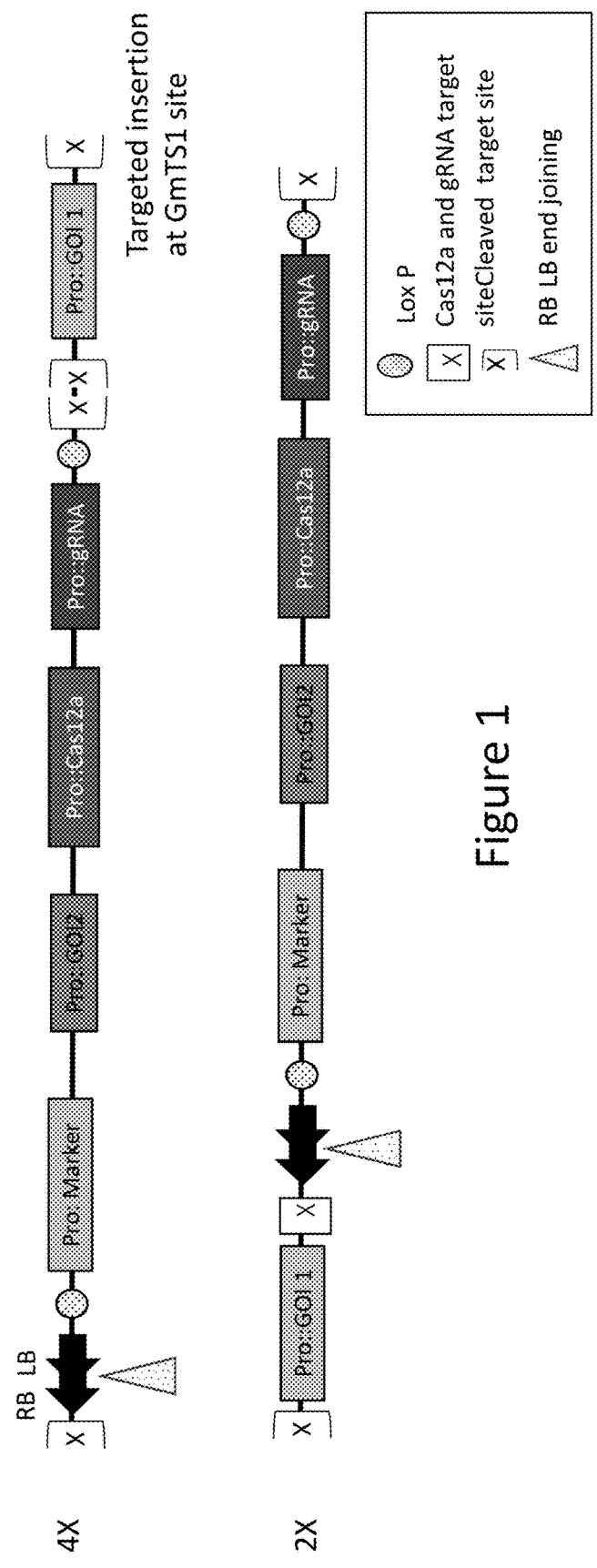
Figure 1

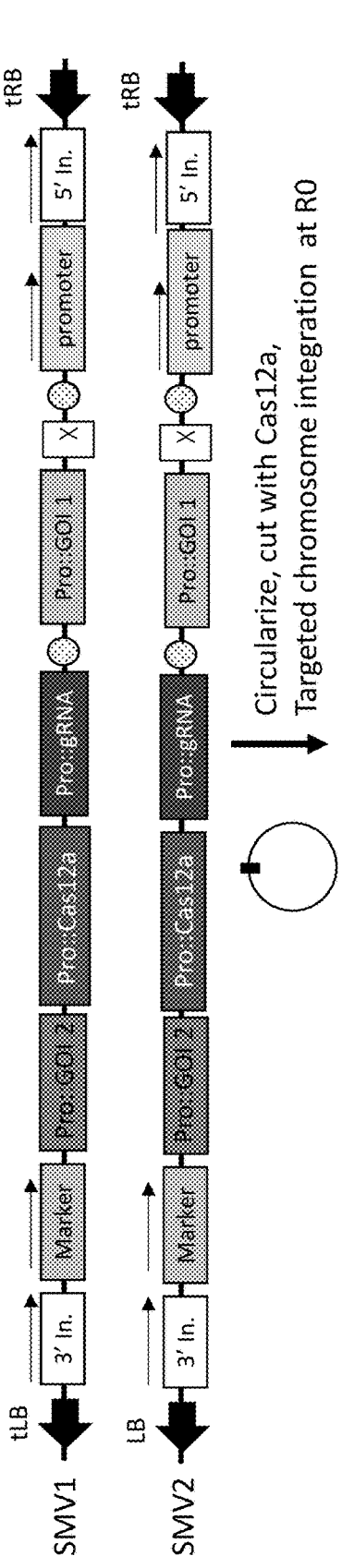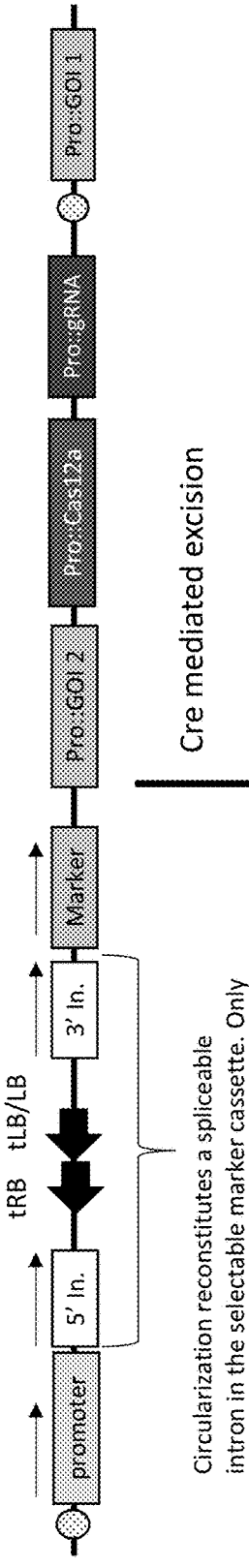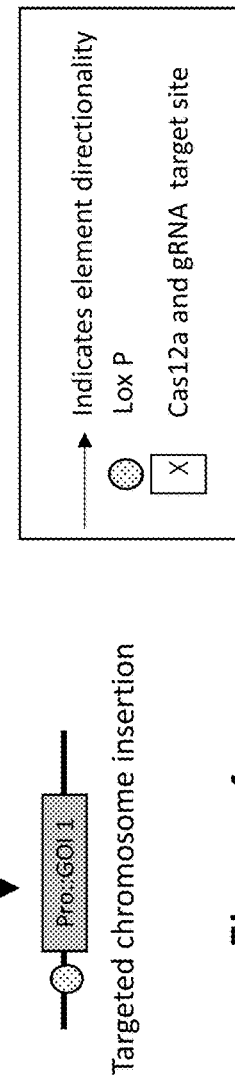
Figure 4

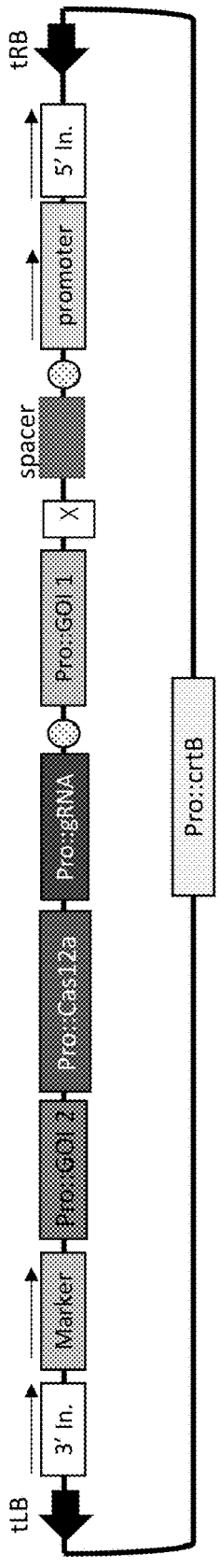
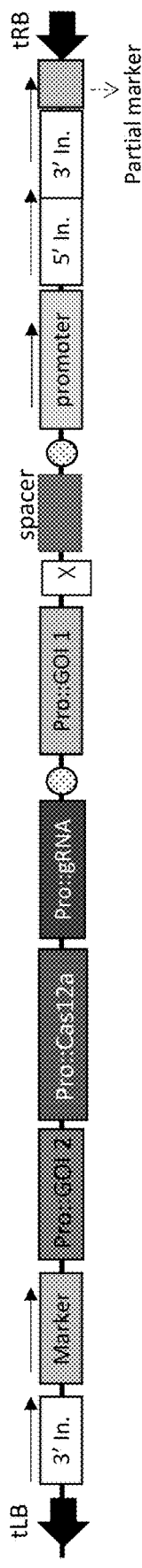
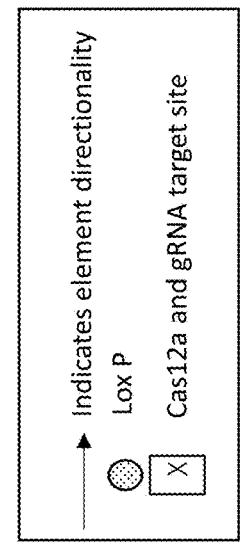
Figure 12A
Figure 12B
Figure 12

Initial Chromosomal DNA end:

SEQ ID NO: 37    5'   ......CATTAGACCATTGCC  3'
SEQ ID NO: 38    3'   ......GTAATCTGGTAACGG  5'

Initial Inserted DNA end:

SEQ ID NO: 39    3'   accttcgccattcgag......  3'
SEQ ID NO: 40    5'   tggaagcggtaagctc......  5'

A: Example linkage with no source ambiguity:

SEQ ID NO: 41    5'   ......CATTAGACCAgccattcgag......  3'
SEQ ID NO: 42    3'   ......GTAATCTGGTcggtaagctc......  5'

B: Example linkage with source ambiguity (microhomology):

SEQ ID NO: 43    5'   ......CATTAGACCATTcgag......  3'
SEQ ID NO: 44    3'   ......GTAATCTGGTAAgctc......  5'

Figure 14

A: Artifactual: blunt-end ligation creates appearance of microhomology

```
              5'  .....CATTAGACC        ATTcgag..... 3'
              3'  .....GTAATCTGG        TAAgctc..... 5'
                                  ⇩
SEQ ID NO: 41  5'  .....CATTAGACCATTcgag..... 3'
SEQ ID NO: 42  3'  .....GTAATCTGGTAAgctc..... 5'
```

B: Full microhomology: sticky-end ligation of overhanging single-stranded ends

```
                5'  .....CATTAGA              ccattcgag..... 3'
SEQ ID NO: 45   3'  .....GTAATCTGGTAA                gctc..... 5'
                                  ⇩
SEQ ID NO: 41   5'  .....CATTAGAccattcgag..... 3'
SEQ ID NO: 42   3'  .....GTAATCTGGTAAgctc..... 5'
```

C: Partial microhomology: sticky-end ligation of chewed-back single-stranded ends

```
                5'  .....CATTAGA              attcgag..... 3'
SEQ ID NO: 46   3'  .....GTAATCTGGT               gctc..... 5'
                                  ⇩
                5'  .....CATTAGA attcgag..... 3'
SEQ ID NO: 46   3'  .....GTAATCTGGT  gctc..... 5'
                                  ⇩
SEQ ID NO: 41   5'  .....CATTAGACCATTcgag..... 3'
SEQ ID NO: 42   3'  .....GTAATCTGGTAAgctc..... 5'
```

Figure 15

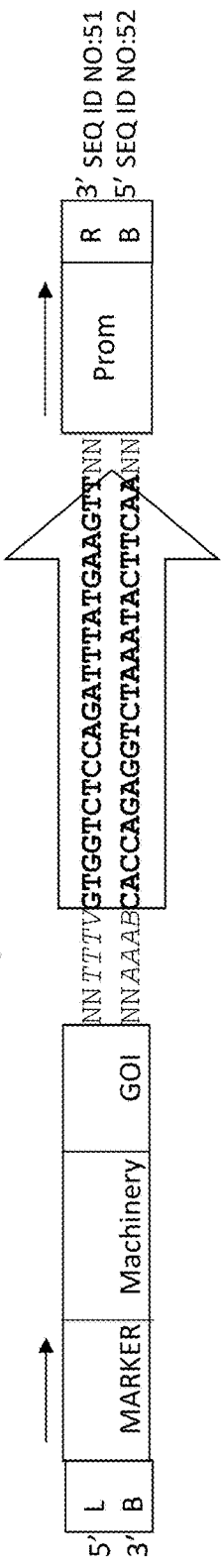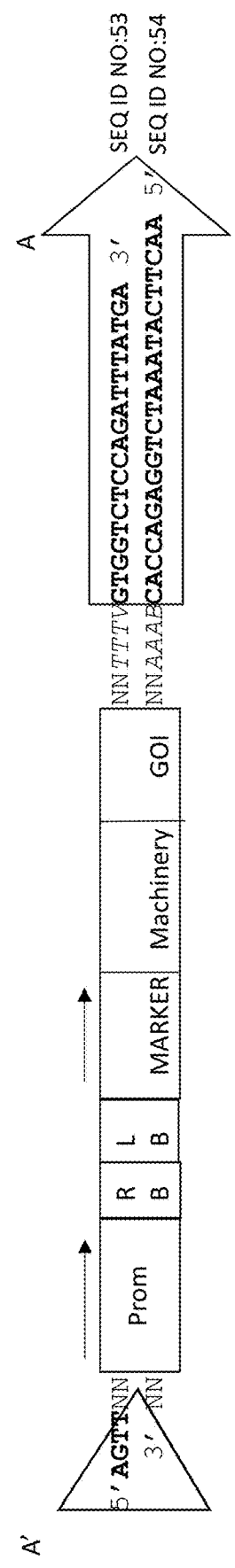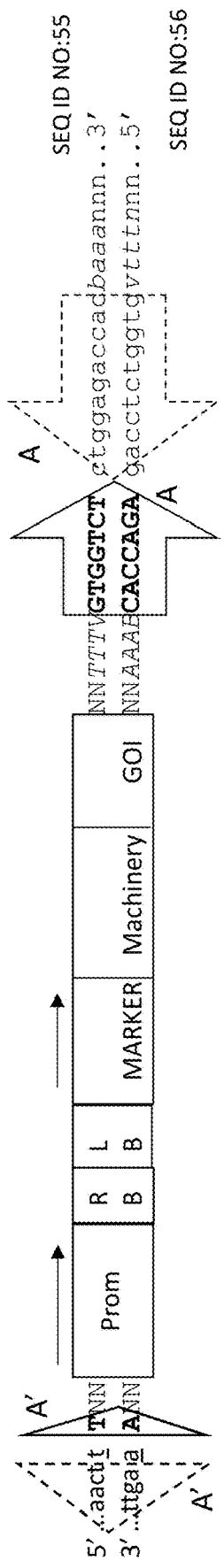
Figure 17

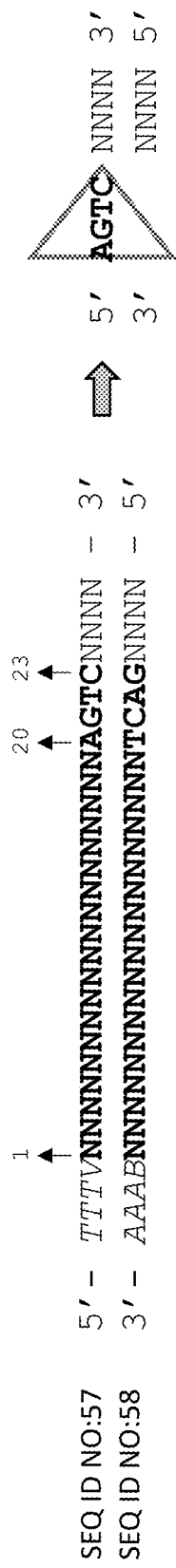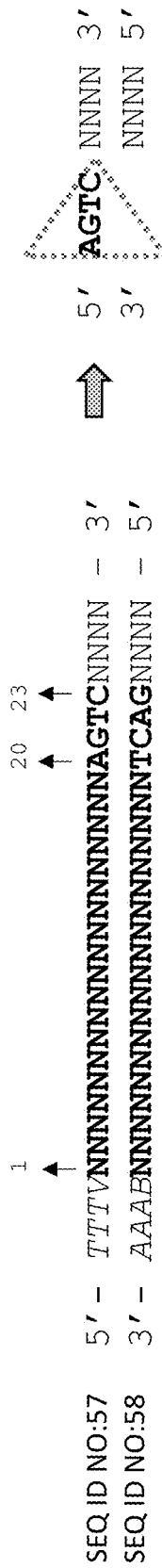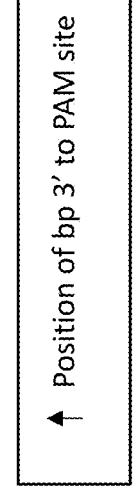
Figure 18A

GmTS1 Target site on chromosome and resulting A' product

```
                       1                         20  23
SEQ ID NO:57   5'-  TTTVNNNNNNNNNNNNNNNNNNNNAGTCNNNNN  -3'
SEQ ID NO:58   3'-  AAAABNNNNNNNNNNNNNNNNNNNNTCAGNNNNN -5'
```

⟹  5'  AGTC NNNNN  3'
   3'       NNNNN  5'

GmTS1_4RC Engineered Target site on T-DNA and resulting A' product

```
                       1                         20  23
SEQ ID NO:59   5'-  TTTVNNNNNNNNNNNNNNNNNNNNGACTNNNNN  -3'
SEQ ID NO:60   3'-  AAAABNNNNNNNNNNNNNNNNNNNNCTGANNNNN -5'
```

⟹  5'  GACT NNNNN  3'
   3'       NNNNN  5'

← Position of bp 3' to PAM site

Figure 18C

METHODS TO IMPROVE SITE-DIRECTED INTEGRATION FREQUENCY

CROSS-REFERENCE TO RELATED APPLICATION

This application claims the benefit of U.S. Provisional Application No. 63/112,438, filed Nov. 11, 2020, which is incorporated by reference in its entirety herein.

INCORPORATION OF SEQUENCE LISTING

A sequence listing contained in the file named "P34835US01_SL.TXT" which is 82,749 bytes (measured in MS-Windows®) and created on Nov. 10, 2021, is filed electronically herewith and incorporated by reference in its entirety.

FIELD

The present disclosure relates to compositions and methods for improving site-directed integration frequency using circular T-DNA.

BACKGROUND

Site-directed integration (SDI) frequency is very low in both soybean (*Glycine max*) and corn (*Zea mays*) transformation. Accordingly, transformation of either soybean or corn requires screening large numbers of primary transformants to identify SDI events. Methods that increase the absolute frequency of SDI, enrich for the regeneration of SDI events in primary transformants, or both, is highly desirable.

Transfer DNA (T-DNA) is transferred from the tumor-inducing (Ti) plasmid of *Agrobacterium* into a host plant's nuclear DNA genome. T-DNA is inserted into the genome of a plant cell by nicking the right border (RB) of the Ti plasmid, which creates a region of single stranded DNA from the T-DNA's left border (LB) to the RB. After the RB has been nicked, single-stranded DNA synthesis displaces the single-stranded DNA region, the LB is nicked, and the single-stranded T-DNA fragment can be incorporated into the plant cell's genome.

Successful *Agrobacterium*-mediated transformation of a plant cell typically results in a random integration in the plant genome. Such random integrations can have deleterious effects to the plant cell if the transgene inserts into an essential endogenous gene. Similarly, such random integrations can have a deleterious effect on expression of the transgene due to position effects of the chromosome where the transgene inserted. There exists a need in the art for improved SDI via *Agrobacterium*-mediated transformation of plant cells. A method for site-directed integration (SDI) that utilizes *Agrobacterium*-mediated transformation and relies on a nonhomologous end joining (NHEJ) strategy to integrate T-DNA into target sites that are cut by a guided nuclease has been used previously. However, this method produces an extremely low frequency (approximately 0.3%) of quality (e.g., single transgene, full length) SDI events in both corn and soybean.

Here, the inventors have developed novel methods and compositions to improve SDI in *Agrobacterium*-mediated transformation using circularized T-DNA.

BRIEF DESCRIPTION OF DRAWINGS

FIG. 1 comprises FIG. 1A and FIG. 1B. FIG. 1A depicts a schematic illustrating configuration of *Agrobacterium* T-DNA vector comprising expression cassettes for aadA marker, LbCas12a protein, LbCas12a guide RNA, and donor cassette for site directed integration of donor cassette into the GmTS1 target site. The donor cassette comprises an GOI-1 (Gene Of Interest-1) flanked by target sites (each depicted by an "X") recognized by the LbCas12a-gRNA complex. FIG. 1B depicts a schematic illustrating configuration of T-DNA integrations at GmTS1 site. LB and RB indicate the left border and right border sequences of the T-DNA. Pro indicates Promoter, GOI=Gene of Interest. Dotted arrowhead indicates RB-LB end joining.

FIG. 4 depicts a schematic illustrating a vector comprising RB and/or LB truncations, split marker cassette and a target site for a CRISPR nuclease.

FIG. 12 comprises FIG. 12A and FIG. 12B. FIGS. 12A and 12B depict schematic illustrating configuration of vectors to reduce backbone-containing events. Partial.Marker: a partial fragment of the 3' marker gene cassette.

FIG. 14 depicts initial DNA ends for a hypothetical chromosome and donor DNA that have a common 5 nucleotide element (bold text). The embodiments shown in A and B are blunt-ended, but staggered embodiments are contemplated (as in the case for LbCas12a-mediated integration). The initial ends can be subject to some amount of "fraying" or "chew back" from original cut sites prior to being joined together. The embodiment shown in 14A results in a linkage where every position is unambiguously attributable to chromosome (upper case) or donor (lower case) origin. The embodiment shown in 14B results in a linkage where a 5 bp region (upper case and in bold) has ambiguous origin (e.g., could be derived originally from either parent strand).

FIG. 15 depicts examples of microhomology potential pathways. 15A depicts blunt-end ligation of the ends can recreate a region of ambiguity ("artifactual microhomology"). 15B depicts annealing and ligation of "sticky-ends" ("full microhomology") where 5' or 3' protruding single stranded DNA regions anneal perfectly. 15C depicts a ligation of partially chewed back 5' or 3' single strand ends resulting in one or more base pairings at the ends of the strands, followed by presumptive fill-in of base-pairs and ligation to complete the insertion.

FIG. 17 depicts circularized, cleaved, and linearized T-DNA insertions. Circularized and LbCas12a cleaved T-DNAs insert overwhelmingly in the reverse orientation. Sequence in uppercase font depicts T-DNA. Sequence with lowercase font depicts chromosomal DNA sequence. Arrows with solid line in T-DNA (top panel) indicates Cas12a target site. T-DNA target sequence is shown in bold. Arrows with solid lines in $2^{nd}$ and $3^{rd}$ panel indicate cleaved T DNA target site. Arrows with dashed lines in $3^{rd}$ panel indicated cleaved target site on the chromosome. Circularized on-target insertions are predominantly in the reverse orientation, in which the direction of the remainder of the target region (solid arrows) in the T-DNA (upper case) are in the opposite orientation as the remainder of the target region (dashed arrows) in the chromosome (lower case) resulting in linkage between two slightly truncated A' regions on one end, and two slightly more truncated A regions on the other. Underlined base pair illustrates microhomology at A'/A' junction. The target sequence shown is for illustrative purposes only; drawings are not to scale.

FIG. 18A depicts an illustration of the GmTS1 target site and resulting A' cleavage products on the Chromosome and T-DNA. The PAM site is shown in italics; the 23-bp target site is in bold. Positions 1-19 of the target site are only associated with the A cleavage product, so for clarity are shown only as N. Arrowhead with solid lines: full-length A' overhang of chromosomal target GmTS1. Arrowhead with dashed lines: full length A' overhang of the T-DNA copy of GmTS1. FIG. 18C depicts an illustration of the GmTS1 target site on the Chromosome and an engineered target site (GmTS1_4RC) on the T-DNA, as well as the resulting A' cleavage product of each. The PAM site is shown in italics; the 23-bp target site is in bold. Positions 1-19 of the target site are only associated with the A cleavage product, so for clarity are shown only as N. Positions 20 to 23 within the GmTS1_4RC target site are the reverse complement (RC) of positions 20 to 23 in GmTS1.

SUMMARY

Figure 2:
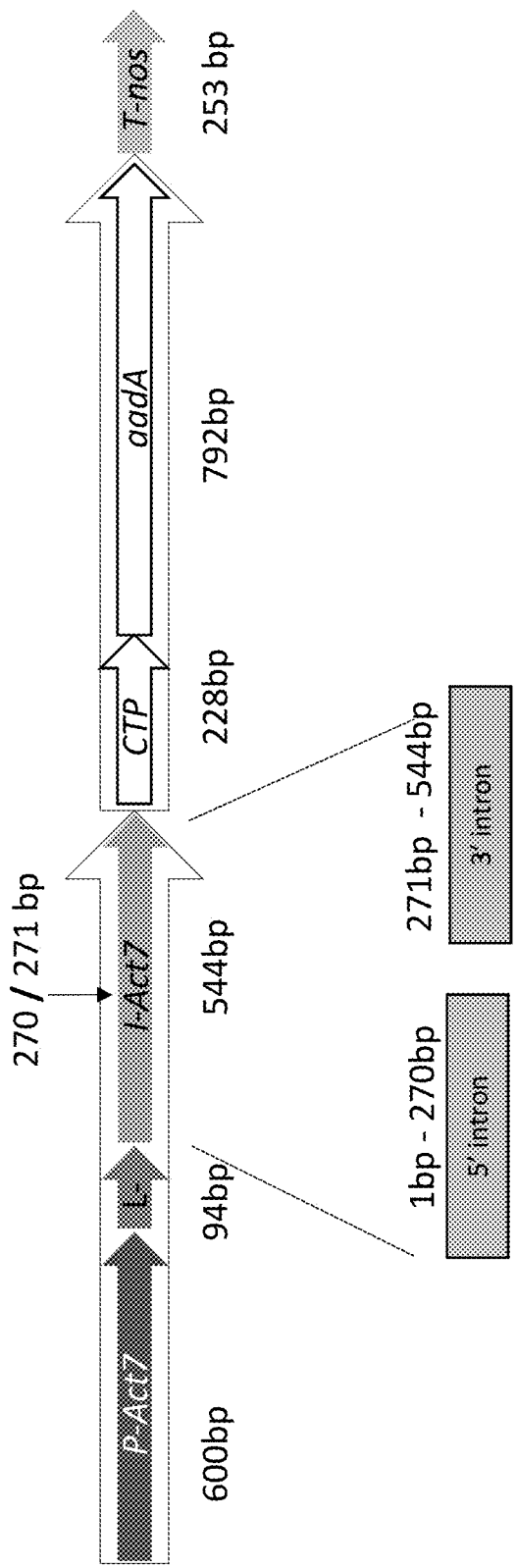
FIG. 2 depicts a schematic illustrating the aadA selection marker cassette. P indicates promoter. L indicates leader. I indicates Intron, CTP indicates Chloroplast transit peptide, T indicates terminator.

In one aspect, this disclosure provides a recombinant nucleic acid construct comprising: (a) a left border sequence; (b) a first recombination site and a second recombination site; (c) a target site for a guided nuclease; (d) a gene of interest operably linked to a first promoter; and (e) a right border sequence, where the target site for the guided nuclease and the sequence of interest operably linked to a first promoter are positioned between the first recombination site and the second recombination site.

In one aspect, this disclosure provides a recombinant nucleic acid construct comprising: (a) a left border sequence; (b) a first recombination site and a second recombination site; (c) a sequence of interest operably linked to a first promoter; (d) a target site for a guided nuclease; (e) a second promoter; and (f) a right border sequence, where the sequence of interest operably linked to a first promoter and the target site for a guided nuclease are positioned between the first recombination site and the second recombination site.

In one aspect, this disclosure provides a recombinant nucleic acid construct comprising: (a) a left border sequence; (b) a first promoter; (c) a first recombination site and a second recombination site; (d) a target site for the guided nuclease; (e) a sequence of interest operably linked to a second promoter; and (f) a right border sequence, where the target site for a guided nuclease and the sequence of interest operably linked to a second promoter are positioned between the first recombination site and the second recombination site.

In one aspect, this disclosure provides a recombinant nucleic acid construct comprising: (a) a first left border (LB) sequence; (b) a first recombination site and a second recombination site; (c) a sequence of interest operably linked to a first promoter; (d) a target site for a guided nuclease; (e) a first right border (RB) sequence; (f) a second RB sequence; and (g) a second LB sequence, where the sequence of interest operably linked to a first promoter and the target site for a guided nuclease are positioned between the first recombination site and the second recombination site.

In one aspect, this disclosure provides a recombinant nucleic acid construct comprising: (a) a left border sequence; (b) a sequence encoding a selectable marker gene; (c) a first recombination site and a second recombination site; (d) a target site for a guided nuclease; (e) a sequence of interest operably linked to a first promoter; (f) a second promoter; and (g) a right border sequence, where the second promoter and the selectable marker gene are in the same orientation, and where the target site for a guided nuclease and the sequence of interest operably linked to a first promoter are positioned between the first recombination site and the second recombination site.

In one aspect, this disclosure provides a recombinant nucleic acid construct comprising (a) a left border sequence; (b) at least one guide RNA operably linked to a first promoter; (c) a first recombination site and a second recombination site; (d) a target site for a guided nuclease; (e) a sequence of interest operably linked to a second promoter; and (f) a right border sequence, where the target site for a guided nuclease and the sequence encoding a sequence of interest operably linked to a second promoter are positioned between the first recombination site and the second recombination site.

In one aspect, this disclosure provides a method of editing a genome of a plant cell, the method comprising: (a) providing any recombinant nucleic acid construct provided herein to at least one plant cell; and (b) selecting at least one plant cell from step (a), where the at least one plant cell comprises the sequence of interest inserted into a genome of the plant cell.

In one aspect, this disclosure comprises a plant cell or a plant comprising any of the recombinant nucleic acid constructs provided herein.

In one aspect, this disclosure provides a method comprising introducing to a cell any recombinant DNA construct provided herein, where the guided nuclease cleaves the target site for a guided nuclease and a genomic target site, and where the sequence of interest is inserted into the genomic target site.

In one aspect, this disclosure provides an engineered double-stranded donor DNA molecule comprising one or more target sites for a guided nuclease adjacent to at least one sequence of interest, where the sequence of nucleotide positions 20 to 23 of the target strand within the one or more target sites for a guided nuclease are the reverse complement of the sequence of nucleotide positions 20 to 23 of the target strand within a genomic target site.

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of the compositions and methods described in this disclosure includes, unless otherwise indicated, conventional techniques of biochemistry, chemistry, molecular biology, microbiology, cell biology, plant biology, genomics, biotechnology, and genetics, which are within the skill of the art. See, for example, Green and Sambrook, Molecular Cloning: A Laboratory Manual, 4th edition (2012); Current Protocols In Molecular Biology (F. M. Ausubel, et al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

As used herein, terms in the singular and the singular forms "a," "an," and "the," for example, include plural referents unless the content clearly dictates otherwise.

Many methods can be used to transform plant cells. One popular method involves the use of *Agrobacterium tumefaciens*, which is capable of inserting a segment of transfer DNA (T-DNA) from a tumor-inducing (Ti) plasmid into a plant cell's genome. T-DNA is inserted into a genome of a plant cell by nicking the right border (RB) of the Ti plasmid, which creates a region of single stranded DNA from the T-DNA's left border (LB) to the RB (termed the "T-strand"). After the RB has been nicked, single-stranded DNA synthesis displaces the single-stranded DNA region, the LB is nicked, and the single-stranded T-DNA fragment can be incorporated into the plant cell's genome.

Despite the widespread use of *Agrobacterium*-mediated transformation, one major shortcoming is the inability to control where the T-DNA is inserted in the plant cell's genome. Here, Applicant has developed compositions for increasing targeted site-directed integrations of T-DNA into a genome of a plant cell using *Agrobacterium*-mediated transformation.

T-strands are known to circularize. See Koukolíková-Nicola et al., *Nature*, 313-191-196 (1985). The junction sequence of circular T-strand occurs precisely within the 25-nucleotide direct repeat normally found at the ends of the T-DNA region of the Ti plasmid, and evidence has shown that single-stranded T-DNA molecules are converted into double-stranded DNA (dsDNA) prior to integration. See Singer et al., *Plant Physiol.*, 160:511-522 (2012). Singer et al. proposed that circularized, double-stranded, T-DNA is a "dead end" product that are incapable of inserting into a genome of a plant.

Surprisingly, Applicant has discovered a mechanism to revive the "dead end" circularized, double-stranded T-DNA molecules and allow them to integrate into a genome of a plant.

In one aspect, this disclosure provides a recombinant nucleic acid construct comprising: (a) a left border (LB) sequence; (b) a first recombination site and a second recombination site; (c) a target site for a guided nuclease; (d) a sequence of interest operably linked to a first promoter; and (e) a right border (RB) sequence, where the target site for the guided nuclease and the sequence of interest operably linked to a first promoter are positioned between the first recombination site and the second recombination site. In an aspect, a recombinant nucleic acid construct further comprises a sequence encoding at least one selectable marker gene, where the sequence encoding the at least one selectable marker gene comprises (a) a second promoter; (b) at least one intron; and (c) a protein-coding sequence. In an aspect, the second promoter is positioned between the sequence of interest and the RB sequence, and the protein-coding sequence is positioned between the LB sequence and the sequence of interest. In an aspect, the LB sequence and the RB sequence are positioned between the second promoter and the protein-coding sequence. In an aspect, the recombinant nucleic acid construct is circularized, and the second promoter sequence and the RB sequence are positioned 5' to the LB sequence. In an aspect, the LB sequence and the RB sequence are both positioned 5' to the sequence of interest. In an aspect, the recombinant nucleic acid construct comprises the following components in 5' to 3' order: a second promoter, the first recombination site, the target site for the guided nuclease, the sequence of interest, the second recombination site, and the at least one selectable marker gene, where the second promoter and the at least one selectable marker gene are in the same orientation. In an aspect, the recombinant nucleic acid construct comprises the following components in 5' to 3' order: the first recombination site, the at least one selectable marker gene, the target site for the guided nuclease, the sequence of interest, a second promoter, and the second recombination site, where the second promoter and the at least one selectable marker gene are in the same orientation.

In one aspect, this disclosure provides a recombinant nucleic acid construct comprising: (a) a left border (LB) sequence; (b) a first recombination site and a second recombination site; (c) a sequence of interest operably linked to a first promoter; (d) a target site for a guided nuclease; (e) a second promoter; and (f) a right border (RB) sequence, where the sequence of interest operably linked to a first promoter and the target site for a guided nuclease are positioned between the first recombination site and the second recombination site. In an aspect, the recombinant nucleic acid construct further comprises a sequence encoding a guided nuclease, where the sequence encoding a guided nuclease comprises a first intron sequence and a second intron sequence. In an aspect, the recombinant nucleic acid construct comprises the LB sequence and the RB sequence positioned between the first intron sequence and the second intron sequence, where the first intron sequence and the second intron sequence are positioned between the second promoter and the sequence encoding a guided nuclease, and where the second promoter is operably linked to the sequence encoding a guided nuclease.

In one aspect, this disclosure provides a recombinant nucleic acid construct comprising: (a) a left border sequence; (b) a first promoter; (c) a first recombination site and a second recombination site; (d) a target site for the guided nuclease; (e) a sequence of interest operably linked to a second promoter; and (f) a right border sequence, where the target site for a guided nuclease and the sequence of interest operably linked to a second promoter are positioned between the first recombination site and the second recombination site. In an aspect, the recombinant nucleic acid construct further comprises at least one selectable marker gene operably linked to a third promoter. In an aspect, the recombinant nucleic acid construct further comprises a sequence encoding a recombinase. In an aspect, the recombinant nucleic acid construct further comprises a sequence encoding a guide RNA. In an aspect, the recombinant nucleic acid construct further comprises a sequence encoding a guided nuclease. In an aspect, the recombinant nucleic acid construct comprises the following components in 5' to 3' order: the first promoter, the first recombination site, the target site for the guided nuclease, the sequence of interest operably linked to a second promoter, the second recombination site, and the sequence encoding a guided nuclease, where the first promoter and the sequence encoding a guided nuclease are in the same orientation. In an aspect, the recombinant nucleic acid construct comprises the following components in 5' to 3' order: the first promoter, the first recombination site, the target site for the guided nuclease, the sequence of interest operably linked to a second promoter, the second recombination site, and the sequence encoding a gRNA, where the first promoter and the sequence encoding a gRNA are in the same orientation and where the sequence encoding a guided nuclease is operably linked to a third promoter. In an aspect, the recombinant nucleic acid construct comprises the following components in 5' to 3' order: a sequence encoding a guided nuclease, the first recombination site, the selectable marker gene, the target site for the guided nuclease, the sequence of interest operably linked to a second promoter, the first promoter, the second recombination site, and the third promoter, where the sequence encoding a guided nuclease and the third promoter are in the same orientation, and where the selectable marker gene and the first promoter are in the opposite orientation of the sequence encoding a guided nuclease and the third promoter.

In one aspect, this disclosure provides a recombinant nucleic acid construct comprising: (a) a first left border (LB) sequence; (b) a first recombination site and a second recombination site; (c) a sequence of interest operably linked to a first promoter; (d) a target site for a guided nuclease; (e) a first right border (RB) sequence; (f) a second RB sequence; and (g) a second LB sequence, where the sequence of interest operably linked to a first promoter and the target site for a guided nuclease are positioned between the first recombination site and the second recombination site. In an aspect, the recombinant nucleic acid construct further comprises (h) a sequence encoding a guide RNA operably linked to a second promoter. In an aspect, the recombinant nucleic acid construct further comprises (h) a sequence encoding at least one selectable marker gene operably linked to a second promoter. In an aspect, the recombinant nucleic acid construct further comprises (h) a sequence encoding a guided nuclease operably linked to a second promoter. In an aspect, the recombinant nucleic acid construct comprises the sequence of interest positioned between the first LB sequence and the first RB sequence. In an aspect, the recombinant nucleic acid construct comprises components (a), (b), (c), (d), (e), (f), and (g) physically linked in one nucleic acid vector. In an aspect, the recombinant nucleic acid construct comprises components (a), (b), (c), (d), (e), (f), (g), and a sequence encoding a guide RNA operably linked to a second promoter physically linked in one nucleic acid vector. In an aspect, the recombinant nucleic acid construct comprises components (a), (b), (c), (d), (e), (f), (g), and a sequence encoding at least one selectable marker gene operably linked to a second promoter physically linked in one nucleic acid vector. In an aspect, the recombinant nucleic acid construct comprises components (a), (b), (c), (d), (e), (f), (g), and a sequence encoding a guided nuclease operably linked to a second promoter physically linked in one nucleic acid vector. In an aspect, components (a), (b), (c), and (d) of the recombinant nucleic acid construct are physically linked in a first nucleic acid vector, and wherein components (e), (f), and (g) of the recombinant nucleic acid construct are physically linked in a second nucleic acid vector. In an aspect, components (a), (b), (c), and (d) of the recombinant nucleic acid construct are physically linked in a first nucleic acid vector, and wherein components (e), (f), (g), and a sequence encoding a guide RNA operably linked to a second promoter of the recombinant nucleic acid construct are physically linked in a second nucleic acid vector. In an aspect, components (a), (b), (c), and (d) of the recombinant nucleic acid construct are physically linked in a first nucleic acid vector, and wherein components (e), (f), (g), and a sequence encoding at least one selectable marker gene operably linked to a second promoter of the recombinant nucleic acid construct are physically linked in a second nucleic acid vector. In an aspect, components (a), (b), (c), and (d) of the recombinant nucleic acid construct are physically linked in a first nucleic acid vector, and wherein components (e), (f), (g), and a sequence encoding a guided nuclease operably linked to a second promoter of the recombinant nucleic acid construct are physically linked in a second nucleic acid vector.

In one aspect, this disclosure provides a recombinant nucleic acid construct comprising: (a) a left border sequence; (b) a sequence encoding a selectable marker gene; (c) a first recombination site and a second recombination site; (d) a target site for a guided nuclease; (e) a sequence of interest operably linked to a first promoter; (f) a second promoter; and (g) a right border sequence, where the second promoter and the selectable marker gene are in the same orientation, and where the target site for a guided nuclease and the sequence of interest operably linked to a first promoter are positioned between the first recombination site and the second recombination site.

In one aspect, this disclosure provides a recombinant nucleic acid construct comprising (a) a left border sequence; (b) at least one guide RNA operably linked to a first promoter; (c) a first recombination site and a second recombination site; (d) a target site for a guided nuclease; (e) a sequence of interest operably linked to a second promoter; and (f) a right border sequence, where the target site for a guided nuclease and the sequence encoding a sequence of interest operably linked to a second promoter are positioned between the first recombination site and the second recombination site.

In one aspect, this disclosure provides a method of editing a genome of a plant cell, the method comprising: (a) providing any recombinant nucleic acid construct provided herein to at least one plant cell; and (b) selecting at least one plant cell from step (a), where the at least one plant cell comprises the sequence of interest inserted into a genome of the plant cell. In an aspect, the method further comprises (c) regenerating a plant from the at least one plant cell selected in step (b).

In one aspect, this disclosure comprises a plant cell or a plant comprising any of the recombinant nucleic acid constructs provided herein.

As used herein, the term "recombinant" in reference to a nucleic acid (DNA or RNA) molecule, protein, construct, vector, etc., refers to a nucleic acid or amino acid molecule or sequence that is man-made and not normally found in nature, and/or is present in a context in which it is not normally found in nature, including a nucleic acid molecule (DNA or RNA) molecule, protein, construct, etc., comprising a combination of polynucleotide or protein sequences that would not naturally occur contiguously or in close proximity together without human intervention, and/or a polynucleotide molecule, protein, construct, etc., comprising at least two polynucleotide or protein sequences that are heterologous with respect to each other.

In one aspect, methods and compositions provided herein comprise a vector. As used herein, the term "vector" refers to a DNA molecule used as a vehicle to carry exogenous genetic material into a cell. In an aspect, a recombinant nucleic acid construct is provided in one vector. In an aspect, a recombinant nucleic acid construct is provided in two or more vectors.

In an aspect, one or more polynucleotide sequences from a recombinant nucleic acid construct are stably integrated into a genome of a plant. In an aspect, one or more polynucleotide sequences from a vector are stably integrated into a genome of a plant.

In an aspect, a first nucleic acid sequence and a second nucleic acid sequence are provided in a single vector. In an aspect, a first nucleic acid sequence is provided in a first vector, and a second nucleic acid sequence is provided in a second vector.

As used herein, the term "T-strand" refers to a single-strand copy of DNA made when transcription is initiated from a right border (RB) DNA sequence of a vector. In a naturally occurring Ti plasmid, synthesis of the transfer DNA (T-DNA) is initiated at a 25-base-pair consensus DNA sequence referred to as the "right border" (RB), and T-strand synthesis termination occurs at a 25 bp consensus DNA sequence referred to as the "left border" (LB). Typically, a RB sequence or a LB sequence comprises the respective 25 bp consensus DNA sequence as well as flanking DNA sequence on the 3' end, the 5' end, or both. As used herein, a "RB" or a "LB" sequence refers to the respective 25 bp consensus DNA sequence as well as flanking DNA sequence. In an aspect, a LB sequence is a truncated border sequence. In an aspect, a RB sequence is a truncated border sequence. In an aspect, a RB DNA sequence or a LB DNA sequence provided herein can be of any length such that the DNA segment is capable of transformation of plant tissue performed by *Agrobacterium* or other Rhizobiales-mediated methods (See U.S. Pat. Nos. 5,731,179 and 6,265,638; and U.S. Patent Application Publications US2003/110532; US2005/0183170; US2007/0271627; and US2019/0211344). In an aspect, a RB DNA sequence or a LB DNA sequence comprises at least 25 nucleotides. In an aspect, a RB DNA sequence or a LB DNA sequence comprises at least 50 nucleotides. In an aspect, a RB DNA sequence or a LB DNA sequence comprises at least 100 nucleotides. In an aspect, a RB DNA sequence or a LB DNA sequence comprises at least 200 nucleotides. In an aspect, a RB DNA sequence or a LB DNA sequence comprises at least 300 nucleotides. In an aspect, a RB DNA sequence or a LB DNA sequence comprises at least 400 nucleotides. In an aspect, a RB DNA sequence or a LB DNA sequence comprises at least 500 nucleotides. In an aspect, a RB DNA sequence or a LB DNA sequence comprises at least 600 nucleotides.

As used herein, a "truncated border sequence" refers to a border sequence that is shorter than a native border sequence and comprises a 25 bp consensus DNA sequence for either the RB DNA sequence or the LB DNA sequence. As a non-limiting example, if a native RB DNA sequence comprises 300 nucleotides, including the 25 bp consensus DNA sequence, a truncated RB DNA sequence could comprise equal to or less than 299 nucleotides, provided that the 25 bp consensus DNA sequence is still present. In an aspect, a "truncated LB sequence" refers to a DNA sequence that comprises the 25 bp consensus DNA sequence and fragment from the flanking sequence located 5' to the LB consensus sequence. In an aspect, a "truncated RB sequence" refers to a DNA sequence that comprises the 25 bp consensus DNA sequence and the conserved "overdrive" sequence (see Toro et al., PNAS; 85:8558-8562(1988)). In another aspect, a "truncated RB sequence" refers to a DNA sequence that comprises the 25 bp consensus DNA sequence, the conserved "overdrive" sequence, and fragment from the flanking sequence located 3' to the RB consensus sequence.

In an aspect, a recombinant nucleic acid construct comprises at least one LB sequence. In an aspect, a recombinant nucleic acid construct comprises at least two LB sequences. In an aspect, a recombinant nucleic acid construct comprises at least three LB sequences. In an aspect, a recombinant nucleic acid construct comprises at least one RB sequence. In an aspect, a recombinant nucleic acid construct comprises at least two RB sequences. In an aspect, a recombinant nucleic acid construct comprises at least three RB sequences.

Site-specific recombination occurs when DNA strand exchange takes place between DNA segments possessing at least some sequence homology with each other. Site-specific recombinases are able to recognize and bind to "recombination sites," which are short, specific DNA sequences which are cleaved by the recombinase, allowing the exchange of DNA strands, which is followed by strand repair. Typically, each recombinase protein binds to a specific, and unique, recombination site. As used herein, a "recombinase" refers to an enzyme that is capable of catalyzing site-specific recombination events within DNA. Recombinases are capable of excising DNA, inserting DNA, inverting DNA, translocating DNA, and/or exchanging DNA.

Several embodiments relate to a T-DNA vector comprising a sequence of interest for site directed integration positioned between recombination sites. In some embodiments, the sequence of interest comprises one or more target sites for a guided nuclease. In some embodiments, the T-DNA vector further comprises an expression cassette encoding a recombinase. In some embodiments, the T-DNA vector further comprises an expression cassette encoding a guided nuclease, wherein the expression cassette encoding the guided nuclease is disrupted by sequence of interest and recombination sites. In some embodiments, the T-DNA vector further comprises an expression cassette encoding a marker, wherein the expression cassette encoding the marker is disrupted by sequence of interest and recombination sites. In some embodiments, the T-DNA vector further comprises a split marker cassette.

In an aspect, a recombinase is a tyrosine recombinase. In an aspect, a tyrosine recombinase is selected from the group consisting of a Cre recombinase and a Flp recombinase. In an aspect, a recombinase is Cre recombinase. Cre-lox is a site-specific recombination system derived from the bacteriophage P1. Cre-lox can be used to insert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. In some embodiments, Cre recombinase protein binds to two lox sites on different nucleic acids and cleaves at the lox sites. The cleaved nucleic acids are spliced together (reciprocally translocated) and recombination is complete. In some embodiments, Cre recombinase protein binds to two lox sites flanking a sequence of interest and excises a circle from a T-DNA comprising the sequence of interest. In some embodiments the sequence of interest comprises a target site for a guided nuclease.

In several embodiments, a T-DNA vector as described herein comprises modified lox sites, for example, lox66 and lox71 sites, (see Albert et al., 1995, Plant J., 7, 649-659). Cre-mediated recombination between these modified lox sites results in one wild-type loxP site and one double mutant lox66-71 site, which displays a very low affinity for Cre recombinase and consequently, is unable to recombine with a loxP site.

In an aspect, a recombinase is Flippase (Flp). The Flp-FRT site-specific recombination system comes from the 2μ plasmid from the baker's yeast *Saccharomyces cerevisiae*. Flp is capable of inducing recombination between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites.

In an aspect, a recombinase is a serine recombinase. In an aspect, a serine recombinase is selected from the group consisting of a PhiC31 integrase, an R4 integrase, and a TP-901 integrase. In an aspect, a recombinase is PhiC31 integrase. In an aspect, a recombinase is R4 integrase. In an aspect, a recombinase is TP-901 integrase.

In an aspect, a recombinase is a Hin recombinase. In an aspect, a recombinase is Dre recombinase. In an aspect, a recombinase is KD recombinase. In an aspect, a recombinase is B2 recombinase. In an aspect, a recombinase is B3 recombinase. In an aspect, a recombinase is k integrase. In an aspect, a recombinase is HK022 integrase. In an aspect, a recombinase is HP1 integrase. In an aspect, a recombinase is Tn3 resolvase. In an aspect, a recombinase is Gin recombinase. In an aspect, a recombinase is ParA resolvase. In an aspect, a recombinase is γ6 resolvase. In an aspect, a recombinase is Bxbl integrase.

In an aspect, a recombinase is selected from the group consisting of Cre recombinase, a FLP recombinase, a Gin recombinase, a Tnpl recombinase, a Bxbl integrase, a phiC31 integrase, an R4 integrase, and a TP-901 integrase.

In an aspect, a recombinant nucleic acid construct comprises at least one recombination site. In an aspect, a recombinant nucleic acid construct comprises at least two recombination sites. In an aspect, a recombinant nucleic acid construct comprises at least three recombination sites. In an aspect, a recombinant nucleic acid construct comprises at least four recombination sites. In an aspect, a recombinant nucleic acid construct comprises at least five recombination sites. In an aspect, a recombinant nucleic acid construct comprises at least six recombination sites. When a recombinant nucleic acid construct comprises a sequence encoding two or more recombinases, the recombinases can be identical to each other, or they can be two or more different recombinases.

In an aspect, a recombination site comprises at least 10 nucleotides. In an aspect, a recombination site comprises at least 20 nucleotides. In an aspect, a recombination site comprises at least 30 nucleotides. In an aspect, a recombination site comprises at least 40 nucleotides. In an aspect, a recombination site comprises at least 50 nucleotides. In an aspect, a recombination site comprises at least 60 nucleotides. In an aspect, a recombination site comprises at least 70 nucleotides. In an aspect, a recombination site comprises at least 80 nucleotides. In an aspect, a recombination site comprises at least 90 nucleotides. In an aspect, a recombination site comprises at least 100 nucleotides. In an aspect, a recombination site comprises between 10 nucleotides and 200 nucleotides. In an aspect, a recombination site comprises between 10 nucleotides and 150 nucleotides. In an aspect, a recombination site comprises between 10 nucleotides and 100 nucleotides. In an aspect, a recombination site comprises between 10 nucleotides and 75 nucleotides. In an aspect, a recombination site comprises between 10 nucleotides and 50 nucleotides. In an aspect, a recombination site comprises between 25 nucleotides and 200 nucleotides. In an aspect, a recombination site comprises between 25 nucleotides and 150 nucleotides. In an aspect, a recombination site comprises between 25 nucleotides and 100 nucleotides. In an aspect, a recombination site comprises 34 nucleotides. In an aspect, a recombination site comprises 48 nucleotides.

In an aspect, a recombination site is a lox site. In an aspect, a lox site is selected from the group consisting of a loxP site, a lox 2272 site, a loxN site, a lox 511 site, a lox 5171 site, a lox71 site, a lox66 site, a loxLTR site, an M2 site, an M3 site, an M7 site, and an M11 site. In an aspect, a recombination site is an FRT site. In an aspect, a recombination site is an attP site. In an aspect, a recombination site is an attB site. In an aspect, a recombination site is a Hin binding site.

In an aspect, a recombinant nucleic acid construct comprises a first recombination site and a second recombination site. In an aspect, a first recombination site and a second recombination site are lox sites. In an aspect, a first recombination site and a second recombination site are FRT sites.

In an aspect, a first recombination site and a second recombination site are identical to each other. In an aspect, a first recombination site and a second recombination site comprise identical sequences. In an aspect, a first recombination site and a second recombination site comprise different sequences. In an aspect, the first recombination site and the second recombination sites are modified lox sites that can undergo only one round of Cre-mediated recombination resulting in the generation of one wild-type lox site and one double mutant site that are not compatible with each other (see Albert et al., 1995, Plant J., 7, 649-659). In an aspect the first recombination site is lox66 and the second recombination site is lox71.

In an aspect, a first recombination site and a second recombination site are compatible with each other. As used herein, in reference to a first recombination site and a second recombination site, "compatible" means that the same recombinase can act on both recombination sites and promote recombination between them.

As used herein, a "guided nuclease" refers to a nuclease that is capable of binding to, and cleaving at or near, a specific target site within a nucleic acid molecule (e.g., a target site for a guided nuclease).

As used herein in reference to being near a specific target site, "near" refers to within 250 nucleotides of the target site on either the 5'-end or the 3'-end of the target site.

In an aspect, this disclosure provides a guided nuclease. In an aspect, this disclosure provides at least one guided nuclease. In an aspect, this disclosure provides at least two guided nucleases. In an aspect, this disclosure provides a nucleic acid sequence encoding a guided nuclease. In an aspect, a nucleic acid sequence encoding a guided nuclease is operably linked to a promoter.

In an aspect, this disclosure provides a nucleic acid sequence encoding at least one guided nuclease. In an aspect, this disclosure provides a nucleic acid sequence encoding at least two guided nucleases. In an aspect, this disclosure provides a nucleic acid sequence encoding at least three guided nucleases.

In an aspect, a sequence encoding a guided nuclease comprises a first intron sequence and a second intron sequence.

A sequence that a guided nuclease binds to and/or cleaves, is referred to herein as a "target site for a guided nuclease" or simply a "target site." A target site positioned within a chromosome is referred to as a "genomic target site." For target sites cleaved by an RNA guided nuclease, the target site comprises a PAM sequence and a sequence recognized by the spacer sequence of a guide RNA. In an aspect, a target site for a guided nuclease is positioned in a recombinant nucleic acid construct. In an aspect, a target site for a guided nuclease is positioned 5' to a sequence of interest. In an aspect, a target site for a guided nuclease is positioned 3' to a sequence of interest. In an aspect, a recombinant nucleic acid construct provided herein comprises no more than one target site for a guided nuclease. In an aspect, a recombinant nucleic acid construct provided herein lacks a second target site for a guided nuclease. In an aspect, a target site for a guided nuclease is positioned between a first recombination site and a second recombination site.

In an aspect, a target site for a guided nuclease is present in a genome of a plant. In an aspect, a genome of a plant is a nuclear genome. In an aspect, a genome of a plant is a mitochondrial genome. In an aspect, a genome of a plant is a plastid genome. In an aspect, a genome of a plant is selected from the group consisting of a nuclear genome, a mitochondrial genome, and a plastid genome.

In an aspect, the same target site for a guided nuclease is present in a genome of a plant and a recombinant nucleic acid construct. In an aspect, a target site for a guided nuclease in a genome of a plant and a target site for a guided nuclease in a recombinant nucleic acid construct are identical. In an aspect, a target site for a guided nuclease in a genome of a plant and a target site for a guided nuclease in a recombinant nucleic acid construct are not identical.

In an aspect, a target site for a guided nuclease comprises 18 nucleotides. In an aspect, a target site for a guided nuclease comprises 19 nucleotides. In an aspect, a target site for a guided nuclease comprises 20 nucleotides. In an aspect, a target site for a guided nuclease comprises 21 nucleotides. In an aspect, a target site for a guided nuclease comprises 22 nucleotides. In an aspect, a target site for a guided nuclease comprises 23 nucleotides. In an aspect, a target site for a guided nuclease comprises 24 nucleotides. In an aspect, a target site for a guided nuclease comprises 25 nucleotides.

In an aspect, a target site for a guided nuclease comprises at least 10 nucleotides. In an aspect, a target site for a guided nuclease comprises at least 15 nucleotides. In an aspect, a target site for a guided nuclease comprises at least 20 nucleotides. In an aspect, a target site for a guided nuclease comprises at least 25 nucleotides. In an aspect, a target site for a guided nuclease comprises at least 30 nucleotides. In an aspect, a target site for a guided nuclease comprises at least 40 nucleotides. In an aspect, a target site for a guided nuclease comprises at least 50 nucleotides. In an aspect, a target site for a guided nuclease comprises at least 60 nucleotides. In an aspect, a target site for a guided nuclease comprises at least 70 nucleotides. In an aspect, a target site for a guided nuclease comprises at least 80 nucleotides. In an aspect, a target site for a guided nuclease comprises at least 90 nucleotides. In an aspect, a target site for a guided nuclease comprises at least 100 nucleotides. In an aspect, a target site for a guided nuclease comprises at least 150 nucleotides. In an aspect, a target site for a guided nuclease comprises at least 200 nucleotides.

In an aspect, a target site for a guided nuclease comprises between 10 nucleotides and 250 nucleotides. In an aspect, a target site for a guided nuclease comprises between 10 nucleotides and 200 nucleotides. In an aspect, a target site for a guided nuclease comprises between 10 nucleotides and 100 nucleotides. In an aspect, a target site for a guided nuclease comprises between 10 nucleotides and 75 nucleotides. In an aspect, a target site for a guided nuclease comprises between 10 nucleotides and 50 nucleotides. In an aspect, a target site for a guided nuclease comprises between 10 nucleotides and 30 nucleotides. In an aspect, a target site for a guided nuclease comprises between 10 nucleotides and 25 nucleotides. In an aspect, a target site for a guided nuclease comprises between 15 nucleotides and 30 nucleotides. In an aspect, a target site for a guided nuclease comprises between 15 nucleotides and 20 nucleotides.

In an aspect, a guided nuclease is selected from the group consisting of an RNA-guided nuclease, a zinc-finger nuclease (ZFN), a meganuclease, a transcription activator-like effector (TALE) nuclease (TALEN), and a TALE-like protein.

In an aspect, a guided nuclease is an RNA-guided nuclease. In an aspect, an RNA-guided nuclease is a CRISPR (Clustered Regularly Interspaced Short Palindromic Repeats) nuclease. CRISPR nucleases (e.g., Cas12a, Cas9, CasX) are proteins found in bacteria that are guided by guide RNAs ("gRNAs") to a target nucleic acid molecule, where the endonuclease can then cleave one or two strands the target nucleic acid molecule. Although the origins of CRISPR nucleases are bacterial, many CRISPR nucleases have been shown to function in eukaryotic cells.

While not being limited by any particular scientific theory, a CRISPR nuclease forms a complex with a guide RNA (gRNA), which hybridizes with a complementary target site, thereby guiding the CRISPR nuclease to the target site. In class II CRISPR-Cas systems, CRISPR arrays, including spacers, are transcribed during encounters with recognized invasive DNA and are processed into small interfering CRISPR RNAs (crRNAs). The crRNA comprises a repeat sequence and a spacer sequence which is complementary to a specific protospacer sequence in an invading pathogen. The spacer sequence can be designed to be complementary to target sequences in a eukaryotic genome.

CRISPR nucleases associate with their respective crRNAs in their active forms. CasX, similar to the class II endonuclease Cas9, requires another non-coding RNA component, referred to as a trans-activating crRNA (tracrRNA), to have functional activity. Nucleic acid molecules provided herein can combine a crRNA and a tracrRNA into one nucleic acid molecule in what is herein referred to as a "single guide RNA" (sgRNA). Cas12a does not require a tracrRNA to be guided to a target site; a crRNA alone is sufficient for Cas12a. The gRNA guides the active CRISPR nuclease complex to a target site, where the CRISPR nuclease can cleave the target site.

In an aspect, this disclosure provides at least one guide RNA. In an aspect, this disclosure provides at least two guide RNAs. In an aspect, this disclosure provides at least three guide RNAs. In an aspect, this disclosure provides a nucleic acid sequence encoding at least one guide RNA. In an aspect, a nucleic acid sequence encoding a guide RNA is operably linked to a promoter. In an aspect, a guide RNA is a single guide RNA. In an aspect, a guide RNA comprises a tracrRNA. In an aspect, a guide RNA comprises a crRNA.

In an aspect, this disclosure provides a first guide RNA and a second guide RNA. In an aspect, a first guide RNA and a second guide RNA are each operably linked to a promoter. In an aspect, a first guide RNA is operably linked to a first promoter, and a second guide RNA is operably linked to a second promoter. In an aspect, a first guide RNA and a second guide RNA are operably linked to the same promoter. In an aspect, a first guide RNA and a second guide RNA are operably linked to different promoters.

In an aspect, a guide RNA is capable of hybridizing with a target site for a guided nuclease, or to a nucleic acid sequence positioned within 50 nucleotides of the target site for the guided nuclease.

In an aspect, a guide RNA is capable of hybridizing with a target site for a guided nuclease. In an aspect, a guide RNA is capable of hybridizing with a target site for a guided nuclease in a recombinant DNA construct provided herein, but not in a plant genome. In an aspect, a guide RNA is capable of hybridizing with a target site for a guided nuclease in a plant genome, but not in a recombinant DNA construct provided herein. In an aspect, a guide RNA is capable of hybridizing with a first target site for a guided nuclease in a recombinant DNA construct and with a second target site for a guided nuclease in a genome of a plant, where the first and second target sites comprise identical sequences.

In an aspect, a guide RNA comprises at least 10 nucleotides. In an aspect, a guide RNA comprises at least 11 nucleotides. In an aspect, a guide RNA comprises at least 12 nucleotides. In an aspect, a guide RNA comprises at least 13 nucleotides. In an aspect, a guide RNA comprises at least 14 nucleotides. In an aspect, a guide RNA comprises at least 15 nucleotides. In an aspect, a guide RNA comprises at least 16 nucleotides. In an aspect, a guide RNA comprises at least 17 nucleotides. In an aspect, a guide RNA comprises at least 18 nucleotides. In an aspect, a guide RNA comprises at least 19 nucleotides. In an aspect, a guide RNA comprises at least 20 nucleotides. In an aspect, a guide RNA comprises at least 21 nucleotides. In an aspect, a guide RNA comprises at least 22 nucleotides. In an aspect, a guide RNA comprises at least 23 nucleotides. In an aspect, a guide RNA comprises at least 24 nucleotides. In an aspect, a guide RNA comprises at least 25 nucleotides. In an aspect, a guide RNA comprises at least 26 nucleotides. In an aspect, a guide RNA comprises at least 27 nucleotides. In an aspect, a guide RNA comprises at least 28 nucleotides. In an aspect, a guide RNA comprises at least 30 nucleotides. In an aspect, a guide RNA comprises at least 35 nucleotides. In an aspect, a guide RNA comprises at least 40 nucleotides. In an aspect, a guide RNA comprises at least 45 nucleotides. In an aspect, a guide RNA comprises at least 50 nucleotides. In an aspect, a guide RNA comprises at least 75 nucleotides. In an aspect, a guide RNA comprises at least 100 nucleotides. In an aspect, a guide RNA comprises at least 125 nucleotides.

In an aspect, a guide RNA comprises between 10 nucleotides and 150 nucleotides. In an aspect, a guide RNA comprises between 10 nucleotides and 125 nucleotides. In an aspect, a guide RNA comprises between 10 nucleotides and 100 nucleotides. In an aspect, a guide RNA comprises between 10 nucleotides and 75 nucleotides. In an aspect, a guide RNA comprises between 10 nucleotides and 50 nucleotides. In an aspect, a guide RNA comprises between 10 nucleotides and 40 nucleotides. In an aspect, a guide RNA comprises between 10 nucleotides and 30 nucleotides. In an aspect, a guide RNA comprises between 10 nucleotides and 20 nucleotides. In an aspect, a guide RNA comprises between 16 nucleotides and 28 nucleotides. In an aspect, a guide RNA comprises between 16 nucleotides and 25 nucleotides. In an aspect, a guide RNA comprises between 16 nucleotides and 20 nucleotides.

In an aspect, a target site for a guided nuclease is 100% complementary to a guide RNA. In an aspect, a target site for a guided nuclease is 99% complementary to a guide RNA. In an aspect, a target site for a guided nuclease is 98% complementary to a guide RNA. In an aspect, a target site for a guided nuclease is 97% complementary to a guide RNA. In an aspect, a target site for a guided nuclease is 96% complementary to a guide RNA. In an aspect, a target site for a guided nuclease is 95% complementary to a guide RNA. In an aspect, a target site for a guided nuclease is 94% complementary to a guide RNA. In an aspect, a target site for a guided nuclease is 93% complementary to a guide RNA. In an aspect, a target site for a guided nuclease is 92% complementary to a guide RNA. In an aspect, a target site for a guided nuclease is 91% complementary to a guide RNA. In an aspect, a target site for a guided nuclease is 90% complementary to a guide RNA. In an aspect, a target site for a guided nuclease is 85% complementary to a guide RNA. In an aspect, a target site for a guided nuclease is 80% complementary to a guide RNA. In an aspect, a target site for a guided nuclease is 75% complementary to a guide RNA. In an aspect, a target site for a guided nuclease is 70% complementary to a guide RNA.

When an RNA-guided CRISPR nuclease and a guide RNA form a complex, the whole system is called a "ribonucleoprotein." In an aspect, this disclosure provides a ribonucleoprotein.

A prerequisite for cleavage of the target site by a CRISPR ribonucleoprotein is the presence of a conserved Protospacer Adjacent Motif (PAM) near the target site. Depending on the CRISPR nuclease, cleavage can occur within a certain number of nucleotides (e.g., between 18-23 nucleotides for Cas12a) from the PAM site. PAM sites are only required for type I and type II CRISPR associated proteins, and different CRISPR endonucleases recognize different PAM sites. Without being limiting, Cas12a can recognize at least the following PAM sites: TTTN, and YTN; and CasX can recognize at least the following PAM sites: TTCN, TTCA, and TTC (where T is thymine; C is cytosine; A is adenine; Y is thymine or cytosine; and N is thymine, cytosine, guanine, or adenine). In an aspect, a target site for a guided nuclease comprises a PAM site.

In an aspect, a target site for a guided nuclease comprises at least one PAM site. In an aspect, a target site for a guided nuclease is adjacent to a nucleic acid sequence that comprises at least one PAM site. In an aspect, a target site for a guided nuclease is within 5 nucleotides of at least one PAM site. In a further aspect, a target site for a guided nuclease is within 10 nucleotides of at least one PAM site. In an aspect, a target site for a guided nuclease is within 15 nucleotides of at least one PAM site. In an aspect, a target site for a guided nuclease is within 20 nucleotides of at least one PAM site. In an aspect, a target site for a guided nuclease is within 25 nucleotides of at least one PAM site. In an aspect, a target site for a guided nuclease is within 30 nucleotides of at least one PAM site.

Cas12a (also referred to as Cpf1) is an RNA-guided nuclease of a class II, type V CRISPR/Cas system. Cas12a nucleases generate staggered cuts when cleaving a target nucleic acid molecule.

In an aspect, an RNA-guided nuclease is a Cas12a nuclease. In an aspect, a Cas12a nuclease is a *Lachnospiraceae bacterium* Cas12a (LbCas12a) nuclease. In an aspect, a Cas12a nuclease is an *Acidaminococcus* sp. Cas12a (AsCas12a) nuclease. In an aspect, a Cas12a nuclease provided herein is a *Francisella novicida* Cas12a (FnCas12a) nuclease. In an aspect, a Cas12a nuclease, or a nucleic acid encoding a Cas12a nuclease, is derived from a bacteria genus selected from the group consisting of *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opituaceae, Tuberibacillus, Bacillus, Brevibacilus, Methylobacterium, Acidaminococcus, Peregrinibacteria, Butyrivibrio, Parcubacteria, Smithella, Candidatus, Moraxella,* and *Leptospira*.

In an aspect, an RNA-guided nuclease is a Cas9 nuclease. In an aspect, an RNA-guided nuclease is a CasX nuclease. In an aspect, an RNA-guided nuclease is a CasY nuclease. In an aspect, an RNA-guided nuclease is selected from the group consisting of Cas12a, Cas9, CasX, CasY, C2c2, Cas1, Cas1B, Cas2, Cas3, Cas4, Cas5, Cas6, Cas7, Cas8, Cas10, Csy1, Csy2, Csy3, Cse1, Cse2, Csc1, Csc2, Csa5, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

It has been observed that following an integrative event, a junction between an original chromosome sequence and an integrated sequence includes one or more base pairs that are not unambiguously assignable as originating from the chromosome or the integrated sequence. It has been hypothesized that these short (generally, but not always, 6 base pairs or fewer) microhomologies may be involved in the efficiency of integration. See FIG. 14.

The ambiguity of sequence origin can occur via at least three mechanisms: (a) blunt-end ligation of the piece generate a region of ambiguity (e.g., artifactual microhomology); (b) annealing and ligation of "sticky ends," analogous to in vitro restriction enzyme-mediated subcloning, where 5' or 3' protruding single-stranded DNA regions anneal perfectly (e.g., full microhomology); and (c) ligation of partially chewed back 5' or 3' single-stranded ends resulting in one or more base pairings at the end of the strands, followed by presumptive fill-in of base pairs and ligation to complete the insertion (e.g., partial microhomology). See FIG. 15. See also Example 5.

Figure 16:
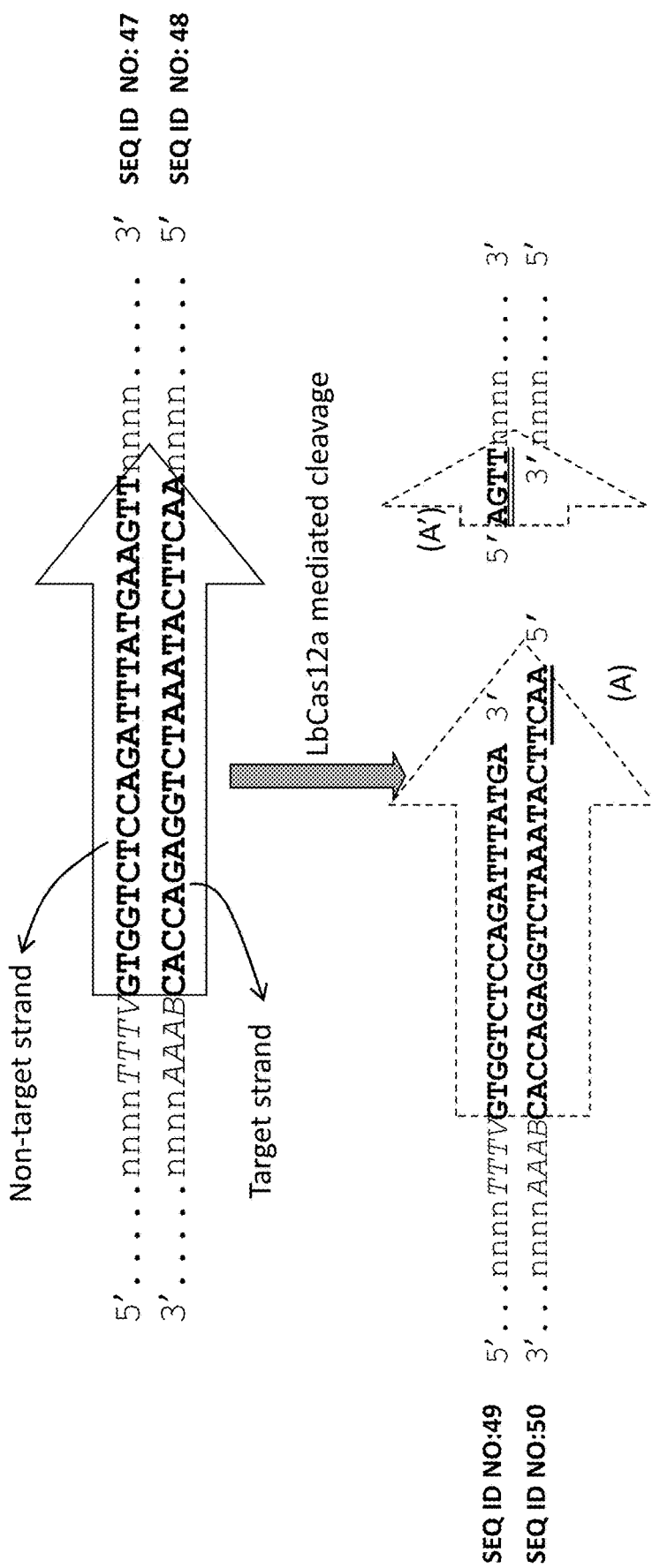
FIG. 16 depicts canonical LbCas12a-mediated DNA cleavage. Cas12a cuts at a 23-nt target region that is immediately preceded by a PAM site (italicized). When LbCas12a cuts, it cuts after position 19 on the top strand (also called the non-target strand) and after position 23 on the opposite strand (also called the target strand), generating a 4-nt 5' overhang on each strand. The arrow with a solid outline indicates a 23-mer target site on the DNA to be cleaved. Arrows with dashed outlines indicate a cleaved target site. The target sequence shown is for illustrative purpose only. Arrows are oriented in the direction starting from PAM sites shown in italics to end of 23-mer target region. The 4 nt 5' overhang on the target strand and 19nts of the target site is marked with a letter designation (here: "A"). The 4-nt 5' overhang on the non-target strand is marked A'. A' is the reverse complement of A, and can theoretically re-anneal perfectly to the A overhang. Single underlined nucleotides=A. Double underlined nucleotides=A'.

Enzymes like Cas12a and CasX have different cutting patterns when compared to Cas9. Cas9 cuts both strands at the same position, leaving a blunt end. Cas12a generates staggered cuts when cleaving a target nucleic acid molecule resulting in overhangs on each cleaved strand. Cas12a cuts at a 23-nt target region that is immediately preceded by a PAM site. When Cas12a cuts, it cuts after position 19 (counted from the PAM) on one strand (also called the non-target strand) and after position 23 on the opposite strand (also called the target strand), generating a 4-nt 5' overhang on each strand (See FIG. 16 and Zetsche et al., 2015, Cell, 163:759-771)). For target sites that comprise a PAM (e.g., target sites cleaved by an RNA-guided nuclease) nucleotide positions are counted from the PAM, with the first nucleotide after the PAM being considered position 1. For nucleases that cleave sites without a PAM, nucleotide positions are counted down from the cut site on the target strand from 5' to 3', with the nucleotide closest to the cut site considered to be position 23.

Note also that various versions of Cas12a variants may cut with different length overhangs—for instance some Cas12a variants are known to cleave after position 18 thus generating 5 bp overhangs (see Zetsche et al., 2015, Cell, 163:759-771). CasX also generates staggered ends on the target site. For example, DpbCasX generates products with ~10-nucleotide staggered ends due to cleavage 12-14 nucleotides after the PAM on the non-target strand and 22-25 nucleotides after the PAM on the target strand (see Liu et al., 2019, Nature, 566(7743): 28-223).

As used herein, a "target strand" refers to the DNA strand of a target site that is bound to by a guide RNA. A target strand is complementary to a "non-target strand," which is not bound by a guide RNA. Both a target strand and a non-target strand can be cleaved by an RNA-guided nuclease.

For the purposes of this disclosure, the 5' overhang on the target strand containing the PAM site is denoted "A". The 5' overhang on the non-target strand, that does not contain the PAM site is denoted A' (see FIG. 16). A' is the reverse complement of A, and can theoretically re-anneal perfectly to the A overhang. In an aspect A' comprises a 10-nucleotide overhang. In an aspect A' comprises a 9-nucleotide overhang. In an aspect A' comprises an 8-nucleotide overhang. In an aspect A' comprises a 7-nucleotide overhang. In an aspect A' comprises a 6-nucleotide overhang. In an aspect A' comprises a 5-nucleotide overhang. In an aspect A' comprises a 4-nucleotide overhang. In an aspect A' comprises a 3-nucleotide overhang. In an aspect A' comprises a 2-nucleotide overhang. In an aspect A' comprises a 1-nucleotide overhang.

In an aspect, a non-target strand comprises a 10 nucleotide overhang. In an aspect, a non-target strand comprises a 9 nucleotide overhang. In an aspect, a non-target strand comprises an 8 nucleotide overhang. In an aspect, a non-target strand comprises a 7 nucleotide overhang. In an aspect, a non-target strand comprises a 6 nucleotide overhang. In an aspect, a non-target strand comprises a 5 nucleotide overhang. In an aspect, a non-target strand comprises a 4 nucleotide overhang. In an aspect, a non-target strand comprises a 3-nucleotide overhang. In an aspect, a non-target strand comprises a 2 nucleotide overhang. In an aspect, a non-target strand comprises a 1 nucleotide overhang.

In an aspect, a target strand comprises a 10 nucleotide overhang. In an aspect, a target strand comprises a 9 nucleotide overhang. In an aspect, a target strand comprises an 8 nucleotide overhang. In an aspect, a target strand comprises a 7 nucleotide overhang. In an aspect, a target strand comprises a 6 nucleotide overhang. In an aspect, a target strand comprises a 5 nucleotide overhang. In an aspect, a target strand comprises a 4 nucleotide overhang. In an aspect, a target strand comprises a 3-nucleotide overhang.

In an aspect, a target strand comprises a 2 nucleotide overhang. In an aspect, a target strand comprises a 1 nucleotide overhang.

In an aspect, a target strand overhang comprises at least 1 nucleotide that is complementary to a genomic target site sequence. In an aspect, a target strand overhang comprises at least 2 nucleotides that are complementary to a genomic target site sequence. In an aspect, a target strand overhang comprises at least 3 nucleotides that are complementary to a genomic target site sequence. In an aspect, a target strand overhang comprises at least 4 nucleotides that are complementary to a genomic target site sequence. In an aspect, a target strand overhang comprises at least 5 nucleotides that are complementary to a genomic target site sequence. In an aspect, a target strand overhang comprises at least 6 nucleotides that are complementary to a genomic target site sequence. In an aspect, a target strand overhang comprises at least 7 nucleotides that are complementary to a genomic target site sequence. In an aspect, a target strand overhang comprises at least 8 nucleotides that are complementary to a genomic target site sequence. In an aspect, a target strand overhang comprises at least 9 nucleotides that are complementary to a genomic target site sequence. In an aspect, a target strand overhang comprises at least 10 nucleotides that are complementary to a genomic target site sequence.

In an aspect, a non-target strand overhang comprises at least 1 nucleotide that is complementary to a genomic target site sequence. In an aspect, a non-target strand overhang comprises at least 2 nucleotides that are complementary to a genomic target site sequence. In an aspect, a non-target strand overhang comprises at least 3 nucleotides that are complementary to a genomic target site sequence. In an aspect, anon-target strand overhang comprises at least 4 nucleotides that are complementary to a genomic target site sequence. In an aspect, a non-target strand overhang comprises at least 5 nucleotides that are complementary to a genomic target site sequence. In an aspect, a non-target strand overhang comprises at least 6 nucleotides that are complementary to a genomic target site sequence. In an aspect, a non-target strand overhang comprises at least 7 nucleotides that are complementary to a genomic target site sequence. In an aspect, a non-target strand overhang comprises at least 8 nucleotides that are complementary to a genomic target site sequence. In an aspect, a non-target strand overhang comprises at least 9 nucleotides that are complementary to a genomic target site sequence. In an aspect, a non-target strand overhang comprises at least 10 nucleotides that are complementary to a genomic target site sequence.

In an aspect, a guided nuclease is capable of cleaving a genomic target site. In an aspect, this disclosure provides a method comprising introducing to a cell any recombinant DNA construct provided herein, where the guided nuclease cleaves the target site for a guided nuclease and a genomic target site, and where the sequence of interest is inserted into the genomic target site.

In an aspect, the sequence of nucleotide positions 20 to 23 of the target strand within a target site for a guided nuclease are the reverse complement of the sequence of nucleotide positions 20 to 23 of the target strand within a genomic target site. In an aspect, the sequence of nucleotide positions 1 to 19 of the target strand within a target site for a guided nuclease are identical to the sequence of nucleotide positions 1 to 19 of the target strand within a genomic target site. In an aspect, the sequence of nucleotide positions 1 to 19 of the target strand within a target site for a guided nuclease are not identical to the sequence of nucleotide positions 1 to 19 of the target strand within a genomic target site. In an aspect, the sequence of nucleotide positions 1 to 19 of the target strand within a target site for a guided nuclease are the reverse complement of the sequence of nucleotide positions 1 to 19 of the target strand within a genomic target site.

In an aspect, this disclosure provides an engineered double-stranded donor DNA molecule comprising one or more target sites for a guided nuclease adjacent to at least one sequence of interest, wherein the sequence of nucleotide positions 20 to 23 of the target strand within the one or more target sites for a guided nuclease are the reverse complement of the sequence of nucleotide positions 20 to 23 of the target strand within a genomic target site. In an aspect, the sequence of nucleotide positions 1 to 19 of the target strand within the one or more target sites for a guided nuclease are identical to the sequence of nucleotide positions 1 to 19 of the target strand within the genomic target site. In an aspect, the sequence of nucleotide positions 1 to 19 of the target strand within the one or more target sites for a guided nuclease are not identical to the sequence of nucleotide positions 1 to 19 of the target strand within the genomic target site. In an aspect the sequence of nucleotide positions 1 to 19 of the target strand within the one or more target sites for a guided nuclease are the reverse complement of the sequence of nucleotide positions 1 to 19 of the target strand within the genomic target site. In an aspect, a double-stranded donor DNA molecule comprises two or more target sites for a guided nuclease, and wherein the double-stranded donor DNA molecule comprises at least one target site for a guided nuclease positioned 5' to the at least one sequence of interest and at least one target site for a guided nuclease positioned 3' to the at least one sequence of interest. In an aspect, a double-stranded donor DNA molecule comprises at least two genes of interest.

In an aspect, this disclosure provides a method of introducing a double-stranded donor DNA molecule into a cell.

In an aspect, a guided nuclease generates a 4-nucleotide overhang after cleaving a recombinant nucleic acid construct at or near a target site for a guided nuclease. In an aspect, a guided nuclease generates a 4-nucleotide overhang after cleaving a target site for a guided nuclease in a plant genome, or at a site within 50 nucleotides of the target site in the plant genome.

In an aspect, a guided nuclease is a zinc-finger nuclease (ZFN). ZFNs are synthetic proteins consisting of an engineered zinc finger DNA-binding domain fused to the cleavage domain of the FokI restriction nuclease. ZFNs can be designed to cleave almost any long stretch of double-stranded DNA for modification of the zinc finger DNA-binding domain. ZFNs form dimers from monomers composed of a non-specific DNA cleavage domain of FokI nuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 nucleotides). The ZFN monomer can cute the target site if the two-ZF-binding sites are palindromic.

The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

In an aspect, a guided nuclease is a meganuclease. Meganucleases, which are commonly identified in microbes, are unique enzymes with high activity and long recognition sequences (>14 nt) resulting in site-specific digestion of target DNA. Engineered versions of naturally occurring meganucleases typically have extended DNA recognition sequences (for example, 14 nt to 40 nt). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In an aspect, a guided nuclease is a transcription activator-like effector nuclease (TALEN). In an aspect, a guided nuclease is a transcription activator-like effector-like (TALE-like) protein.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In one aspect, the nuclease is selected from a group consisting of PvuII, MutH, TevI and FokI, AlwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome resulting in modulation of gene expression. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs. As used herein, a "TALE binding site" (TBS) refers to a specific DNA sequence that is recognized and bound by the TALE DNA-binding domain of the TALE protein.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39:e82; and tale-nt[dot]cac[dot]cornell[dot]edu/about.

As used herein, a "sequence of interest" refers to refers to a polynucleotide sequence that is to be integrated into a genomic target sequence. In an aspect, a sequence of interest is exogenous to a plant genome into which it is integrated. In an aspect, a sequence of interest is endogenous to a plant genome into which it is integrated.

In an aspect, this disclosure provides a gene of interest. As used herein a gene of interest refers to a polynucleotide sequence that can produce a functional unit (e.g., without being limiting, for example, a protein, or a non-coding RNA molecule). In an aspect, this disclosure provides a gene of interest encoding a protein which confers an agronomic benefit (e.g., insect resistance, herbicide resistance, disease resistance, drought resistance, nitrogen use efficiency, protein expression, etc.) on a plant. In an aspect, this disclosure provides at least one gene of interest. In an aspect, this disclosure provides at least two genes of interest. In an aspect, this disclosure provides at least three genes of interest.

In an aspect, a recombinant nucleic acid construct comprises at least one sequence of interest for integration into a selected target site in a plant genome. In an aspect, a recombinant nucleic acid construct comprises at least two sequences of interest for integration into a selected target site in a plant genome.

A sequence of interest can comprise one or more of a promoter, an enhancer sequence, a leader sequence, a transcriptional start site, a protein coding sequence, a transcriptional stop site, a polyadenylation site, one or more exons, one or more introns, a 5'-UTR, a 3'-UTR, a recombinase binding site, a gene of interest, or any combination thereof. In one aspect, a sequence of interest encodes a non-coding RNA molecule, or a precursor thereof. In an aspect, a sequence of interest encodes a protein. In one aspect, a sequence of interest comprises an expression cassette. In one aspect, a sequence of interest comprises a target site for a guided nuclease.

Non-limiting examples of a non-coding RNA molecule include a microRNA (miRNA), a miRNA precursor (pre-miRNA), a small interfering RNA (siRNA), a small RNA (18 to 26 nucleotides in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single guide RNA (sgRNA). In an aspect, a non-coding RNA molecule comprises a miRNA. In an aspect, a non-coding RNA molecule comprises a siRNA. In an aspect, a non-coding RNA molecule comprises a ta-siRNA. In an aspect, a non-coding RNA molecule is selected from the group consisting of a miRNA, a siRNA, and a ta-siRNA.

In an aspect, a gene of interest is operably linked to a promoter. In an aspect, a gene of interest is operably linked to its native promoter. In an aspect, a gene of interest is operably linked to a heterologous promoter. As used herein, the term "heterologous" in reference to a promoter is a promoter sequence having a different origin relative to its associated transcribable DNA sequence, coding sequence or gene (or transgene), and/or not naturally occurring in the plant species to be transformed. The term "heterologous" can refer more broadly to a combination of two or more DNA molecules or sequences, such as a promoter and an associated transcribable DNA sequence, coding sequence or gene, when such a combination is man-made and not normally found in nature. In contrast, the term "native" in reference to a promoter is a promoter sequence that has the same origin relative to its associated transcribable DNA sequence and naturally occurs with the associated transcribable DNA sequence.

As used herein, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, cell cycle-specific, inducible, etc.

In an aspect, a recombinant nucleic acid construct comprises at least one promoter. In an aspect, a recombinant nucleic acid construct comprises at least two promoters. In an aspect, a recombinant nucleic acid construct comprises at least three promoters. In an aspect, a recombinant nucleic acid construct comprises at least four promoters. In an aspect, a recombinant nucleic acid construct comprises at least five promoters.

As used herein, "operably linked" refers to a functional linkage between two or more elements. For example, an operable linkage between a gene of interest and a regulatory sequence (e.g., a promoter) is a functional link that allows for expression of the gene of interest. Operably linked elements may be contiguous or non-contiguous.

Promoters that drive expression in all or most tissues of the plant are referred to as "constitutive" promoters. Promoters that drive expression during certain periods or stages of development are referred to as "developmental" promoters. An "inducible" promoter is a promoter that initiates transcription in response to an environmental stimulus such as heat, cold, drought, light, or other stimuli, such as wounding or chemical application. A promoter can also be classified in terms of its origin, such as being heterologous, homologous, chimeric, synthetic, etc.

In an aspect, a promoter provided herein is a constitutive promoter. In still another aspect, a promoter provided herein is an inducible promoter. In an aspect, a promoter provided herein is a tissue-specific promoter. In an aspect, a promoter provided herein is selected from the group consisting of a constitutive promoter, an inducible promoter, and a tissue-specific promoter.

RNA polymerase III (Pol III) promoters can be used to drive the expression of non-protein coding RNA molecules. In an aspect, a promoter provided herein is a Pol III promoter. In an aspect, a Pol III promoter provided herein is operably linked to a nucleic acid molecule encoding a non-protein coding RNA. In still another aspect, a Pol III promoter provided herein is operably linked to a nucleic acid molecule encoding a single-guide RNA. In a further aspect, a Pol III promoter provided herein is operably linked to a nucleic acid molecule encoding a CRISPR RNA (crRNA). In an aspect, a Pol III promoter provided herein is operably linked to a nucleic acid molecule encoding a tracer RNA (tracrRNA).

Non-limiting examples of Pol III promoters include a U6 promoter, an H1 promoter, a 5S promoter, an Adenovirus 2 (Ad2) VAI promoter, a tRNA promoter, and a 7SK promoter. See, for example, Schramm and Hernandez, 2002, *Genes & Development*, 16:2593-2620, which is incorporated by reference herein in its entirety. In an aspect, a Pol III promoter provided herein is selected from the group consisting of a U6 promoter, an H1 promoter, a 5S promoter, an Adenovirus 2 (Ad2) VAI promoter, a tRNA promoter, and a 7SK promoter. In an aspect, a guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In an aspect, a single-guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In an aspect, a CRISPR RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In an aspect, a tracer RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter.

In an aspect, a promoter provided herein is a Dahlia Mosaic Virus (DaMV) promoter. In an aspect, a promoter provided herein is a U6 promoter. In an aspect, a promoter provided herein is an actin promoter. In an aspect, a promoter provided herein is a Cauliflower Mosaic Virus (CaMV) 35S promoter. In an aspect, a promoter provided herein is a ubiquitin promoter.

In an aspect, a constitutive promoter is selected from the group consisting of a CaMV 35S promoter, an actin promoter, and a ubiquitin promoter.

Examples describing a promoter that can be used herein include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Molecular Biology* (1987) 9: 315-324), the CaMV 35S promoter (Odell et al., *Nature* (1985) 313: 810-812), the figwort mosaic virus 35S-promoter (U.S. Pat. Nos. 6,051,753; 5,378,619), the sucrose synthase promoter (Yang and Russell, *Proceedings of the National Academy of Sciences, USA* (1990) 87: 4144-4148), the R gene complex promoter (Chandler et al., *Plant Cell* (1989) 1: 1175-1183), and the chlorophyll a/b binding protein gene promoter, PC1SV (U.S. Pat. No. 5,850, 019), and AGRtu.nos (GenBank Accession V00087; Depicker et al., *Journal of Molecular and Applied Genetics* (1982) 1: 561-573; Bevan et al., 1983) promoters.

Promoter hybrids can also be used and constructed to enhance transcriptional activity (see U.S. Pat. No. 5,106, 739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

A selectable marker can be used to assist in the selection of transformed cells or tissue due to the presence of a selection agent, such as an antibiotic or herbicide, where the selectable marker gene provides tolerance or resistance to the selection agent. Thus, the selection agent can bias or favor the survival, development, growth, proliferation, etc., of transformed cells expressing the selectable marker gene. Commonly used selectable marker genes include, without being limiting, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or Cp4-EPSPS). Selectable marker genes, which provide an ability to visually screen for transformants, can also be used. Non-limiting examples include luciferase or green fluorescent protein (GFP), or a gene expressing a beta glucuronidase or uidA gene (GUS) for which various chromogenic substrates are known. In one aspect, a nucleic acid molecule provided herein comprises a selectable marker gene selected from the group consisting of nptII, aph IV, aadA, aac3, aacC4, bar, pat, DMO, EPSPS, aroA, luciferase, GFP, and GUS.

In an aspect, this disclosure provides a selectable marker gene. In an aspect, this disclosure provides a sequence encoding a selectable marker gene. In an aspect, this disclosure provides at least one selectable marker gene. In an aspect, this disclosure provides at least two selectable marker genes. In an aspect, this disclosure provides at least three selectable marker genes. In an aspect, a recombinant nucleic acid construct comprises at least one selectable marker gene.

In an aspect, a sequence encoding a selectable marker gene is operably linked to a promoter. In an aspect, a sequence encoding a selectable marker gene comprises at least one intron. In an aspect, a sequence encoding a selectable marker gene comprises at least two introns. In an aspect, an intron comprises a single intron sequence that has been split into two or more intron sequences.

In an aspect, a sequence encoding a selectable marker gene comprises a protein-coding sequence. In an aspect, a sequence encoding at least one selectable marker comprises (a) a promoter; (b) at least one intron; and (c) a protein-coding sequence. In an aspect, a recombinant nucleic acid construct comprises at least one sequence encoding at least one selectable marker gene. In an aspect, a recombinant nucleic acid construct comprises at least two sequences encoding at least two selectable marker genes.

In an aspect this disclosure provides compositions and methods for utilizing a replicase protein and Long Intergenic region (LIR) sequences from Geminiviruses and Nanoviruses to promote integration of a DNA sequence of interest at a selected location in a plant genome. Geminiviridae and Nanoviridae are families of plant-infecting viruses with circular ssDNA genomes. Geminiviruses and Nanoviruses typically replicate via a rolling circle mechanism. The replication initiation protein/replicase (Rep) recognizes a domain in the large intergenic region (LIR) and nicks the DNA at a 9-nt conserved site found on the hairpin structure of the LIR to promote rolling circle replication. As a result, newly synthesized ssDNA replicons are formed and converted again into dsDNA replicon. As used herein, "long intergenic region", "long intergenic repeat" or "LIR" refers to a long intergenic region containing a replicase/rep binding site that can mediate excision and replication by a viral replicase/Rep protein. LIRs comprise conserved or partially conserved site recognized and bound and nicked by a cognate viral replicase protein during rolling-circle replication. In an aspect, a LIR is derived from a Geminivirus. In an aspect, a LIR is derived from Soybean Chlorotic Spot Virus. In an aspect, a LIR is derived from a Nanovirus. In an aspect, a LIR is derived from the faba bean necrotic yellows virus. As used herein, "Replicase" or "replication initiation protein" or "viral replicase" or "Rep" refers to a protein capable of replicating DNA associated with its cognate LIR sequences. In an aspect, the replicase is derived from a Geminivirus. In an aspect, the replicase is derived from Soybean Chlorotic Spot Virus. In an aspect, the replicase is derived from a Nanovirus. In an aspect, the replicase is derived from Faba bean necrotic yellow virus.

Several embodiments relate to methods and compositions for providing multiple copies of a DNA sequence of interest for targeted integration at a selected site in a plant genome by flanking the DNA sequence of interest with LIR sequences and providing a cognate replicase. In some embodiments, the DNA sequence of interest comprises a target site for an guided nuclease (for example, a TALEN target site, a ZFN target site, a Cas12a target site, a Cas9 target site, an Iscel target site, etc). In some embodiments, the DNA sequence of interest comprises one or more homology arms. In some embodiments, the DNA sequence of interest and flanking LIR sequences are provided to a plant cell on a T-DNA via Agrobacterium mediated transformation. In some embodiments, the T-DNA further comprises one or more of an expression cassette encoding a replicase, an expression cassette encoding a guided nuclease, an expression cassette encoding a selectable marker, an expression cassette encoding one or more guide RNAs, wherein the one or more of expression cassettes are not provided between the LIR sequences. In some embodiments, the guided nuclease cleaves a target site in the plant genome. In some embodiments the guided nudlease cleaves a target site in the plant genome and the target site in the DNA sequence of interest. In some embodiments the T-DNA comprises one or more expression cassettes encoding a guide RNA that targets a site in the plant genome and a guide RNA that targets a site in the DNA sequence of interest. In some embodiments, a second T-DNA is provided that further comprises an expression cassette encoding a replicase.

Nanoviridae comprises two genera: Babuvirus and Nanovirus. All viruses in this family are multipartite, meaning they maintain their genomes in multiple segments of circular positive sense ssDNA. Examples of nanoviruses include faba bean necrotic yellow virus (FBNYV), subterranean clover stunt virus (SCSV), milk vetch dwarf virus (MDV), banana bunchy top virus (BBTV), abaca bunchy top virus (ABTV), coconut foliar decay virus (CFDV), cardamom bushy dwarf virus (CBDV), black medic leaf roll virus (BMLRV), and pea yellow stunt virus (PYSV).

Geminiviridae is a larger family comprising 14 genera. These include Becurtovirus, Begomovirus, Capulavirus, Curtovirus, Eragrovirus, Grablovirus, Mastrevirus, Topocuvirus, and Turncurtovirus. Examples of geminiviruses include the Maize streak virus (MSV), Soybean Chlorotic spot virus (SCSV), cabbage leaf curl virus (CLCV/CaL-CuV), tomato golden mosaic virus (TGMV), bean yellow dwarf virus (BeYDV; also referred to as chickpea chlorotic dwarf virus), African cassava mosaic virus, wheat dwarf virus (WDV), miscanthus streak mastrevirus, tobacco yellow dwarf virus, tomato yellow leaf curl virus (TyLCV), bean golden mosaic virus, beet curly top virus, and tomato pseudo-curly top virus. In an aspect, a sequence of interest provided herein is integrated into a plant genome. In an aspect, the integration of a sequence of interest into a plant genome comprises site-directed integration.

As used herein, "site-directed integration" refers to all, or a portion, of a desired sequence (e.g., a sequence of interest) being inserted or integrated at a desired site or locus within a plant genome (e.g., target sequence). In an aspect, a recombinant nucleic acid construct further comprises a first homology arm (HR1) and a second homology arm (HR2). As used herein, "homology arm" refers to a sequence that is essentially identical or essentially complementary to a sequence at or near a target site within a genome of the plant. In some embodiments, a homology arm is at least about 2, at least about 3, at least about 4, at least about 5, at least about at least about 6, at least about 7, at least about 8, at least about 9, at least about 10, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, at least about 200, at least about 250, at least about 300, at least about 350, at least about 400, at least about 450, at least about 500 or more nucleotides. Homology arms can direct the integration of a sequence of interest into a target site within a genome of a plant via homologous recombination, where a homology arm is essentially identical or essentially complementary, to a sequence at or near the target site within a genome of the plant. In an aspect, a sequence of interest comprises a homology arm at its 5'end and a homology arm at its 3' end. In an aspect, a target site for a guided nuclease is positioned between homology arms. In an aspect, a sequence of interest comprises a target site for a guided nuclease that is positioned outside of the sequence flanked by homology arms. In an aspect, a recombinant nucleic acid construct comprises a target sequence complementary to a spacer between two homology arms.

In an aspect, a method provided herein comprises site-directed integration of a sequence of interest (e.g., a gene of interest, an expression element, a sequence encoding a non-coding RNA, a recombination site, a target site for a guided nuclease, a transcriptional stop site, etc.) into a genome of a plant cell.

For site-directed integration, a double-strand break (DSB) or nick may first be made at a target site for a guided nuclease in a plant genome via a guided nuclease or ribonucleoprotein (e.g., a Cas12a system, a Cas9 system, etc.) provided herein. In the presence of a sequence of interest, the DSB or nick can then be repaired by homologous recombination (HR) between the homology arm(s) of the sequence of interest and the target sequence, or by non-homologous end joining (NHEJ), or by microhomology mediated end joining (MMEJ) resulting in site-directed integration of all or part of the sequence of interest into the target site for a guided nuclease in a plant genome to create the targeted insertion event at the site of the DSB or nick.

In an aspect, site-directed integration comprises the use of NNHEJ repair mechanisms endogenous to a cell. In an aspect, site-directed integration comprises the use of HR repair mechanisms endogenous to a cell. In an aspect, site-directed integration comprises the use of MMEJ repair mechanisms endogenous to a cell.

In an aspect, this disclosure provides a plant comprising a recombinant DNA construct provided herein. In an aspect, this disclosure provides a plant cell comprising a recombinant DNA construct provided herein. In an aspect, this disclosure provides a plant comprising an integrated sequence of interest provided by a method provided herein. In an aspect, this disclosure provides a plant cell comprising an integrated sequence of interest provided by a method provided herein.

Any plant or plant cell can be used with the methods and compositions provided herein. In an aspect, a plant is an angiosperm plant. In an aspect, a plant is a gymnosperm plant. In an aspect, a plant is a monocotyledonous plant. In an aspect, a plant is a dicotyledonous plant. In an aspect, a plant cell is an angiosperm plant cell. In an aspect, a plant cell is a gymnosperm plant cell. In an aspect, a plant cell is a monocotyledonous plant cell. In an aspect, a plant cell is a dicotyledonous plant cell.

In an aspect, a plant or plant cell is a plant or plant cell of a family selected from the group consisting of Alliaceae, Anacardiaceae, Apiaceae, Arecaceae, Asteraceae, Brassicaceae, Caesalpiniaceae, Cucurbitaceae, Ericaceae, Fabaceae, Juglandaceae, Malvaceae, Mimosaceae, Moraceae, Musaceae, Orchidaceae, Papilionaceae, Pinaceae, Poaceae, Rosaceae, Rutaceae, Rubiaceae, and Solanaceae.

In an aspect, a plant is selected from the group consisting of a corn plant, a rice plant, a sorghum plant, a wheat plant, an alfalfa plant, a barley plant, a millet plant, a rye plant, a sugarcane plant, a cotton plant, a soybean plant, a canola plant, a tomato plant, an onion plant, a cucumber plant, an *Arabidopsis* plant, and a potato plant. In an aspect, a plant cell is selected from the group consisting of a corn cell, a rice cell, a sorghum cell, a wheat cell, an alfalfa cell, a barley cell, a millet cell, a rye cell, a sugarcane cell, a cotton cell, a soybean cell, a canola cell, a tomato cell, an onion cell, a cucumber cell, an *Arabidopsis* cell, and a potato cell.

In an aspect, a plant is a corn plant. In an aspect, a plant is a soybean plant. In an aspect, a plant cell is a corn cell. In an aspect, a plant cell is a soybean cell.

In an aspect, a recombinant nucleic acid construct provided herein is provided to, or transformed into, a plant cell. *Agrobacterium*-mediated transformation is well-described in U.S. Pat. Nos. 5,159,135; 5,824,877; 5,591,616; 6,384,301; 5,750,871; 5,463,174; and 5,188,958, all of which are incorporated herein by reference.

Any suitable plant cell can be used for *Agrobacterium*-mediated transformation. Recipient plant cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In an aspect, this disclosure provides a plant chloroplast. In a further aspect, this disclosure provides an epidermal cell, a guard cell, a trichome cell, a root hair cell, a storage root cell, or a tuber cell. In an aspect, this disclosure provides a protoplast. In an aspect, this disclosure provides a plant callus cell.

Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In one aspect, this disclosure provides plant cells that are not reproductive material and do not mediate the natural reproduction of the plant. In an aspect, this disclosure also provides plant cells that are reproductive material and mediate the natural reproduction of the plant. In an aspect, this disclosure provides plant cells that cannot maintain themselves via photosynthesis. In an aspect, this disclosure provides somatic plant cells. Somatic cells, contrary to germline cells, do not mediate plant reproduction. In one aspect, this disclosure provides a non-reproductive plant cell.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise deoxyribonucleotides, ribonucleotides, or combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In an aspect, a nucleic acid molecule provided herein is an RNA molecule. In an aspect, a nucleic acid molecule provided herein is single-stranded. In an aspect, a nucleic acid molecule provided herein is double-stranded.

Nucleic acid molecules possess a directionality, or "orientation" due to the nature of their structure. Typically, a single DNA or RNA strand has a 5'-end where a phosphate group is attached to the 5' carbon of a ribose ring, and a 3'-end, where a hydroxyl group is attached to the 3' carbon of the ribose ring. Nucleic acids are transcribed in the forward, or 5' to 3', orientation. If two sequences are said to be in the "same orientation" they are both in the 5' to 3' orientation or they are both in the 3' to 5' orientation within the nucleic acid strand. If one sequence is in 5' to 3' orientation, it is said to be in opposite orientation as a sequence in 3' to 5' orientation.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Without being limiting, nucleic acids can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

The terms "percent sequence complementarity" or "percent complementarity" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence.

Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

As used herein, an "essentially identical" sequence refers to a sequence that is at least 95% identical to a second sequence. As used herein, an "essentially complementary" sequence refers to a sequence that is at least 95% complementary to a second sequence.

For optimal alignment of sequences to calculate their percent identity, various pair-wise or multiple sequence alignment algorithms and programs are known in the art, such as ClustalW or Basic Local Alignment Search Tool (BLAST®), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

As used herein, a first nucleic acid molecule (e.g., a guide RNA) can "hybridize" a second nucleic acid molecule (e.g. a target site for a guided nuclease) via non-covalent interactions (e.g., Watson-Crick base-pairing) in a sequence-specific, antiparallel manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine pairing with thymine, adenine pairing with uracil, and guanine (G) pairing with cytosine (C) [DNA, RNA]. In addition, it is also known in the art that for hybridization between two RNA molecules (e.g., dsRNA), guanine base pairs with uracil. For example, G/U base-pairing is partially responsible for the degeneracy (i.e., redundancy) of the genetic code in the context of tRNA anti-codon base-pairing with codons in mRNA. In the context of this disclosure, a guanine of a protein-binding segment (dsRNA duplex) of a subject DNA-targeting RNA molecule is considered complementary to an uracil, and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer nucleotides) the position of mismatches becomes important (see Sambrook et al.). Typically, the length for a hybridizable nucleic acid is at least 10 nucleotides. Illustrative minimum lengths for a hybridizable nucleic acid are: at least 15 nucleotides; at least 18 nucleotides; at least 20 nucleotides; at least 22 nucleotides; at least 25 nucleotides; and at least 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST® programs (basic local alignment search tools) and PowerBLAST programs known in the art (see Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www[dot]kazusa[dot] or[dot]jp[forwards slash]codon and these tables can be adapted in a number of ways. See Nakamura et al., 2000, Nucl. Acids Res. 28:292. Computer algorithms for codon optimizing a particular sequence for expression in a particular host cell are also available, such as Gene Forge (Aptagen; Jacobus, PA), are also available.

As used herein, "codon optimization" or "codon-optimized" refers to a process of modifying a nucleic acid sequence for enhanced expression in a host cell of interest by replacing at least one codon (e.g., at least 1, 2, 3, 4, 5, 10, 15, 20, 25, 50, or more codons) of a sequence with codons that are more frequently or most frequently used in the genes of the host cell while maintaining the original amino acid sequence (e.g., introducing silent mutations).

In an aspect, one or more codons (e.g., 1, 2, 3, 4, 5, 10, 15, 20, 25, 50, or more, or all codons) in a sequence encoding a recombinase, a guided nuclease, a sequence of interest, or a selectable marker gene correspond to the most frequently used codon for a particular amino acid. As to codon usage in plants, reference is made to Campbell and Gown, 1990, Plant Physiol., 92: 1-11; and Murray et al., 1989, Nucleic Acids Res., 17:477-98, each of which is incorporated herein by reference in their entireties.

In an aspect, a nucleic acid sequence encoding a guided nuclease is codon-optimized for a plant cell. In an aspect, a nucleic acid sequence encoding a guided nuclease is codon-optimized for a monocotyledonous plant cell. In an aspect, a nucleic acid sequence encoding a guided nuclease is codon-optimized for a dicotyledonous plant cell. In an aspect, a nucleic acid sequence encoding a guided nuclease is codon-optimized for a corn cell. In an aspect, a nucleic acid sequence encoding a guided nuclease is codon-optimized for a soybean cell.

In an aspect, a nucleic acid sequence encoding a recombinase is codon-optimized for a plant cell. In an aspect, a nucleic acid sequence encoding a recombinase is codon-optimized for a monocotyledonous plant cell. In an aspect, a nucleic acid sequence encoding a recombinase is codon-optimized for a dicotyledonous plant cell. In an aspect, a nucleic acid sequence encoding a recombinase is codon-optimized for a corn cell. In an aspect, a nucleic acid sequence encoding a recombinase is codon-optimized for a soybean cell.

In an aspect, a nucleic acid sequence is codon-optimized for a plant cell. In an aspect, a nucleic acid sequence encoding a guided nuclease is codon-optimized for a monocotyledonous plant cell. In an aspect, a nucleic acid sequence encoding a guided nuclease is codon-optimized for a dicotyledonous plant cell. In an aspect, a nucleic acid sequence encoding a guided nuclease is codon-optimized for a corn cell. In an aspect, a nucleic acid sequence encoding a guided nuclease is codon-optimized for a soybean cell. In an aspect, a nucleic acid sequence encoding a protein conferring an agronomic benefit is codon-optimized for a monocotyledonous plant cell. In an aspect, a nucleic acid sequence encoding protein conferring an agronomic benefit is codon-optimized for a dicotyledonous plant cell. In an aspect, a nucleic acid sequence encoding a protein conferring an agronomic benefit is codon-optimized for a corn cell. In an aspect, a nucleic acid sequence encoding a protein conferring an agronomic benefit is codon-optimized for a soybean cell.

In an aspect, a nucleic acid sequence encoding a selectable marker gene is codon-optimized for a plant cell. In an aspect, a nucleic acid sequence encoding a selectable marker gene is codon-optimized for a monocotyledonous plant cell. In an aspect, a nucleic acid sequence encoding a selectable marker gene is codon-optimized for a dicotyledonous plant cell. In an aspect, a nucleic acid sequence encoding a selectable marker gene is codon-optimized for a corn cell. In an aspect, a nucleic acid sequence encoding a selectable marker gene is codon-optimized for a soybean cell.

Having now generally described the disclosure, the same will be more readily understood through reference to the following examples that are provided by way of illustration, and are not intended to be limiting of the present disclosure, unless specified.

EXAMPLES

Example 1. Design and Testing of a Donor Vector

This example describes the design and testing of a donor vector comprising a selectable marker gene cassette, a CRISPR RNA-guided LbCas12a endonuclease expression system and a Gene of Interest (GOI) flanked by nuclease target sites for Site Directed Integration (SDI) at the GmTS1 target site within the soybean genome.

The *Agrobacterium* T-DNA vector configuration comprises a right border (RB) DNA sequence (SEQ ID NO: 1) and a left border (LB) DNA sequence (SEQ ID NO: 2) flanking five expression cassettes as illustrated in FIG. 1.

Cassette 1 is an expression cassette for a selectable marker gene, aadA. The expression cassette (SEQ ID NO: 3) comprises a promoter (SEQ ID NO: 4), a leader (SEQ ID NO: 5), and an intron sequence (SEQ ID NO: 6), all derived from the *Arabidopsis thaliana* Actin7 gene operably linked 5' to a nucleotide sequence encoding an *Arabidopsis* EPSPS transit peptide (SEQ ID NO: 7) followed by the *E. coli* aadA reporter gene (SEQ ID NO: 8) and a transcription termination sequence from the *Agrobacterium* nos gene (SEQ ID NO: 9).

Cassette 2 is an expression cassette comprising a Gene of Interest (GOI 1) under the control of a non-constitutive promoter.

Cassette 3 is an expression cassette encoding the CRISPR/Cas12a nuclease from *Lachnospiraceae bacterium* ND2006 (LbCas12a) (SEQ ID NO:33).

Cassette 4 is an expression cassette encoding a LbCas12a gRNA and comprises a soybean U6 promoter (SEQ ID NO: 34) operably linked to DNA encoding the LbCas12a guide RNA. The guide RNA comprises a 21-nucleotide crRNA (SEQ ID NO: 24), a common guide RNA scaffold sequence compatible with the LbCas12a enzyme, along with a unique 23-nucleotide spacer complementary to the GmTS1 target site within the soybean genome.

Cassette 5 is an expression cassette encoding a second Gene of Interest (GOI 2) under the control of a constitutive promoter. Cassette 5 is flanked by GmTS1 target sites as shown in FIG. 1. The T-DNA structure is designed to integrate GOI 1 into the specific chromosome target site (GmTS1) after LbCas12a cleaves the GOI 1 flanking target sites and the chromosome target site simultaneously, while the selectable marker gene, together with other accessary nuclease gene cassettes, integrates in a separate chromosomal location. This configuration allows integrated GOI 1 to be segregated away from the marker gene in progeny.

Excised embryos from A3555 soybean plants are co-cultured with *Agrobacterium* comprising the vector described above. Transformed plants are selected on spectinomycin. Leaf samples from the regenerated plantlets are harvested after 10 weeks and genomic DNA is extracted from shoot tissue.

To identify plants with site directed integration of GOI1 at the GmTS1 target site, flanking PCR assays similar to those described in WO 2019/084148 (which is incorporated by reference herein in its entirety) using a pair of PCR primers flanking the intended GmTS1 target site are performed. Genomic DNA from positive flanking PCR results indicating putative SDI events are sequenced.

As noted above, the expectation is that GOI 1 would be excised from the T-DNA, either pre- or post-integration of the T-DNA into a chromosome, and then inserted, independent of the rest of the T-DNA, at a specific target site in a chromosome that was cut by the LbCas12a-gRNA.

From 1000 plantlets, 67 events with positive flanking PCR products were sequence-analyzed, among which a total of 10 SDI events were identified. Eight single copy SDI events were identified at the GmTS1 chromosomal target site and these events were subjected to detailed sequence analysis.

Of the 8 events analyzed, all comprised the T-DNA inserted at the target site by non-homologous end joining (NHEJ). No SDI events having a single copy insertion with intact cassettes and the expected transgene/genome junction were identified. Interestingly, of the 8 events analyzed, 6 showed unexpected linkage of the RB and LB sequences as illustrated in FIG. 1B. This unexpected conformation can be explained by linearization of a circularized T-DNA by CRISPR nuclease cleavage at least one of the two gRNA target sites followed by integration of the linearized T-DNA by NHEJ at the GmTS1 target site in the chromosome.

Sixteen events in which the T-DNA had inserted randomly at sites other than the GmTS1 target site were also analyzed by the same sequence analysis strategy. None of these sixteen untargeted events showed evidence of novel RB and LB junctions as were observed in the on-target events.

T-strand/T-DNA circularization in plants has previously been described (see Koukolikovi-Nicola et al. (1985); Singer et al. (2012)). Circularized T-DNA structures have been rescued from plant cells with *Agrobacterium* co-culture. The junction sequence of the circle intermediate was confirmed to occur in the 25-nucleotide direct repeat normally found at the ends of the T-DNA region of the Ti plasmid (Koukolikovi-Nicola et al. (1985)). Evidence showed that single-stranded T-DNA is converted into a double-stranded form prior to integration (Singer et al. (2012)). It has been proposed that termini of linear double-stranded T-DNAs are recognized and repaired by the plant's DNA double-strand break-repair machinery, which leads integration into the chromosome, the formation of extrachromosomal complex T-DNA structures that subsequently may integrate, or extra-chromosomal circular forms of the T-DNA (Singer et al. (2012)). The circularized T-DNA was speculated to be a dead-end in plant cells compared to linear double stranded T-DNA (Singer et al. (2012)).

Without being bound by any scientific theory, in a subset of T-DNA molecules, the dsDNA T-DNA spontaneously circularizes, joining the RB end to the LB end, creating an imprecise junction that can comprise truncations of both ends. LbCas12a mediated cleavage of the circular T-DNA at least one of the GmTS1 target sites linearizes it, creating a substrate for targeted insertion of the linearized T-DNA into the chromosomal target site cleaved by the gRNA directed nuclease.

Example 2. Design and Testing of T-DNA Vectors

This example describes the design and testing of T-DNA vectors comprising a split marker cassette adjacent to the RB and LB and a single target site for the CRISPR LbCas12a nuclease system. This vector configuration is expected to enrich targeted insertions in the soybean genome and result in a disrupted marker gene cassette in random T-DNA integrations.

The aadA selection marker cassette: The aadA expression cassette (SEQ ID NO: 3) (see FIG. 2) described in Example 1 comprises a promoter (P-ACT7) (SEQ ID NO: 4), a leader (L-) (SEQ ID NO: 5), and an intron sequence (I-Act7)(SEQ ID NO: 6), all derived from the *Arabidopsis thaliana* Actin7 gene operably linked 5' to a nucleotide sequence encoding an *Arabidopsis* EPSPS transit peptide (CTP)(SEQ ID NO: 7) followed by the *E. coli* aadA reporter gene (aadA)(SEQ ID NO: 8) and a transcription termination sequence from the *Agrobacterium* nos gene (T-nos)(SEQ ID NO:9). Position 270 within the Actin7 (Act7) intron sequence of the aadA cassette was chosen as the split site. The 5' portion of aadA cassette (5' Marker cassette) comprising the promoter, leader and first 270 nucleotides of the Act7 intron is set forth as SEQ ID NO: 10. The "3' Marker cassette" (SEQ ID NO:11) comprises the 3' portion of Act7 intron, aadA coding sequence and the nos transcription terminator.

RB and LB truncations: The vector described in Example 1 utilizes the 505 nucleotide octopine RB sequence (SEQ ID NO: 1) and the 442 nucleotide octopine LB sequence (SEQ ID NO: 2). To facilitate placement of the border sequences within the intron and promote efficient intron splicing, the inner border sequences within RB and/or the LB are truncated (see FIG. 3). The truncations are designed to reduce the border residue size after end-joining inside the split intron. Two *Agrobacterium* T-DNA vectors are designed for this purpose and are described below.

Figure 3:
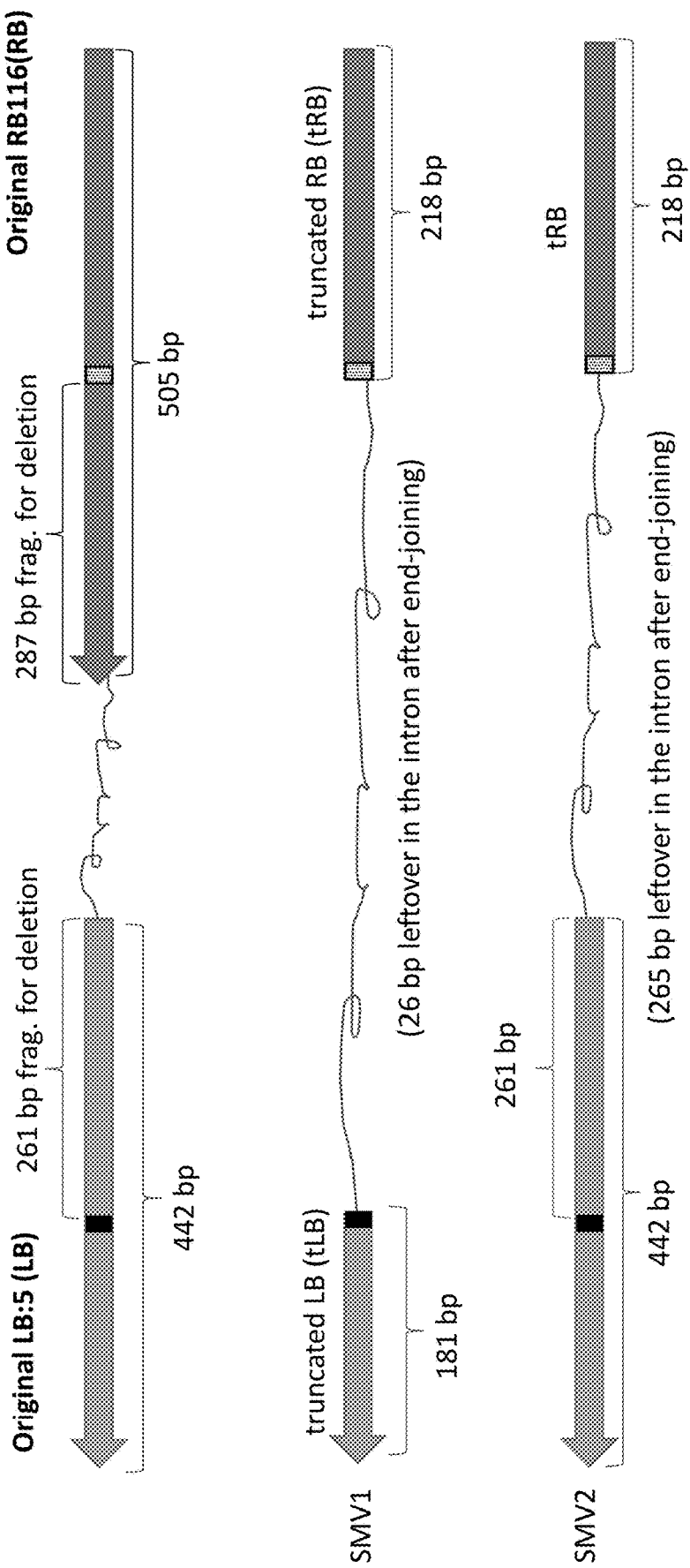
FIG. 3 depicts a schematic illustrating Right Border (RB) and Left Border (LB) inner-border sequence regions, and deletions of said regions designed to result in less inner sequence region in the intron (FIG. 2) after splicing.

*Glycine max* Split Marker Vector 1: GmSMV1 T-DNA vector comprises RB and LB inner border sequence deletions (see FIG. 3), which would result in a 26 nucleotide border residue retained within the reconstituted Act7 intron following T-DNA end joining. The 181 nucleotide truncated LB sequence (tLB) sequence is set forth as SEQ ID NO: 12, and the 218 nucleotide truncated RB sequence (tRB) is set forth as SEQ ID NO: 13. As shown in FIG. 3, the 25 nucleotide essential core LB sequence (SEQ ID NO: 14) and essential core RB sequence (SEQ ID NO: 15) are retained in the truncated versions. The 5' Marker cassette (SEQ ID NO: 10) is PCR amplified and fused 5' to the tRB as shown in FIG. 4. The 3' Marker cassette (SEQ ID NO: 11) was PCR amplified and fused 3' to the tLB as shown in FIG. 4. Additionally, the GmSMV1 vector comprises 4 functional cassettes present in the vector described in Example 1 (see FIG. 4).

Cassette 1 is an expression cassette for a Gene of Interest (GOI 2) under the control of a non-constitutive promoter. Cassette 2 is an expression cassette for LbCas12a nuclease (SEQ ID NO: 33). Cassette 3 is an expression cassette for the LbCas12a gRNA and comprises a soybean U6 promoter (SEQ ID NO: 34) operably linked to a 21 nucleotide crRNA sequence and a unique 23 nucleotide spacer sequence that is complementary to the GmTS1 target site. Cassette 4 is an expression cassette encoding a second Gene of Interest (GOI 1) under the control of a constitutive promoter. The vector also comprises a 27 nucleotide sequence encoding the GmTS1 target site situated 3' to the GOI 2 cassette. Finally, the GOI 2 cassette with the GmTS1 target site is flanked by LoxP recombination sites (see US 2020/0032289, which is incorporated by reference herein in its entirety).

*Glycine max* Split marker Vector 2: The GmSMV2 T-DNA vector has a design similar to GmSMV1 with four functional cassettes, a split marker and tRB border sequence, but comprises an intact and longer LB sequence (see FIG. 3 and FIG. 4). This results in a 265 nucleotide border residue retained within the re-constituted Act7 intron following T-DNA end joining.

Plant transformation and SDI screening: Excised embryos from A3555 soybean plants were co-cultured with *Agrobacterium* comprising GmSMV1 or GmSMV2 as described above. In total, 48,000 explants were co-cultured with the two constructs and selected on spectinomycin medium for shoot elongation. Without being bound to any scientific theory, in a majority of the explants, the linear T-DNA randomly integrated into DSBs in the chromosome. Since the aadA marker cassette is not functional, these explants are not expected to survive in spectinomycin selection medium. In a subset of T-DNA molecules, the dsDNA T-DNA spontaneously circularizes joining the RB end to the LB end. Circularization reconstitutes a spliceable intron (within the selectable marker cassette) and results in a functional aadA expression cassette. This results in recovery of plants where the T-DNA either went through the circularization pathway or had ligated to other T-DNAs to form dimers with a RB-LB junction.

The spectinomycin resistant shoots were transferred into soil plugs for rooting. DNA was extracted from leaf samples and used for copy number determination by TaqManrm based assays, which are known in the art. To identify plants with site directed integration of the T-DNA at the GmTS1 site, flanking PCR assays similar to those described in WO 2019/084148 (which is hereby incorporated in its entirety) using a pair of PCR primers flanking the intended GmTS1 target site were performed. DNA from flanking PCR positive putative targeted events were subjected to sequence analysis. In total, 336 samples (84 samples/plate) were collected and analyzed to identify targeted events (see Table 1). From these 50 events with low copy numbers (1-2 copies) from each construct with flanking PCR positive results for either flanking regions were further advanced for genome sequencing and detailed integration analysis. The results are summarized in Table 1 and compared to events generated from the control T-DNA vector comprising an intact aadA selectable marker cassette as described in Example 1.

A quality SDI event is defined as single copy insertion of T-DNA at the targeted site with intact cassettes and transgene/genome junction essentially as expected. The SDI rate is defined as the ratio of quality SDI events to samples. Quality SDI rate in 2 copy events indicates that these plants had 2 copies of the TDNA with at least 1 TDNA being a quality SDI insert. These plants would require segregation of progeny for single copy commercial quality SDI events.

TABLE 1

Summary of SDI construct transformation. "TF" indicates Transformation Frequency and "Q SDI" indicates Quality Site-Directed Integration Event. The Control T-DNA was as described in Example 1.

| Construct | Explants | Events in Soil Plugs | TF | Analyzed Samples | Q SDI Rate by Plant no. | Q SDI Rate in 2 copy events | Combined SDI Rate by Plant No. | Potential Q SDI Rate by Explants |
|---|---|---|---|---|---|---|---|---|
| Control | 30000 | 1824 | 6.1% | 1670 | 0.3% (5/1670) | N/A | 0.3% (5/1670) | 0.017% (5/30000) |
| GmSMV1 | 48000 | 1437 | 3% | 336 | 2.97% (10/336) | 1.49% (5/336) | 4.46% (15/336) | 0.13% (64/48000) |
| GmSMV2 | 48000 | 761 | 1.58% | 336 | 2.08% (7/336) | 0.89% (3/336) | 2.97% (10/336) | 0.047% (22/48000) |

As shown in Table 1, a ten-fold increase in Quality SDI event generation rate was observed for GmSMV1 when compared to the control. A seven-fold increase was observed for GmSMV2 when compared to the control. 3% transformation frequency (TF) was observed in GmSMV1 cocultured explants compared to 1.58% TF from GmSMV2 cocultured explants. This suggests, without being limited by any scientific theory, that presence of the longer LB residue within the Act7 intron in SMV2 may negatively impact efficient intron splicing and functionality.

Example 3. Design and Testing of T-DNA Vectors

This example describes the design and testing of T-DNA vectors with split marker cassettes adjacent to the RB and LB and a target site for the CRISPR LbCas12a nuclease system. This vector configuration is expected to enrich targeted insertions at the *Zea mays* ZmTS1 genomic region and result in a disrupted marker gene cassette in random T-DNA integrations.

The CP4 selection marker cassette: The functional CP4 expression cassette (SEQ ID NO: 17) comprises a Rice actin1 promoter (SEQ ID NO:18), a leader (SEQ ID NO:19), and an intron sequence (SEQ ID NO: 20), operably linked 5' to a nucleotide sequence encoding an *Arabidopsis* EPSPS transit peptide (SEQ ID NO: 7) followed by the coding sequence for the *Agrobacterium* EPSPS-CP4 reporter gene (SEQ ID NO: 21) that provides resistance to glyphosate and a transcription termination sequence from the *Agrobacterium* nos gene (SEQ ID NO: 9). Position 239 within the Actin1 intron sequence of the CP4 cassette is chosen as the split site. The 5' portion of CP4 cassette (5' CP4 Marker cassette) comprising the promoter, leader and first 239 nucleotides of the Actin1 intron is set forth as SEQ ID NO: 22. The "3' CP4 Marker cassette" comprising the 3' portion of 239 nucleotide Actin1 intron, CP4 coding sequence, and the nos transcription terminator is set forth as SEQ ID NO: 23.

Corn Split Marker Vector 1: ZmSMV1 T-DNA vector comprises tRB (SEQ ID NO: 13) and tLB (SEQ ID NO: 12) sequences, four functional cassettes, and a Split CP4 marker cassette (see FIG. 4). The 5' CP4 Marker cassette (SEQ ID NO: 22) was positioned 5' to the tRB. The 3' Marker cassette (SEQ ID NO: 23) is positioned 3' to the tLB. The vector also comprised an expression cassette for a Gene of Interest (GOI 1) under the control of a non-constitutive promoter and an expression cassette for LbCas12a nuclease (SEQ ID NO: 26). An expression cassette comprising encoding the LbCas12a guide RNA comprising the 21 nucleotide crRNA (SEQ ID NO: 24), a common guide RNA scaffold sequence compatible with the LbCas12a enzyme, and a unique 23 nucleotide spacer complementary to the Zm7.1_TS1 target site was further provided. Also provided was an expression cassette encoding a second Gene of Interest (GOI 2) under the control of a constitutive promoter. The vector also comprised a 27 nucleotide sequence encoding the ZM TS1 target site situated 3' to the GOI 2 cassette. Finally, the GOI 2 cassette with the ZmTST target site was flanked by LoxP recombination sites.

Example 4. Corn Transformation

Corn transformation, flank PCR and SDI confirmation: Corn 01DKD2 cultivar embryos were transformed with *Agrobacterium* containing the ZmSMV1 T-DNA vector described in Example 3 using methods known in the art. Stably transformed plants were selected on glyphosate. Leaf samples from regenerated plantlets were harvested after two weeks, and genomic DNA was extracted for copy number determination by TaqMan™ based assays, which are known in the art.

To identify plants with site directed integration of the T-DNA at the ZmTS1 site, a flank PCR assay was performed using a pair of PCR primers flanking the intended target site. DNA from flank PCR positive putative SDI events was subjected to sequence analysis. Events with low copy numbers (1-2 copies) and with flank PCR positive results for either flanking regions were further advanced for genome sequencing and detailed integration analysis to identify events and rates of commercial quality SDI. As noted in Table 2, of the 84 samples analyzed, 1 SDI event was identified.

TABLE 2

Summary of SDI construct transformation. TF indicates Transformation Frequency and Q SDI indicates Quality Site-Directed Integration Event.

| Construct | Initial explants | Events in soil plugs | TF | Analyzed samples | Total SDI | Quality SDI rate by plant No. |
|---|---|---|---|---|---|---|
| ZmSMV1 | 112500 | 90 | 0.08% | 84 | 1 | 0 |

Example 5. Design of a Binary Construct

Figure 5:
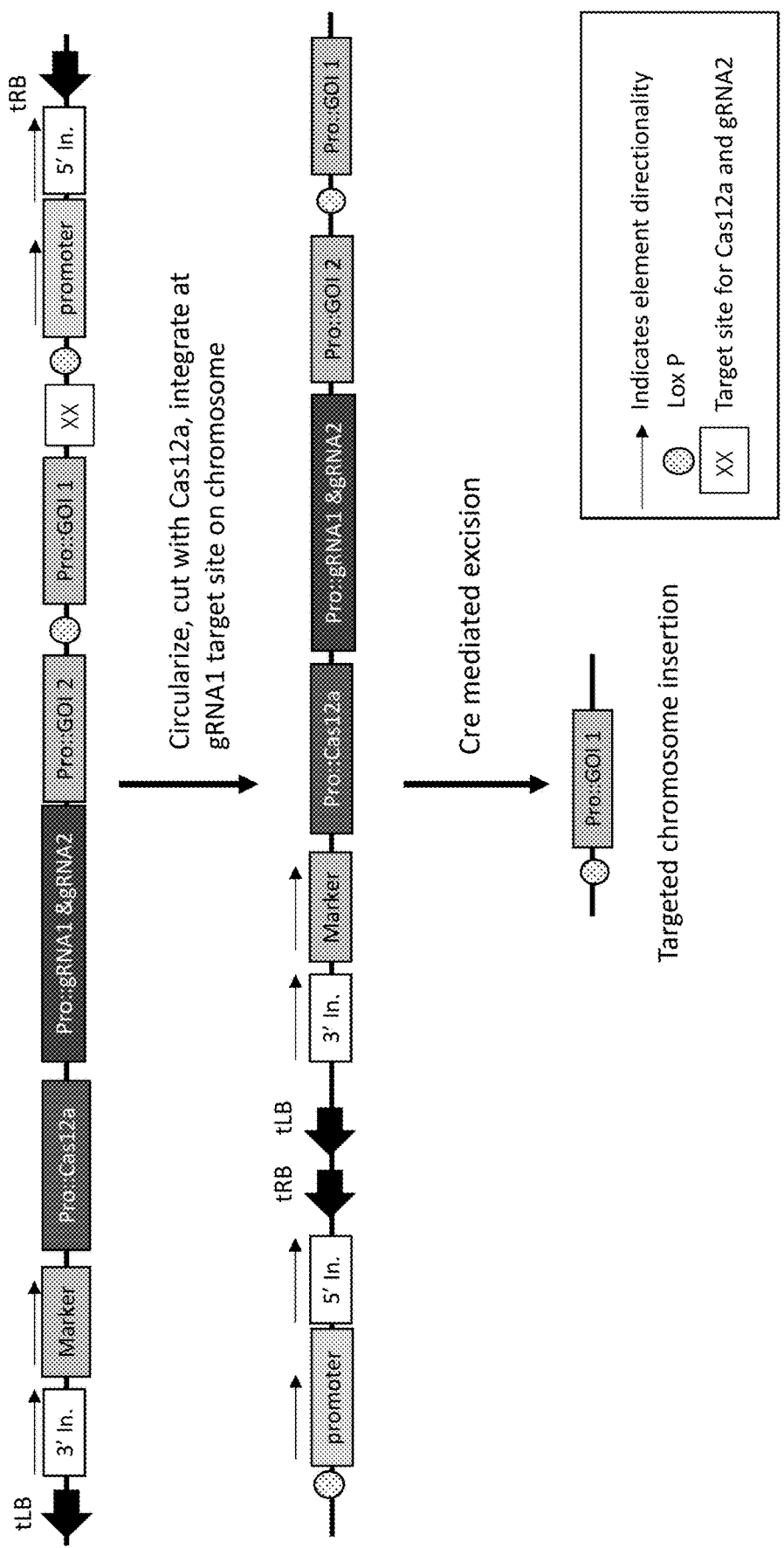
FIG. 5 depicts a schematic illustrating configuration of an *Agrobacterium* T-DNA vector designed with two gRNAs expressed on T-strand: one targeting a unique site in the circularized T-strand and one targeting a unique site in the genome.

This example describes the design of a binary construct with two gRNA expression cassettes provided on the T-DNA: one targeting a unique site in the T-DNA and the second targeting a unique site in the genome (see e.g., FIG. 5).

Cas12a cuts at a 23-nt target region that is immediately preceded by a PAM site. When Cas12a cuts, it cuts after position 19 on one strand (the "Non-target Strand") and after position 23 on the opposite strand (the "Target Strand"), generating a 4-nt 5' overhang on each strand (see e.g., FIG. 16). The 5' overhang on the end containing the PAM site and 19nt of the target site is marked with a letter designation A. The 5' overhang on the other fragment, that only has the 4-nt target site fragment and not containing the PAM is denoted as A'. A' is the reverse complement of A and can theoretically re-anneal perfectly to the A overhang.

Observations from Example 1 and 2 suggest that LbCas12a targeting sites that differ between the T-DNA and the genome could lead to increased efficiency of SDI. A substantial majority of SDI events observed were in the "reverse" orientation, where the orientation of the cleaved target site of the T-DNA insertion is in the opposite orientation to that of the cleaved target site on the genome. See e.g., FIG. 17. As shown in FIG. 17, at one end, an inverted pair of cleaved target sites (minus some amount of sequence chew back) are linked (A to A linkage), while at the other end, the linkage is between the 4 bp 3' ends of the target regions, inverted, and with some sequence chew back. See FIG. 17; A' to A' linkage. The chew back observed at the A' to A' linkage for reverse orientation events was significantly shorter compared to the chew back observed at all other sets of NHEJ linkages, which appear to be of similar magnitude. See Table 2. Without being limited by any scientific theory, this may be the initiating event in reverse orientation SDI and thus avoids exposure to chew back.

The average sequence chew back is only 5.7 nucleotides for the chromosome 6 (CR06) A' end, and 1.8 nucleotides for the T-DNA A' end. Also, the prevalence of ambiguous assignments is much greater than is expected from random occurrence: 14 of 21 events (67%) show this, and in 12 of the 14, the ambiguity is consistent with a microhomology-mediated annealing of the 5' single strand end of the cleaved T-DNA to the 5' single-strand end of CR06. Only three events were observed to have slightly longer chew back of an additional two or three nucleotides. These observations are specific to events in the reverse (REV) orientation. Events in the forward (FWD) orientation were fewer (6 total) and had longer chew backs.

TABLE 3

Average lengths of chew back (base pairs) at all linkages in FWD and REV events derived from donor vector described in Example 1 and target site GmTS1 on the chromosome.

| | Chew back at each end | |
|---|---|---|
| Reverse Orientation (REV) 21 events | | |
| CR06 A'::T-DNA A' | CR06 A' 5.7 nt | T-DNA A' 1.8 nt |
| RB :LB | RB 12 nt | LB 20 nt |
| T-DNA A::CR06 A | T-DNA A 13.6 nt | CR06A 14.9 nt |
| Forward Orientation(FWD) 6 events | | |
| CR06 A::T-DNA A' | CR06A 26.7 nt | T-DNA A' 14.7 nt |
| RB ::LB | RB 12.2 nt | LB 40.5 nt |
| T-DNA A::CR06 A" | T-DNA A 21.0 nt | CR06A 15.0 nt |

Taken together, these data provide evidence for two classes of events. Class I events, which are in the reverse (REV) orientation, are typified by short chew back at the A'/A' linkage, a high prevalence of apparent microhomologies (1-3 nt sequences at the junction that are attributable to either of the pre-joined pieces) and occur at an enhanced frequency. Class II events, which are typified by longer chew back, seem to have no preference for directionality (approximately equal numbers exist in both directions). The data also provide evidence suggesting that microhomologies enhance the efficiency of on-target insertions. Not wishing to be bound by a particular theory, it may be possible to maximize the efficiency of donor insertion by maximizing the likelihood of productive microhomology-assisted NHEJ, while minimizing the occurrence of non-productive NHEJ (as detailed below). Microhomology-assisted NHEJ can occur when the 5' overhang (A') of the chromosome and the 5' overhang (A') of the T-DNA (each either full-length or partially chewed back) have annealing base pair(s) at their termini that can then be filled in for healing of the junction. See FIG. 15C. Without being bound by any theory, it may be possible to increase the efficiency of reverse orientation, Class 1 events, by altering the T-strand target site to maximize the potential for microhomology with the cleaved genomic target site.

Figure 18B:
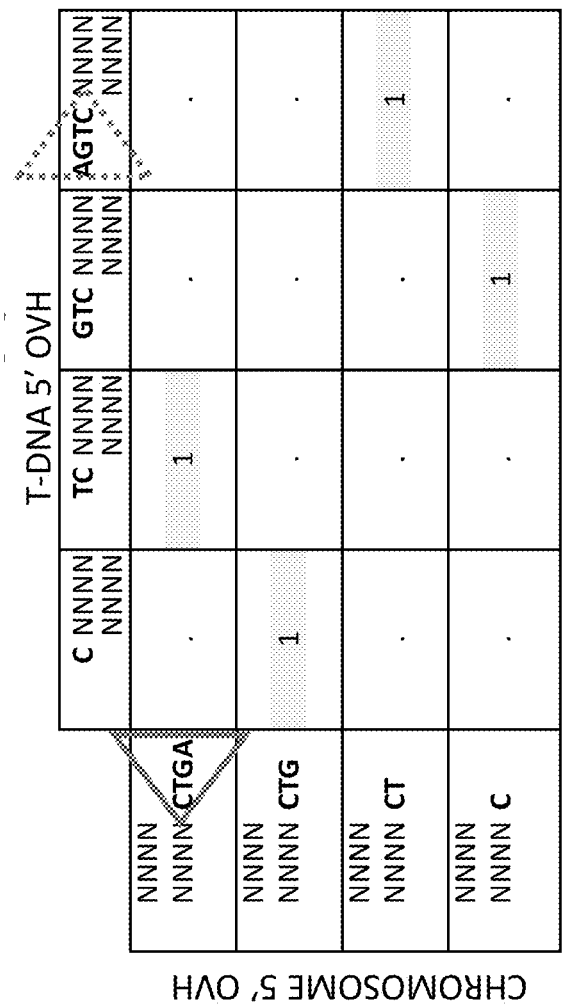
FIG. 18B depicts microhomology at A'/A' linkage when the target site on the chromosome and T-DNA is the same GmTS1 site. Each box queries whether the ends are capable of annealing and indicates the number of bp of annealing that are possible for all the possible small truncations of the two A' regions. Four of sixteen combinations predict a possible 1 bp end joining: in two cases a single A-T pairing, and in two cases a single C-G pairing.
Figure 18D:
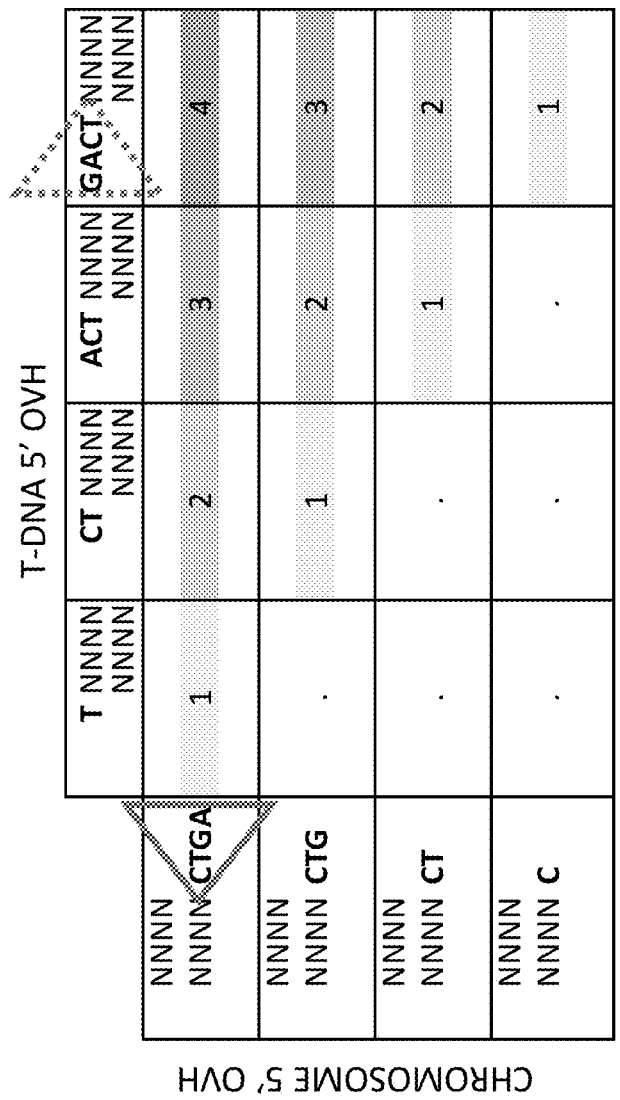
FIG. 18D depicts microhomology potential at A'/A' linkage when the Chromosomal target site is GmTS1 and the T-DNA target site is an engineered target site GmTS1_4RC. Microhomology potential increased to ten of sixteen pairings, including six with greater than 1 bp annealing possible.

To visualize this process, charts of the potential overlaps can be generated, both to identify the partners that could be involved in microhomology directly, and the number of base pairs that are involved in the possible microhomology. See FIG. 17. To maximize the microhomology potential, it is preferable to alter at least the last four nucleotides (nt) of the target site on the T-DNA strand to their reverse complement (compare for instance GmTS1 and GmTS1_4RC in FIG. 18C). As shown in FIG. 18 D the A'/A' interaction between the cleaved genomic target site and the cleaved T-DNA target site has significant increase in both the number of pairings that have microhomology potential, but also the bp lengths of those individual potentials.

Two targets sites 20.38.4 (SEQ ID NO:27) and 05.37.8 (SEQ ID NO: 30) within the soy chromosome were identified and gRNA spacer sequences were designed to target these sites (See Table 4). T-DNA Target sites were designed to promote microhomology assisted annealing with each genomic target site (TS) (See Table 4, rows 2, 3, 5, and 6). Constructs were designed to promote an increase in microhomology assisted SDI in two different ways.

In the first design ("Design 1"), positions 1 to 19 are identical between genomic target site and T-DNA target site. However, positions 20 to 23 within the T-DNA target site are designed to be the reverse complement (RC) of positions 20 to 23 of the genomic target site. For example, compare rows 1 and 2 or rows 4 and 5 in Table 4. Because of the tendency of the T-DNA to insert into the chromosome with the A' end of the cleaved T-DNA pairing with the A' end of the cleaved chromosome (and A end of the cleaved T-DNA pairing with the A end of the cleaved chromosome), the strands involved in the initiating end will be complementary (maximizing microhomology assistance) and would have many opportunities, even with minor deletion of either strand, to have shorter micro-homologies.

In the second design ("Design 2"), the sequence of the T-DNA target site is completely unrelated to the genomic target site, except that as in the previous design, positions 20 to 23 within the T-DNA target site are designed to be the reverse complement (RC) of positions 20 to 23 in genomic target site. For example, compare rows 1 and 3 or rows 4 and 6 in Table 4. In cases where Design 1 results in a gRNA that is predicted to be a poorly performing gRNA, or to produce off-target cleavages, Design 2 may cleave the circularized T-DNA more effectively. Additionally, since the sequence on the second end will not form a short inverted repeat with the cleaved genomic copy of target 1, it may result in an increase in efficiency if the absence of an inverted repeat increases the efficiency of healing at that end. Alternate lengths of designed 3' inversions are also anticipated, in the range of 1 to 6 nucleotides, all of which are predicted to similarly create the opportunity for microhomology-assisted increases in integration rates.

circularizes and Cas12a-gRNA2 complexes cleave the circularized T-DNA and Cas12a-gRNA1 complex cleaves the genomic target site. The T-DNA circularization and subsequent cleavage allows for targeted integration of the linearized T-DNA into the genomic target site. Circularization and linearization also reconstitutes a spliceable intron within the marker cassette thus allowing the promoter to drive expression of the selectable marker gene, thus allowing for selection of events that have undergone circularization followed by T-DNA integration. Flank PCR assays and genomic DNA sequencing are carried out to identify plants with targeted

TABLE 4

Soy Target sites and T-DNA target sequences. Four base pairs of reverse-complement design are underlined, T-DNA target sites comprising sequences that are not present in the soy genome target site are shown in bold.

| | Design | Target site | PAM | gRNA/target | SEQ ID NO |
|---|---|---|---|---|---|
| 1 | Genomic target site | 20.38.4 | TTTA | GCAACACCAATTAACAGTTCAAT | 27 |
| 2 | T-DNA Target site Design 1 | 20.38.4_4RC | TTTA | GCAACACCAATTAACAGTT<u>ATTG</u> | 28 |
| 3 | T-DNA Target site Design 2 | artificial_20_4RC | TTTA | GTATAATATGATGGCATGC<u>ATTG</u> | 29 |
| 4 | Genomic target site | 05.37.8 | TTTA | GTCCGGGTTGATATGGTGAAAGA | 30 |
| 5 | T-DNA Target site Design 1 | 05.37.8_4RC | TTTA | GTCCGGGTTGATATGGTG<u>ATCTT</u> | 31 |
| 6 | T-DNA Target site- Design 2 | artificial_05_4RC | TTTA | GTATAATATGATGGCATGC<u>TCTT</u> | 32 |

6 T-DNA constructs are produced that comprise, in 5' to 3' order, a truncated left border (tLB) sequence; a 3' marker cassette fragment (SEQ ID NO:11); a promoter operably linked to a sequence encoding Cas12a; a promoter operably linked to a sequence encoding a guide RNA array which comprises gRNA1 and gRNA 2 (gRNA1 targets a native chromosomal target site while gRNA 2 targets a site of the T-DNA); a promoter operably linked to a sequence encoding a gene of interest 2, a lox site, a promoter operably linked to a sequence encoding a gene of interest 1, a target site that is recognized by Cas12a and gRNA2, a second lox site, a 5' Marker cassette fragment (SEQ ID NO: 10); and a truncated right border (tRB) sequence. See FIG. 5.

integration events. Rates of targeted integration between test and control vectors are analyzed to determine if increasing microhomology between the A' ends of Cas12a cleaved fragments in the T-DNA and genomic target site leads to increased efficiency of targeted integration.

TABLE 5

Vectors comprising gRNA arrays

| T-DNA vectors | gRNA1 (targeting genomic site) | gRNA 2 (targeting T-DNA site) |
|---|---|---|
| Vector A | 20.38.4 | 20.38.4_4RC |
| Vector B | 20.38.4 | artificial_20_4RC |
| Vector C | 05.37.8 | 05.37.8_4RC |
| Vector D | 05.37.8 | artificial_05_4RC |
| Vector E (control) | 20.38.4 | 20.38.4 |
| Vector F (control) | 05.37.8 | 05.37.8 |

The constructs are introduced to plant cells via *Agrobacterium*-mediated transformation. A subset of the T-DNA Example 6. Improving SDI Frequency by Reducing Vector Backbone Containing Events The transgenic plants created as described in Examples 1 and 2 were subjected to copy number and vector backbone analysis as shown in Table 6. The single copy event frequency for both split-marker T-DNA constructs is half that observed with the Control T-DNA configuration. Furthermore, over 75% of the transgenic events from the two split-marker T-DNA configurations (GmSMV1 and GmSMV2) had two or more copies of transgenes.

TABLE 6

Molecular analysis of transgene copy number and vector backbone presence

| Construct | Total sample # | 1 copy aadA (marker gene) | 2 copy aadA (marker gene) | Backbone vector positive |
|---|---|---|---|---|
| Control | 1670 | 46.80% | 29% | 20% |
| GmSMV1 | 336 | 23% | 29% | 59% |
| GmSMV2 | 336 | 22% | 20% | 46% |

These observations provide an opportunity to improve the frequency of targeted integration events by reducing or eliminating the vector backbone-containing events. Two strategies are described to reduce the occurrence of backbone-containing events.

A) Split marker vector with crtB cassette: It has previously been shown that expression of a non-lethal negative selectable marker, (e.g., crtB gene) in a binary vector backbone can significantly reduce backbone-containing event frequency (see Ye et al., *Transgenic Res.* 17:827-38 (2008); and U.S. Pat. No. 7,575,917; both of which are incorporated by reference here in their entireties). GmSMV3, a modified SMV1 vector was designed wherein an expression cassette comprising the crtB gene (SEQ ID NO: 36) was introduced into the vector backbone. GmSMV3 vector comprised a T-DNA construct which comprised, in 5' to 3' order, a truncated left border (tLB) sequence (SEQ ID NO:12); the 3' Marker cassette (SEQ ID NO: 11) in the forward orientation, an expression cassette for a Gene of Interest (GOI 2) under the control of a non-constitutive promoter; an expression cassette for a sequence encoding the Cas12a nuclease; an expression cassette for Cas12a gRNA targeting a GmTS2 target site within the soy genome; a first lox site; an expression cassette for a Gene of Interest 1 (GOI1) under the control of a constitutive promoter; a 27 nucleotide sequence encoding the GmTS2 target site; a spacer sequence (SEQ ID NO: 16); a second Lox site; the 5'Marker cassette (SEQ ID NO:10) in the forward orientation and a truncated Right Border (tRB) (SEQ ID NO: 13). The vector further comprised an expression cassette for the crtB gene operably linked to the Cauliflower Mosaic Virus 35S constitutive promoter that resided outside the T-DNA sequence. See FIG. 12A. Two controls were generated for this experiment. Control 1 was a standard control vector comprising a functional aadA marker cassette with a design similar to that described in Example 1. Control 2 was identical to GmSMV3 vector but lacked the crtB expression cassette.

Excised embryos from A3555 soybean plants were co-cultured with *Agrobacterium* comprising the GmSMV3 or control vectors and transformed plants were selected on spectinomycin medium for shoot elongation. The spectinomycin resistant shoots were transferred into soil plugs for rooting. DNA was extracted from leaf samples and used for copy number determination by TaqMan™ based assays. Flank PCR assays were used to identify plants with site directed integration of the T-DNA at the GmTS2 site. DNA from flanking PCR positive putative targeted events were further advanced for genome sequencing to confirm SDI and analyzed for presence of vector backbone. The results are summarized in Table 7 and 8.

TABLE 7

Summary of SDI construct transformation. TF indicates Transformation Frequency and Q SDI indicates Quality Site-Directed Integration Event.

| Construct | Split marker | CrtB cassette | Initial explants | Events in soil plugs | TF | Analyzed samples | Total SDI | Commercial quality SDI (QSDI) rate by plant No. | Commercial quality SDI rate in 2 copy events |
|---|---|---|---|---|---|---|---|---|---|
| Control 1 | − | − | 15000 | 504 | 3.3% | 336 | 3 | 0% (0/336) | 0.3% (1/336) |
| Control 2 | + | − | 15000 | 475 | 3.2% | 336 | 14 | 0.6% (2/336) | 0% (0/336) |
| GmSMV3 | + | + | 15000 | 314 | 2.0% | 227 | 7 | 0.4% (1/227) | 0.4% (1/227) |

TABLE 8

Molecular analysis of transgene copy number and vector backbone presence

| Construct | total | aadA 1 copy | aadA 2 copy | Backbone vector positive |
|---|---|---|---|---|
| Control 1 | 336 | 195 (58%) | 73 (22%) | 66 (17%) |
| Control 2 | 336 | 80 (23.8%) | 124 (37%) | 218 (65%) |
| GmSMV3 | 227 | 23 (10%) | 87 (38%) | 31 (9%) |

As shown in Table 8, the presence of the crtB cassette in GmSMV3 resulted in a significant reduction in backbone positive events.

B) Overlapping marker vector: The second strategy is to introduce an overlapping marker fragment at one end of the T-DNA, for example, adjacent to the RB (see FIG. 12B, partial marker). This fragment shows homology to the marker gene present adjacent to the LB (See FIG. 12B). Direct end joining of the T-DNA does not result in a functional marker gene cassette, and the single copy insert or multiple copy stacking does not express a functional marker gene to allow plant regeneration under selection. Regenerated plants can only be generated from events where homologous recombination occurs between the overlapping marker fragments resulting in a reconstituted functional marker.

A GmSMV4 T-DNA vector was designed which comprised, in 5' to 3' order, a truncated left border (tLB) sequence (SEQ ID NO:12); the 3' aadA Marker cassette (SEQ ID NO: 11) in the forward orientation, an expression cassette for a Gene of Interest (GOI 2) under the control of a non-constitutive promoter; an expression cassette for a sequence encoding the Cas12a nuclease; an expression cassette for Cas12a gRNA targeting a GmTS3 target site within the soy genome; a first lox site; an expression cassette for a Gene of Interest 1 under the control of a constitutive promoter; a 27 nucleotide sequence encoding the GmTS2 target site; a spacer sequence (SEQ ID NO: 16); a second Lox site; the 5'aadA Marker cassette (SEQ ID NO:10) in the forward orientation; a sequence (SEQ ID NO: 25) comprising a partial fragment of the 3'aadA Marker cassette in the forward orientation and a truncated Right Border (tRB) (SEQ ID NO: 13). SEQ ID NO: 25 is a 944 bp sequence comprising the 3' Arabidopsis Actin intron fused to a 5' CDS fragment from the aadA marker and shows homology to the 3'aadA marker cassette present adjacent to the LB. A control vector identical to GmSMV4 but lacking the partial 3' marker cassette fragment (SEQ ID NO 25) was also generated.

Excised embryos from A3555 soybean plants were co-cultured with *Agrobacterium* comprising the GmSMV4 or the control vectors and transformed plants were selected on spectinomycin medium for shoot elongation. The spectinomycin resistant shoots were transferred into soil plugs for rooting. DNA was extracted from leaf samples and used for copy number determination by TaqMan™ based assays. Flank PCR assays were used to identify plants with site directed integration of the T-DNA at the GmTS2 site. DNA from flanking PCR positive putative targeted events were further advanced for genome sequencing to confirm SDI and analyzed for presence of vector backbone. The results are summarized in Table 9 and 10. As shown in Table 10, the presence of the partial 3' aadA marker cassette adjacent to the RB resulted in a reduction in backbone vector positive events.

Example 8. Using Cre/Lox to Make Targeted Insertions

This example describes the design and testing of a Cre-Circle T-DNA vector comprising Cre/lox recombinase system expected to induce T-DNA circularization and targeted insertions of donor DNA at the *Zea mays* ZmTS1 genomic region.

Figure 6:
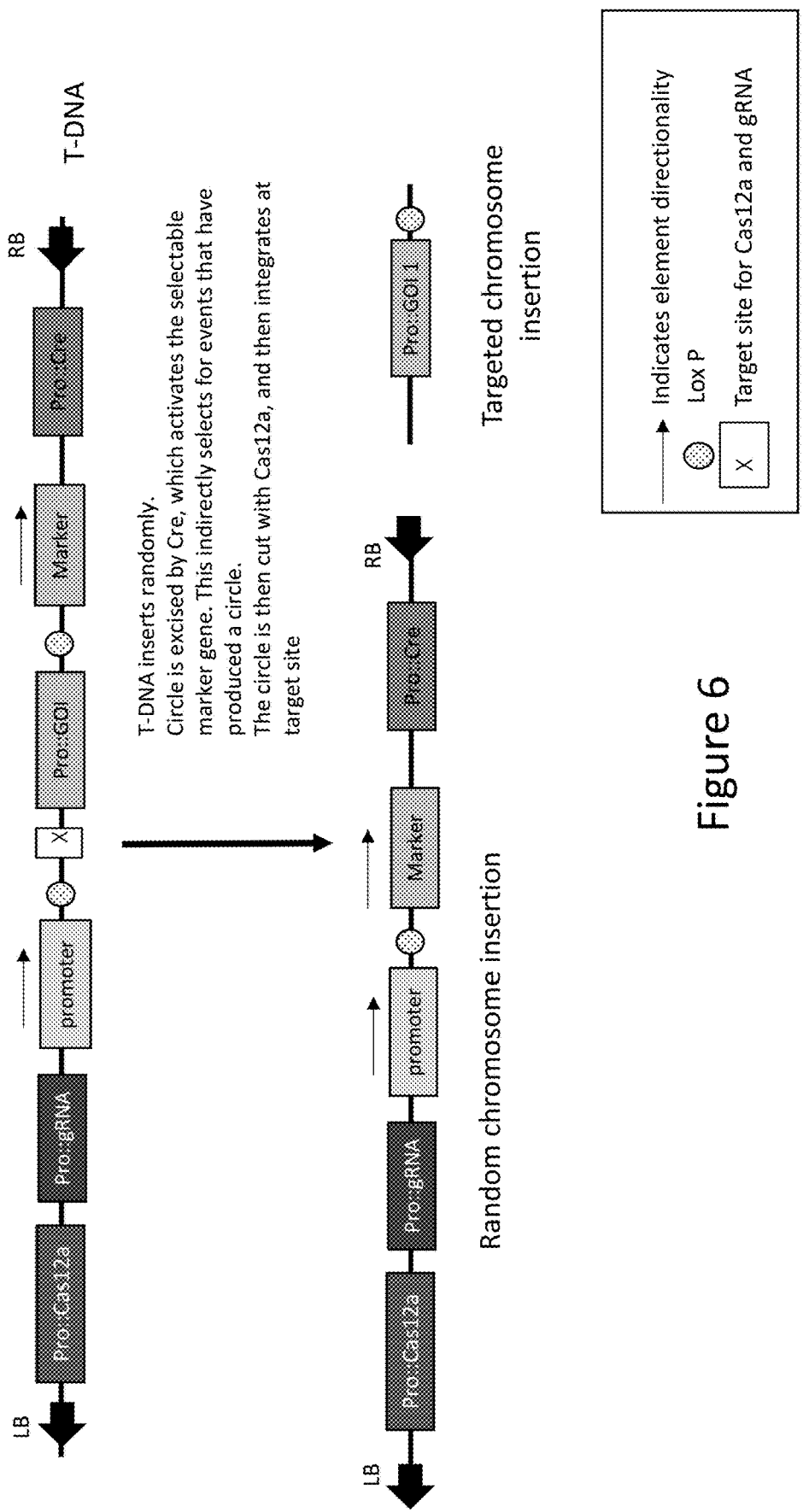
FIG. 6 depicts a schematic illustrating configuration of an *Agrobacterium* T-DNA vector designed to produce circular substrates in vivo by Cre/lox recombination. Cre mediated excision of the donor cassette from the T-DNA activates marker gene expression. This indirectly promotes selection of events where the segment comprising the donor has circularized. LB and RB indicate the left border and right border sequences of the T-DNA. Pro=Promoter; GOI=Gene of Interest. Horizontal arrows indicate the directionality of an element when directionality is critical.

A T-DNA construct was produced that comprised, in 5' to 3' order, a left border (LB) sequence; a nuclease cassette (SEQ ID NO: 26) comprising a promoter operably linked to a sequence encoding Cas12a; a guide RNA cassette comprising a Polymerase III promoter operably linked to a sequence encoding a guide RNA targeting ZmTS1; a Rice actin promoter (SEQ ID NO: 18), leader (SEQ ID NO:19), and intron sequence (SEQ ID NO: 20) in forward orientation; a first lox site; ZmTS1 Cas12a target site; a promoter operably linked to a sequence encoding a gene of interest; a second lox site; a sequence encoding the selectable marker CP4 gene cassette in forward orientation comprising a nucleotide sequence encoding the *Arabidopsis* EPSPS transit peptide (SEQ ID NO: 7) followed by the coding sequence for the *Agrobacterium* EPSPS-CP4 reporter gene (SEQ ID NO: 21) and a transcription termination sequence from the *Agrobacterium* nos gene (SEQ ID NO: 9); a recombinase cassette comprising a Rice Actin promoter (SEQ ID NO: 18), leader (SEQ ID NO:19) and intron (SEQ ID NO: 20) operably linked to a sequence encoding a Cre recombinase (SEQ ID NO 13 in WO2021026165); and a right border (RB) sequence. See FIG. 6.

TABLE 9

Summary of SDI construct transformation. TF indicates Transformation Frequency and Q SDI indicates Quality Site-Directed Integration Event.

| Construct | Partial 3' marker | Events in soil plugs | TF | Analyzed samples | Total SDI | Commercial quality SDI (QSDI) rate by plant No. | Commercial quality SDI rate in 2 copy events |
|---|---|---|---|---|---|---|---|
| Control | − | 470 | 4.2% | 336 | 2 | 0 | 0 |
| GmSMV4 | + | 401 | 3.58% | 330 | 1 | 0 | 0 |

TABLE 10

Molecular analysis of transgene copy number and vector backbone presence

| Construct | Analyzed samples | aadA 1 copy | aadA 2 copy | Backbone vector positive |
|---|---|---|---|---|
| Control | 336 | 130 (39%) | 98 (29%) | 235 (70%) |
| GmSMV4 | 330 | 132 (40%) | 89 (27%) | 154 (46%) |

Example 7. SDI by Homologous Recombination

Figure 13:
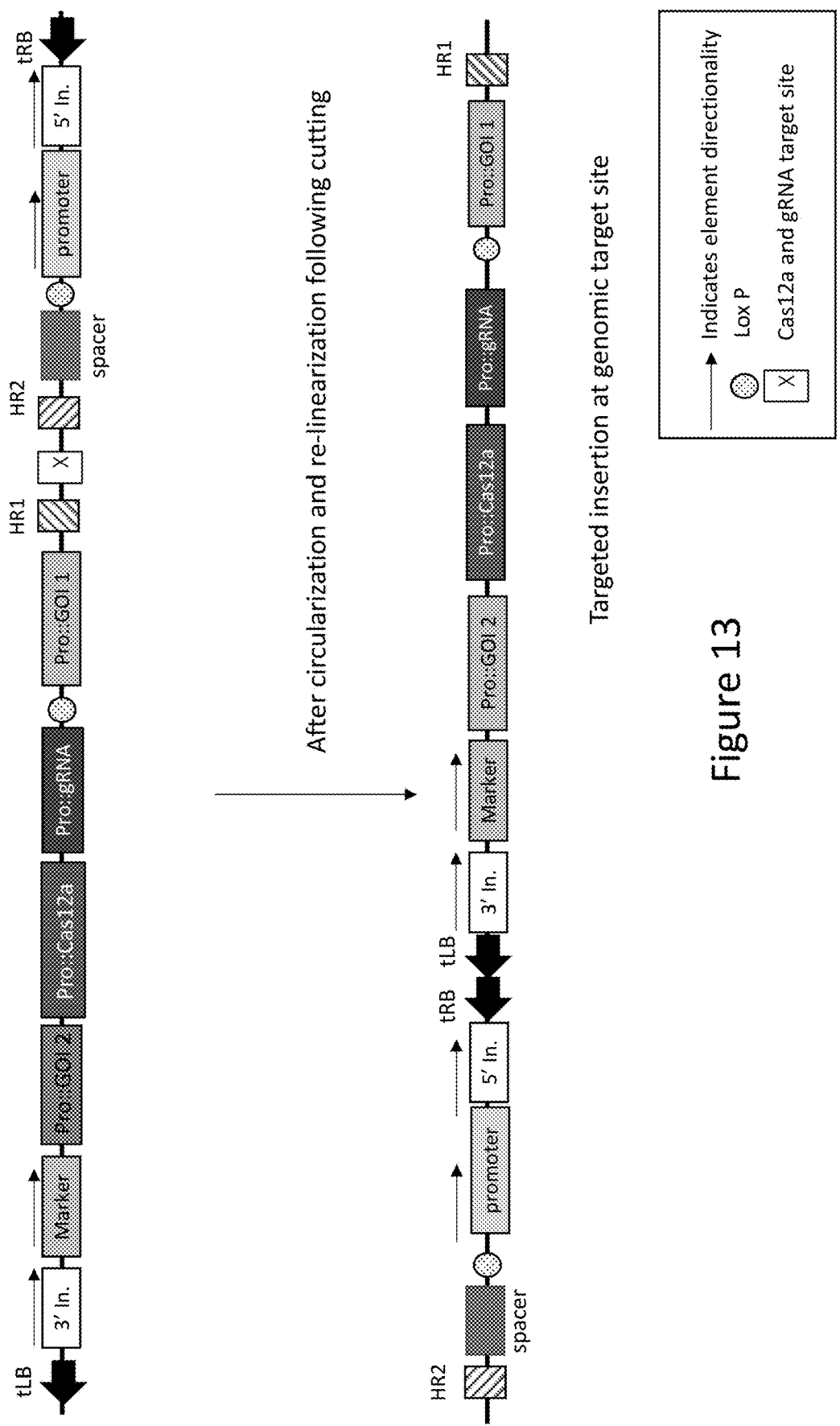
FIG. 13 depicts a schematic illustrating configuration of a vector for directional site-directed integration by homologous recombination. HR1: homology arm 1, HR2: homology arm 2.

The circular T-DNA and split marker configuration may also be used for homologous recombination directed integration as depicted in FIG. 13. Two homology arms homologous to the genomic target site are inserted between GOI and the marker gene promoter. An internal cutting site is located between the homologous arms. After T-DNA circularization and re-linearization in plant cells, the exposed homology arms (HR1 and HR2) at both ends promotes homologous recombination between the GOI and the genomic target site. The backbone reduction strategy described in FIG. 12A and Example 6 may be included to further improve the homologous recombination frequency.

Without being bound by any particular theory, it is hypothesized that once the construct is introduced to a plant cell via *Agrobacterium*-mediated transformation, the T-DNA inserts randomly in the genome of the plant cell and expression of Cre recombinase excises and circularizes a fragment of the T-DNA comprising the Cas12a target site and the promoter operably linked to a sequence encoding a gene of interest. This excision then allows the promoter to drive expression of the selectable marker gene at the random chromosome insertion site, allowing for selection of events that have undergone this circularization. Cas12a cleaves the circularized T-DNA fragment, and a target site in the genome allowing the GOI to integrate at the targeted chromosomal location.

Corn 01DKD2 cultivar embryos were transformed with *Agrobacterium* containing the Cre Circle T-DNA vector using methods known in the art. Stably transformed plants were selected on glyphosate. Leaf samples from regenerated plantlets were harvested after two weeks, and genomic DNA was extracted for copy number determination by TaqMan based assays, which are known in the art. Flank PCR assays were used to identify plants with site directed integration of the GOI at the ZmTS1 site. DNA from flanking PCR positive putative targeted events were further advanced for genome sequencing to confirm SDI and rates of commercial quality SDI. The results as summarized in Table 11 show that 3 SDI events were observed with Cre Circle T-DNA of which 1 was a Commercial Quality SDI event.

TABLE 11

Summary of SDI construct transformation. TF indicates Transformation Frequency and Q SDI indicates Quality Site-Directed Integration Event.

| Construct | Initial explants | Events in soil plugs | TF | Analyzed samples | Total SDI | Commercial quality SDI (QSDI) rate by plant No. | Commercial quality SDI rate in 2 copy events |
|---|---|---|---|---|---|---|---|
| Cre Circle 1 | 11200 | 336 | 0.76% | 336 | 3 | 1 | 2 |

Example 9. Using Cre/Lox to Make Targeted Insertions

Figure 7:
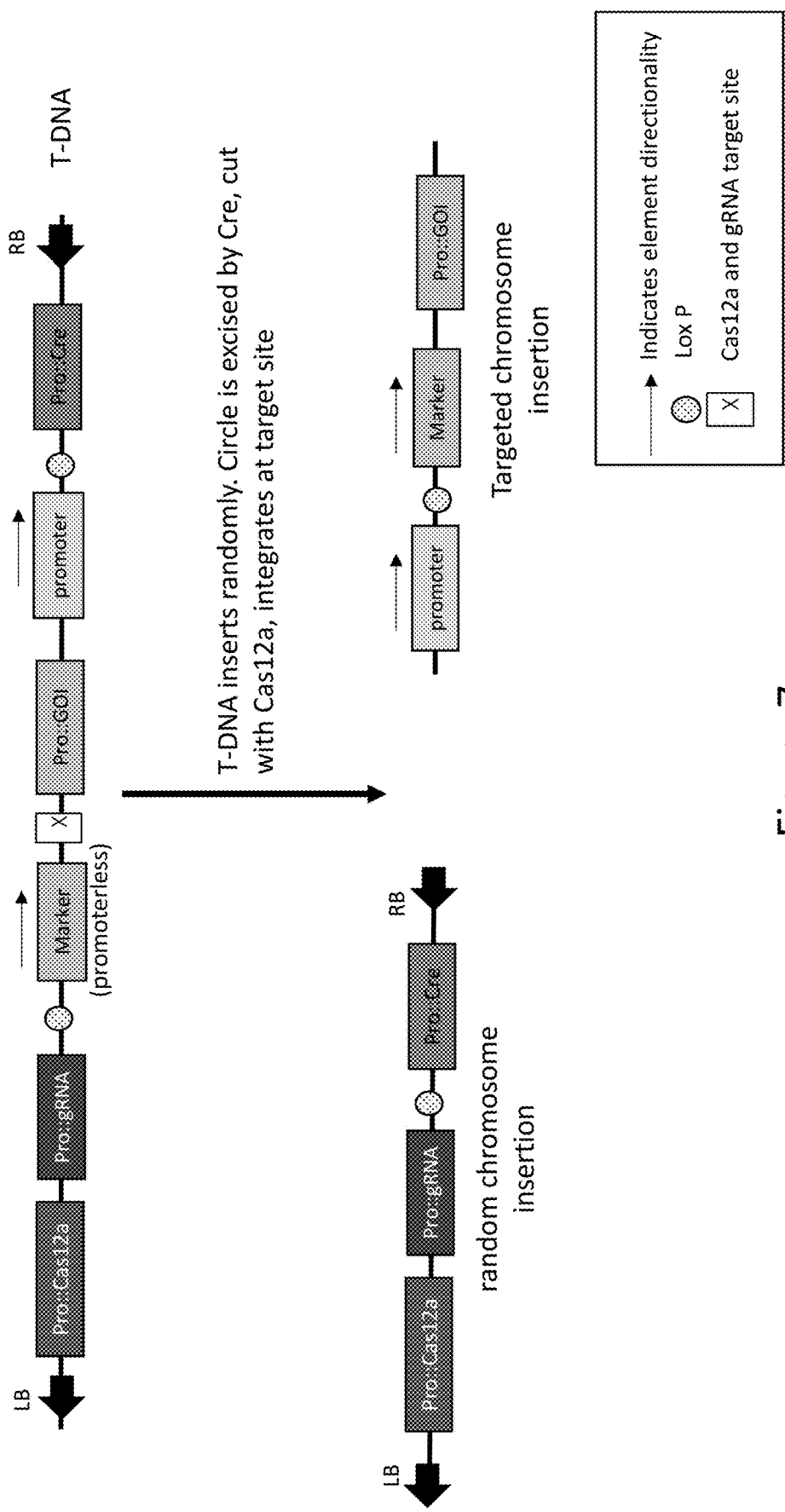
FIG. 7 depicts a schematic illustrating configuration of an *Agrobacterium* T-DNA vector designed to produce circular substrates in vivo by Cre/lox recombination, to promote targeted integration of a GOI cassette and a marker cassette at a genomic locus. LB and RB indicate the left border and right border sequences of the T-DNA. Pro=Promoter; GOI=Gene of Interest.

A T-DNA construct is produced that comprises, in 5' to 3' order, a left border (LB) sequence; a promoter operably linked to a sequence encoding Cas12a; a promoter operably linked to a sequence encoding a guide RNA; a first lox site, a sequence encoding a selectable marker gene in forward orientation; a Cas12a target site, a promoter operably linked to a sequence encoding a gene of interest; a promoter in forward orientation; a second lox site; a promoter operably linked to a sequence encoding a Cre recombinase; and a right border (RB) sequence. See FIG. 7.

The construct is introduced to a plant cell via *Agrobacterium*-mediated transformation, and the T-DNA inserts randomly in the genome of the plant cell. Once Cre recombinase is expressed, it excises and circularizes a fragment of the T-DNA comprising the promoter, the second lox site, the sequence encoding a selectable marker gene, the promoter operably linked to a sequence encoding a gene of interest, and the Cas12a target site. This excision then allows the promoter to drive expression of the selectable marker gene, allowing for selection of events that have undergone this circularization. Cas12a cleaves the circularized T-DNA fragment and a target site in the genome, allowing the promoter in forward orientation, the selectable marker gene, and the promoter operably linked to a sequence encoding a gene of interest to integrate at the targeted chromosomal location.

Example 10. Using Cre/Lox to Make Targeted Insertions

Figure 8A:
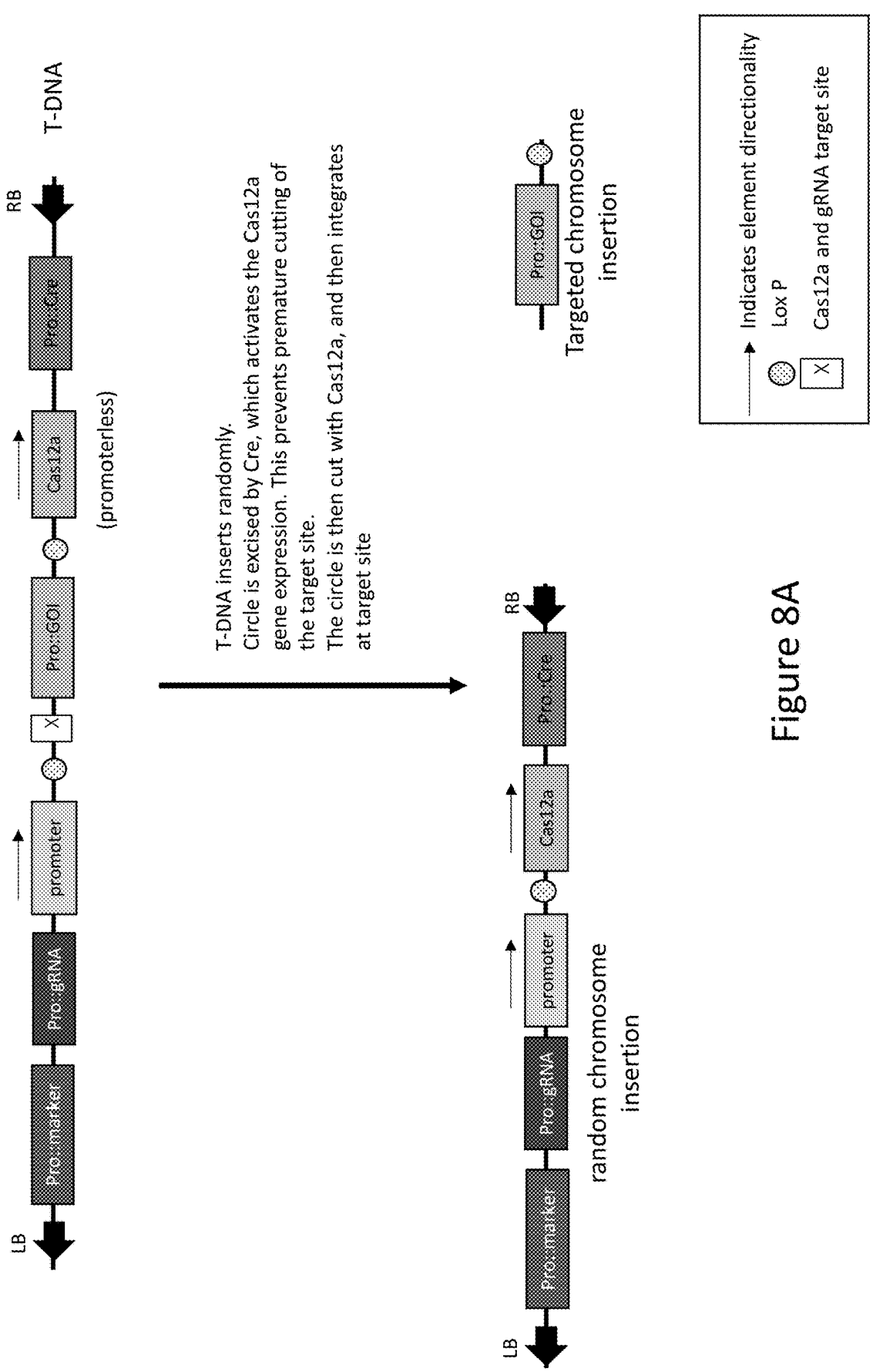
FIG. 8A and FIG. 8B depict a schematic illustrating two configurations of an *Agrobacterium* T-DNA vector designed to produce circular substrates in vivo by Cre/lox recombination system to promote targeted integration of a GOI cassette at a genomic locus. Cre-mediated excision of the P::GOI cassette activates LbCas12a gene expression. LB and RB indicate the left border and right border sequences of the T-DNA. Pro=Promoter; GOI=Gene of Interest. Horizontal arrows indicate the directionality of an element when directionality is critical.

A T-DNA is produced that comprises, in 5' to 3' order, a left border (LB) sequence; a promoter operably linked to a sequence encoding a selectable marker gene; a Polymerase III promoter operably linked to a sequence encoding a Cas12a guide RNA; a promoter in forward orientation; a first lox site; a Cas12a target site; a promoter operably linked to a sequence encoding a gene of interest; a second lox site, a sequence encoding Cas12a in forward orientation; a promoter operably linked to a sequence encoding Cre recombinase; and a right border (RB) sequence. See FIG. 8a.

The construct is introduced into plant cells via *Agrobacterium*-mediated transformation, and the T-DNA inserts randomly in the genome of the plant cell. Cre recombinase is expressed and excises and circularizes a fragment of the T-DNA comprising the Cas12a target site and the promoter operably linked to a sequence encoding a gene of interest. After the Cre recombinase mediated excision, the promoter is operably linked to the sequence encoding Cas12a. Expression of Cas12a allows the circularized T-DNA fragment to be cut as well as cleavage of the target site in the genome, thereby allowing the gene of interest to integrate at the targeted chromosome location.

Figure 8B:
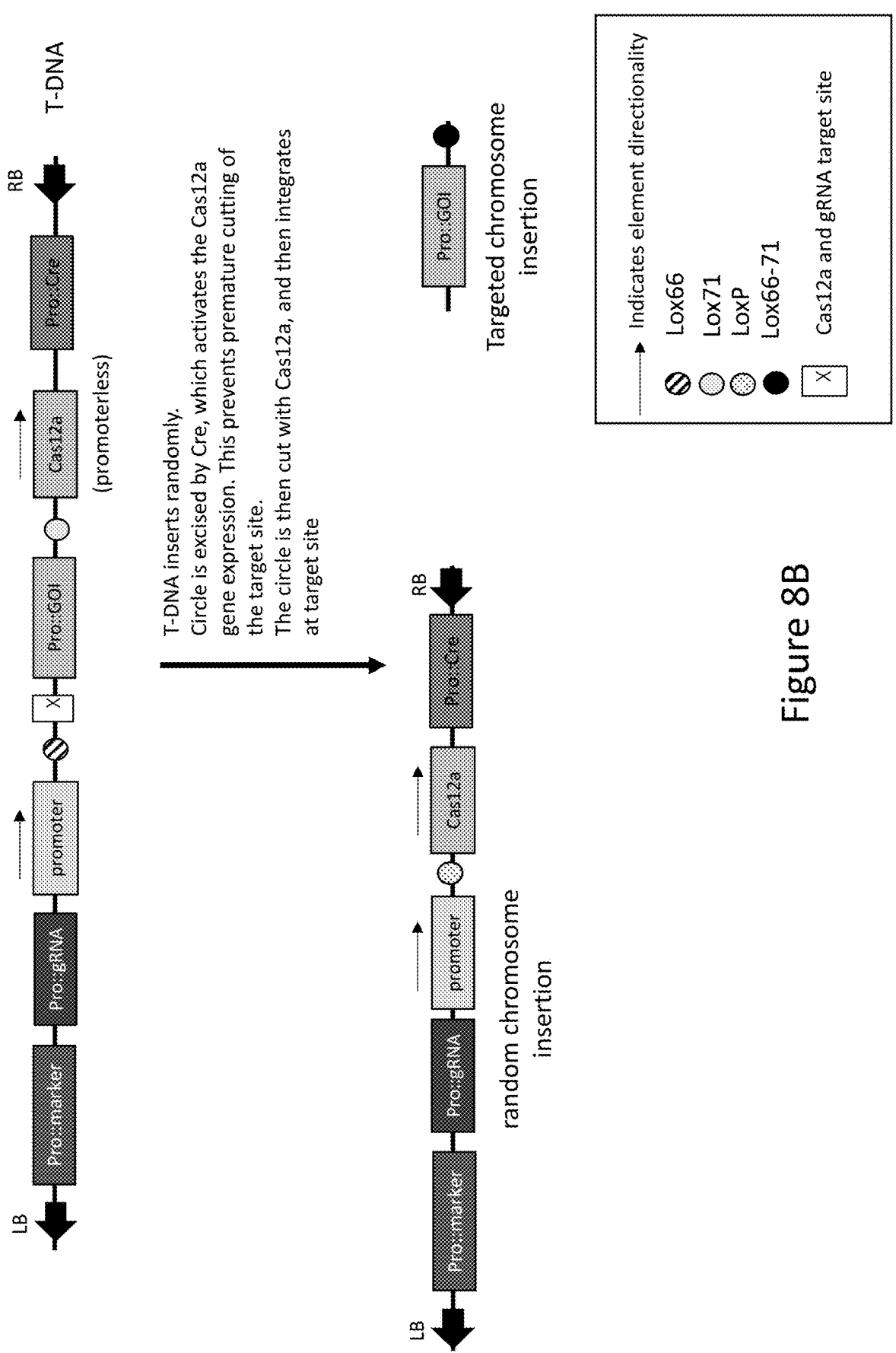

A T-DNA is produced that comprises, in 5' to 3' order, a left border (LB) sequence; a promoter operably linked to a sequence encoding a selectable marker; a promoter operably linked to a sequence encoding a Cas12a guide RNA; a promoter in forward orientation; a lox66 site; a Cas12a target site; a gene of interest; a lox71 site, a sequence encoding Cas12a in forward orientation; a promoter operably linked to a sequence encoding Cre recombinase; and a right border (RB) sequence. See FIG. 8b.

The construct is introduced into plant cells via *Agrobacterium*-mediated transformation, and the T-DNA inserts randomly in the genome of the plant cell. Following expression of Cre recombinase, it excises and circularizes a fragment of the T-DNA comprising the Cas12a target site and the gene of interest. After the excision, the promoter in forward orientation can drive the expression of Cas12a at the random chromosome insertion site. The expression of Cas12a allows the circularized T-DNA fragment to be cut as well as cleave the target site in the genome, thereby allowing the gene of interest to integrate at the targeted chromosome location. The purpose of using modified lox sites in the T-DNA construct is to produce a plant in which a mutant lox site (lox66-71) in the final targeted chromosome insertion is unable to recombine with the lox site (loxP) in the randomly integrated T-DNA thus avoiding unwanted chromosomal rearrangements between the targeted event comprising the gene of interest and the randomly integrated T-DNA.

Example 11. Using Cre/Lox to Make Targeted Insertions

Figure 9:
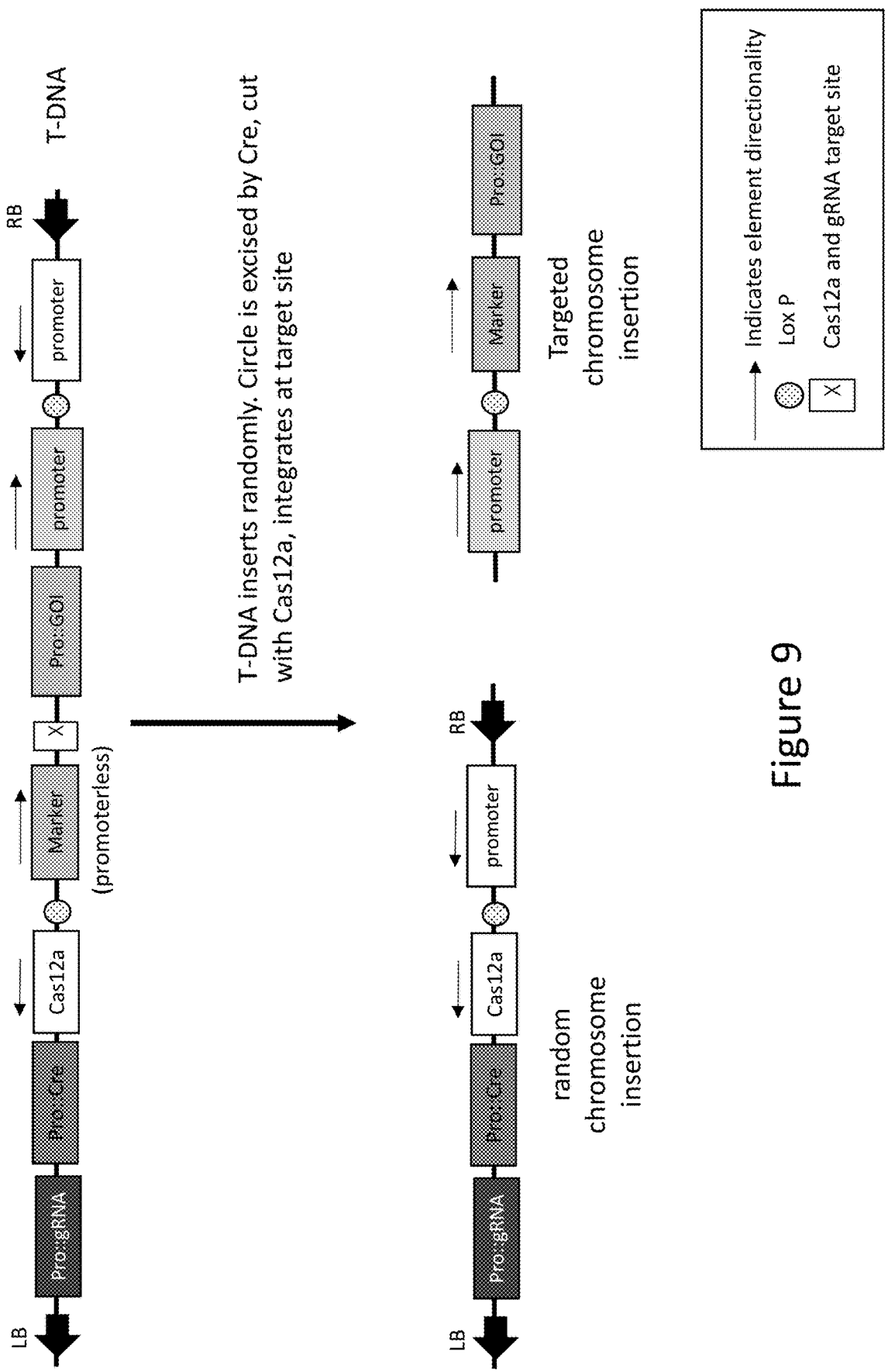
FIG. 9 depicts a schematic illustrating configuration of an *Agrobacterium* T-DNA vector designed to produce circular substrates by Cre/lox recombination to promote targeted integration of a GOI cassette and a marker cassette at a genomic locus. LB and RB indicate the left border and right border sequences of the T-DNA. Pro=Promoter; GOI=Gene of Interest. Horizontal arrows indicate the directionality of an element when directionality is critical.

A T-DNA construct is produced that comprises, in 5' to 3' order, a left border (LB) sequence; a promoter operably linked to a Cas12a guide RNA; a promoter operably linked to a sequence encoding a Cre recombinase; a sequence encoding Cas12a in reverse orientation; a first lox site; a sequence encoding a selectable marker in forward orientation; a Cas12a target site; a gene of interest; a promoter in forward orientation; a second lox site; a promoter in reverse orientation; and a right border (RB) sequence. See FIG. 9.

The construct is introduced to a plant cell via *Agrobacterium*-mediated transformation, and the T-DNA inserts randomly in the genome of the plant cell. Following expression, Cre recombinase excises and circularizes a fragment of the T-DNA comprising the promoter in forward orientation, the sequence encoding a selectable marker gene in forward orientation, and the gene of interest. After the excision, the promoter is operably linked to the sequence encoding Cas12a. The expression of Cas12a allows cleavage of a genomic target site. It also allows the circularized T-DNA fragment to be cut, thereby allowing the promoter in forward orientation driving expression of the sequence encoding the selectable marker gene and the gene of interest to integrate at the targeted chromosomal location. A T-DNA provided in this configuration limits Cas12a expression to after excision of the sequence flanked by the recombination sites, and expression of the selectable marker gene allows selection of events that have undergone circularization.

Example 12. 2T Constructs

Figure 10:
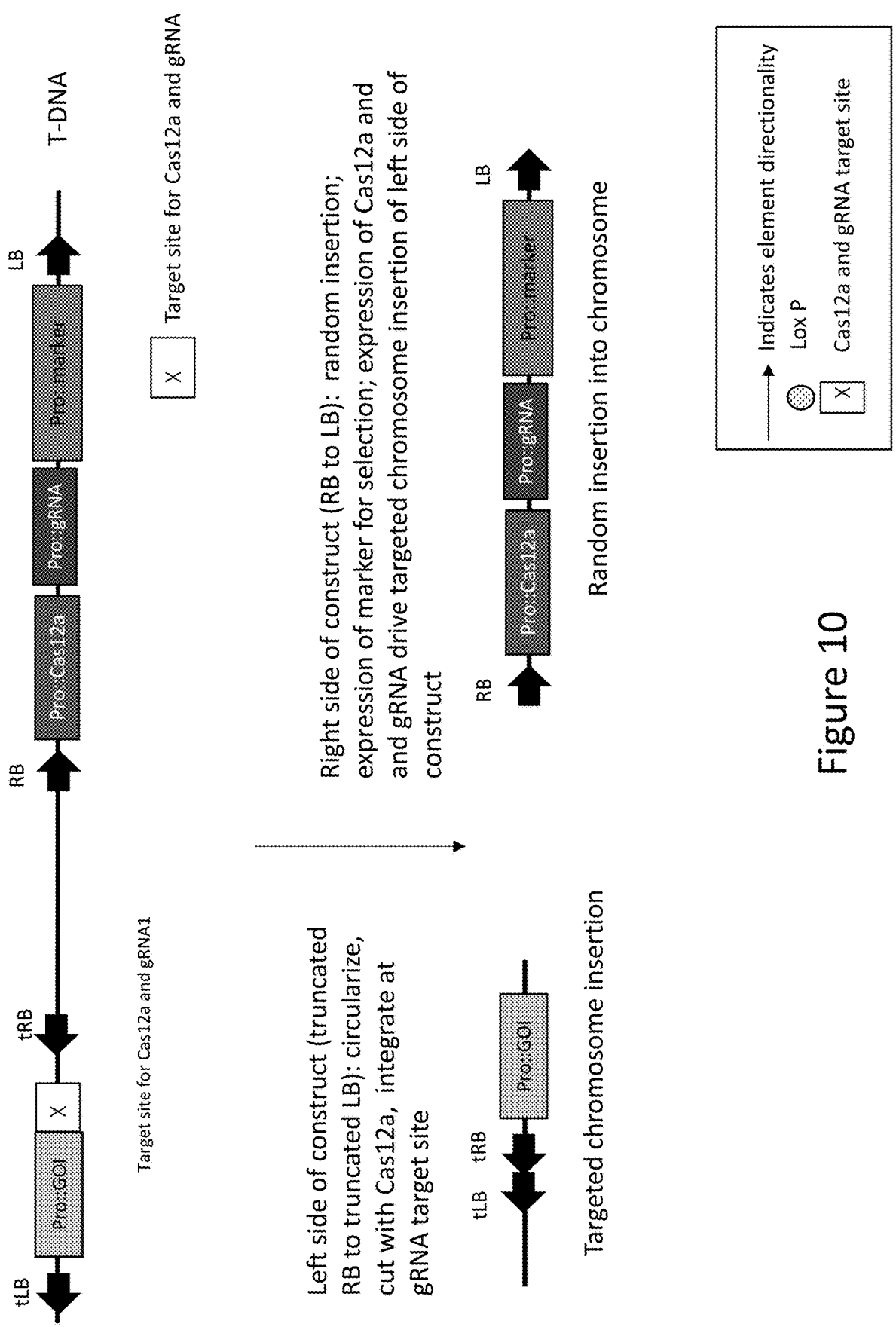
FIG. 10 depicts a schematic illustrating configuration of a vector comprising two separate T-DNA regions, one comprising a PRO::GOI1 cassettes that is flanked by RB and LB elements, which may or may not be truncated as in FIG. 3 and a target site for a CRISPR nucleases; and a second T-DNA region comprising cassettes for expression of CRISPR nuclease, a gRNA, and a selectable marker gene

To reduce inefficiency caused by excision frequency, a "2T" construct can be employed. See FIG. 10. In general, 2T constructs comprise two T-DNAs which are independently integrated into the genome. They are subcloned into a single construct in apposition (in most cases, with right borders near each other and in opposite directions in order to maximize the likelihood of independent T-DNA strand production). In random insertion experiments, as many as 30% of recovered plants have integrations of each of the T-DNAs. In *Agrobacterium*, the right side of the construct (see FIG. 10) produces a T-DNA strand (#1) that can be randomly integrated and contains all the machinery necessary for SDI, including an expression cassette for LbCas12a, an expression cassette for a gRNA, and an expression cassette for a selection marker. The left side of the construct (see FIG. 10) produces a T-DNA strand (#2) that minimally contains: RB and LB elements (often of shortened length to minimize the non-cargo sequence in the final insertion), a target site for a guided buclease, and one or more cargo element(s). In some cases, the cargo is an expression cassette for a gene of interest (GOI), but more complex designs, for example, designs with multiple elements are possible. Upon circularization, strand #2 is competent for SDI at the target location in the genome. Plants are selected based on the marker in a T-DNA #1 insertion and can be assayed for the presence of T-DNA #2 at the target location in the genome. Assuming the random integration of T-DNA #1 occurs at a distance greater than 100 cM from the target site, removal of the SDI machinery may be accomplished by simple segregation at high frequency. This method avoids the use of Cre-lox or other recombination schemes to remove the unwanted machinery in the plant.

This method is compatible with the use of multiple gRNAs as detailed in FIG. 5. Addition of that strategy to this method involves providing a novel target site in T-DNA #2 and expressing two gRNAs from T-DNA #1, one targeting the genomic site and the other targeting the novel site present in T-DNA #2. Use of the combined strategy can result in a higher efficiency of targeted insertion of T-DNA strand #2.

Example 13. Two-T-DNA Strategy

Figure 11:
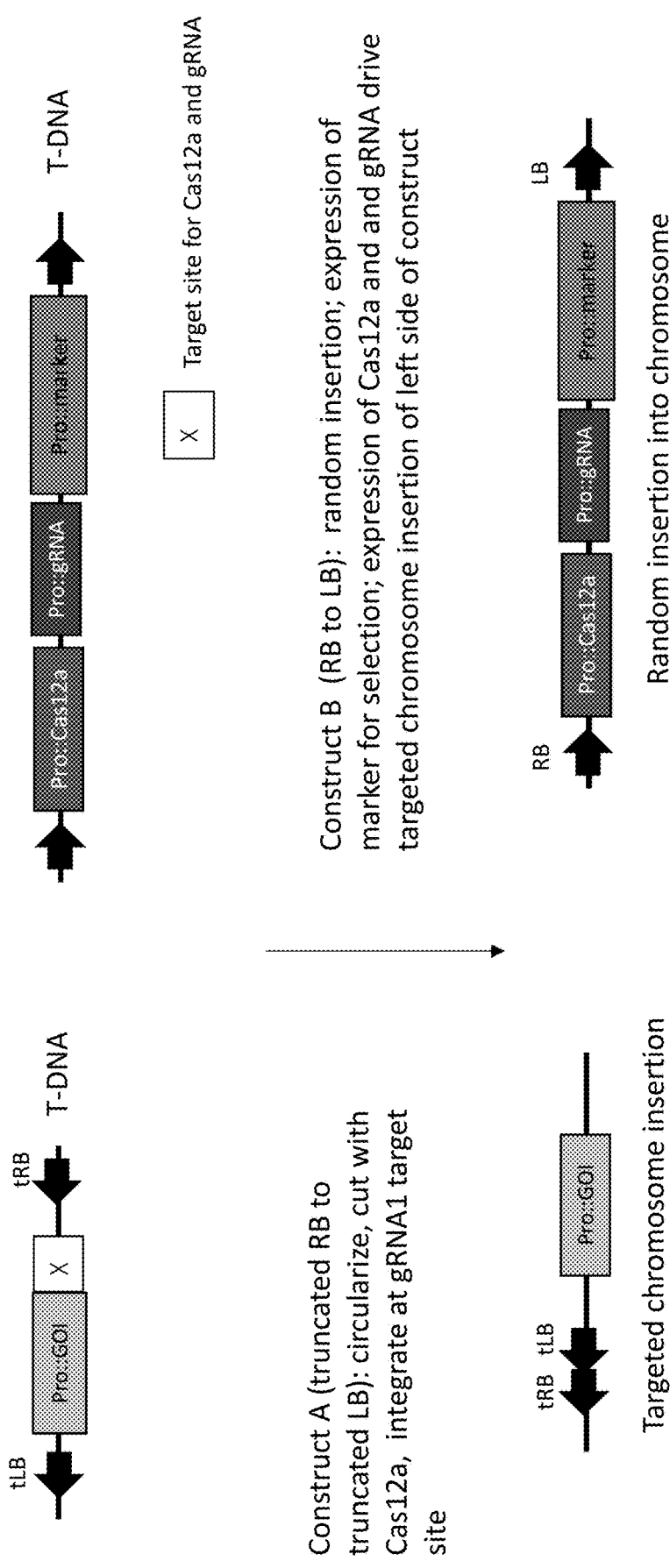
FIG. 11 depicts a schematic illustrating configuration of a vector comprising two separate T-DNA regions as in FIG. 10, except that in this embodiment the two separate T-DNA regions are on separate replicons.

An example of a two-T-DNA strategy for site directed integration of a gene of interest is depicted in FIG. 11. Two T-DNAs can be successfully co-introduced into plants by co-expression in *agrobacterium* using independent origins of replication. Origins currently in use are known to support different copy numbers in the *Agrobacterium*, so the choice of origins can be used to affect the ratio of the T-DNA strands introduced into the plant target, which can be used to optimize the frequency of desired final product. A two-T-DNA strategy also has the advantage of involving two smaller plasmids, which may be easier to subclone and maintain. Additionally, because the machinery for SDI can be provided on one plasmid, a limited number of plasmid designs comprising the guided nuclease are needed for optimization. Multiple constructs can be produced more easily (because of a shorter size) that contain coordinated target sites and differing cargos of interest.

In random insertion experiments, as many as 30% of recovered plants have integrations of each of the T-DNAs. In *Agrobacterium*, a first construct produces a first T-DNA that can be randomly integrated and contains the machinery necessary for SDI, including an expression cassette for LbCas12a, an expression cassette for the targeting gRNA and an expression cassette for a selectable marker. The second construct produces a second T-DNA that minimally contains: RB and LB elements (often of shortened length to minimize the non-cargo sequence in the final insertion); a target site; and the cargo element(s). In some cases, the cargo is a gene of interest (GOI), but more complex designs, and designs with multiple elements are possible. The second T-DNA may be inserted at the genomic target site through cleavage of a circularized intermediate as described above. Plants are selected based on the marker in a first T-DNA insertion and can be assayed for the presence of insertion of the second T-DNA at the genomic target site. Assuming the random integration of first T-DNA occurs at a distance greater than 100 cM from the genomic target site, removal of the first T-DNA (and the expression cassettes for the guided nuclease and selectable marker) may be accomplished by simple segregation. This method avoids the use of Cre-lox or other recombination schemes to remove the unwanted cassettes, which may be critical for plant systems in which those recombination strategies are inefficient.

This method is compatible with the use of multiple gRNAs, for example, as detailed in FIG. 5. Addition of the use of multiple gRNAs to this method involves utilizing a novel target site in the second T-DNA, and the expression of two gRNAs by the first T-DNA, one targeting the genomic target site and the other targeting the novel target site present in the second T-DNA. Use of the combined strategy can result in a higher efficiency of targeted insertion of the second T-DNA into the genome.

Example 14. Design of a Binary Construct

This example describes the design of a construct with two gRNAs expressed from the T-DNA: one targeting a unique target site in the T-DNA and the second targeting the GmTS1 target site in the genome (SEQ ID NO: 61) (see e.g., FIG. 5).

A gRNA spacer sequence targeting GmTS1 target site within the soy chromosome was designed. Two T-DNA target sites were designed to promote microhomology assisted annealing with the genomic target site (See Table 12). In the first design ("GmTS1-RC"), the T-DNA target site was a 27 bp sequence comprising a 4 bp PAM and a 23 bp spacer sequence (SEQ ID NO: 62). Positions 1 to 19 in the spacer-complementary sequence are identical between genomic GmTS1 target site and T-DNA target site. However, positions 20 to 23 within the T-DNA target site are designed to be the reverse complement (RC) of positions 20 to 23 of the spacer-complementary sequence of the genomic target site to maximize the microhomology potential with the genomic strand.

For the second design, it was hypothesized that a unique target site present in the T-DNA might improve the rate of SDI if the sequences surrounding the unique T-DNA target site matched the sequence surrounding the chromosomal GmTS1 target site. Thus in the second design, the T-DNA target site (GmTS1-RC1+flanks) is a 91 bp sequence (SEQ ID NO: 63) comprising the GmTS1-RC target site described in design 1 flanked by a 26 bp left flank and 38 bp right flank sequence comprising the chromosomal sequence flanking the GmTS1 sequence in the soy genome.

TABLE 12

Soy Target sites and T-DNA target sequences. PAM sequence shown in italics. Four base pairs of reverse-complement design are shown in bold. Sequences flanking the GmTS1 and present in the T-DNA target site shown in lowercase.

| | Design | Target site | Target site sequence | SEQ ID NO |
|---|---|---|---|---|
| 1 | Genomic target site | GmTS1 | *TTT*AGACTTTAGCTCCTCTGTTGAGTC | 61 |
| 2 | T-DNA Target site Design 1 | GmTS1-RC | *TTT*AGACTTTAGCTCCTCTGTTGACT | 62 |
| 3 | T-DNA Target site Design 2 | GmTS1-RC + flanks | ttattatttattccttcgttctgtcT*TT*AGACTTTAGCTCCTCTGTTGGACTtaaacaacactacatctgacctaagaatgagcggccgc | 63 |

TABLE 13

Vectors comprising gRNA arrays. The control construct comprised a single guide RNA that targeted identical genomic and T-DNA target site.

| T-DNA vectors | gRNA1 (targeting genomic site) | gRNA 2 (targeting T-DNA site) | Orientation of T-DNA target site (with respect to the marker cassettes) |
|---|---|---|---|
| GmSMV5 | GmTS1 | GmTS1-RC | Forward |
| GmSMV6 | GmTS1 | GmTS1-RC + flanks | Forward |
| GmSMV7 | GmTS1 | GmTS1-RC + flanks | Reverse |
| GmSMV1 (control) | GmTS1 | NA | Forward |

3 T-DNA constructs were produced. GmSMV5 comprised, in 5' to 3' order, a truncated left border (tLB) sequence; a 3' marker cassette fragment (SEQ ID NO: 11) in forward orientation; a promoter operably linked to a sequence encoding Cas12a; a promoter operably linked to a sequence encoding a guide RNA array which comprises gRNA1 targeting GmTS1 on the chromosome and gRNA 2 targeting GmTS1-RC; a gene of interest 2, a lox site, a gene of interest 1, the GmTS1-RC target site (SEQ ID NO: 62) in the forward orientation, a second lox site, a 5' Marker cassette fragment (SEQ ID NO: 10) in the forward orientation; and a truncated right border (tRB) sequence. See FIG. 5.

GmSMV6 comprised, in 5' to 3' order, a truncated left border (tLB) sequence; a 3' marker cassette fragment (SEQ ID NO: 11) in forward orientation; a promoter operably linked to a sequence encoding Cas12a; a promoter operably linked to a sequence encoding a guide RNA array which comprises gRNA1 targeting GmTS1 on the chromosome and gRNA 2 targeting GmTS1-RC; a gene of interest 2, a lox site, a gene of interest 1, the 'GmTS1-RC+Flanks' target site (SEQ ID NO:63) in the forward orientation, a second lox site, a 5' Marker cassette fragment (SEQ ID NO: 10) in the forward orientation; and a truncated right border (tRB) sequence.

GmSMV7 comprised, in 5' to 3' order, a truncated left border (tLB) sequence; a 3' marker cassette fragment (SEQ ID NO: 11) in forward orientation; a promoter operably linked to a sequence encoding Cas12a; a promoter operably linked to a sequence encoding a guide RNA array which comprises gRNA1 targeting GmTS1 on the chromosome and gRNA 2 targeting GmTS1-RC; a gene of interest 2, a lox site, a gene of interest 1, the 'GmTS1-RC+Flanks' target site (SEQ ID NO:63) in the reverse orientation, a second lox site, a 5' Marker cassette fragment (SEQ ID NO: 10) in the forward orientation; and a truncated right border (tRB) sequence.

The constructs were introduced to plant cells via *Agrobacterium*-mediated transformation. GmSMV1, described in Example 2 was used as a control. Inside the plant cell, a subset of the T-DNA circularizes. Cas12a-gRNA2 complex cleaves the circularized T-DNA and Cas12a-gRNA1 complex cleaves the genomic target site. The T-DNA circularization and subsequent cleavage allows for targeted integration of the linear T-DNA into the genomic target site. Circularization and linearization also reconstitutes a spliceable intron within the marker cassette thus allowing the promoter to drive expression of the selectable marker gene, thus allowing for selection of events that have undergone circularization followed by T-DNA integration. Flank PCR assays and genomic DNA sequencing were carried out to identify plants with targeted integration events. The data is summarized in Table 14. A quality SDI event is defined as single copy insertion of T-DNA at the targeted site with intact cassettes and transgene/genome junction nearly as expected. The SDI rate is defined as the ratio of quality SDI events to samples. Quality SDI rate in 2 copy events indicates that these plants had 2 copies of the TDNA with at least 1 TDNA being a quality SDI insert. These plants would require segregation of progeny for single copy commercial quality SDI events.

As shown in Table 14, Commercial quality SDI events were generated from all the tested constructs. The highest Commercial Quality SDI rate (9.52%) was observed with the GmSMV6 construct comprising the 91 bp 'GmTS1-RC+ flanks' T-DNA target site in the forward orientation. GmSMV7 construct comprising the 91 bp 'GmTS1-RC+ flanks' TDNA target site in the reverse orientation also generated a high number of Commercial quality events and had a Q-SDI rate of 4.76%. Without being bound by any theory, it is hypothesized that a potential benefit of using the larger 91 bp target site with flanks is that the target site on the T-DNA is farther away from T-DNA elements both upstream and downstream that are required to be present in commercial quality events, allowing for greater likelihood of retention of their full sequences after SDI. A second potential benefit is that the flanks may promote spatial segregation of the T-DNA target sequence from other T-DNA sequences/elements, some of which might have a negative influence on the functionality of the target sequence.

The construct is introduced into plant cells via *Agrobacterium*-mediated transformation, and the T-DNA inserts randomly in the genome of the plant cell. Once Cre recombinase activates, it excises and circularizes a fragment of the T-DNA comprising the Cas12a target site and the gene of

TABLE 14

Summary of SDI construct transformation. TF indicates Transformation Frequency and Q SDI indicates Quality Site-Directed Integration Event.

| Construct | Initial explants | Events in soil plugs | TF | Analyzed samples | Total SDI | Commercial quality SDI rate by plant No. | Commercial quality SDI rate in 2 copy events | Combined SDI rate by plant No. | Potential commercial quality SDI rate by explants |
|---|---|---|---|---|---|---|---|---|---|
| GmSMV1 (control) | 11200 | 336 | 3.41 | 252 | 62 | 2.78% (7/252) | 1 | 3.17% (8/252) | 0.11% (12.1/11200) |
| GmSMV5 | 11200 | 336 | 3.69 | 252 | 56 | 1.59% (4/252) | 0 | 1.59% (4/252) | 0.59% (6.6/11200) |
| GmSMV6 | 11200 | 420 | 3.75 | 83 | 36 | 9.52% (8/84) | 0 | 9.52% (8/84) | 0.36% (17.3/11200) |
| GmSMV7 | 11200 | 363 | 3.23 | 84 | 34 | 4.76% (4/84) | 0 | 4.76% (4/84) | 0.15% (17.3/11200) |

Example 15. Using Cre/Lox to Make Targeted Insertions

Figure 19:
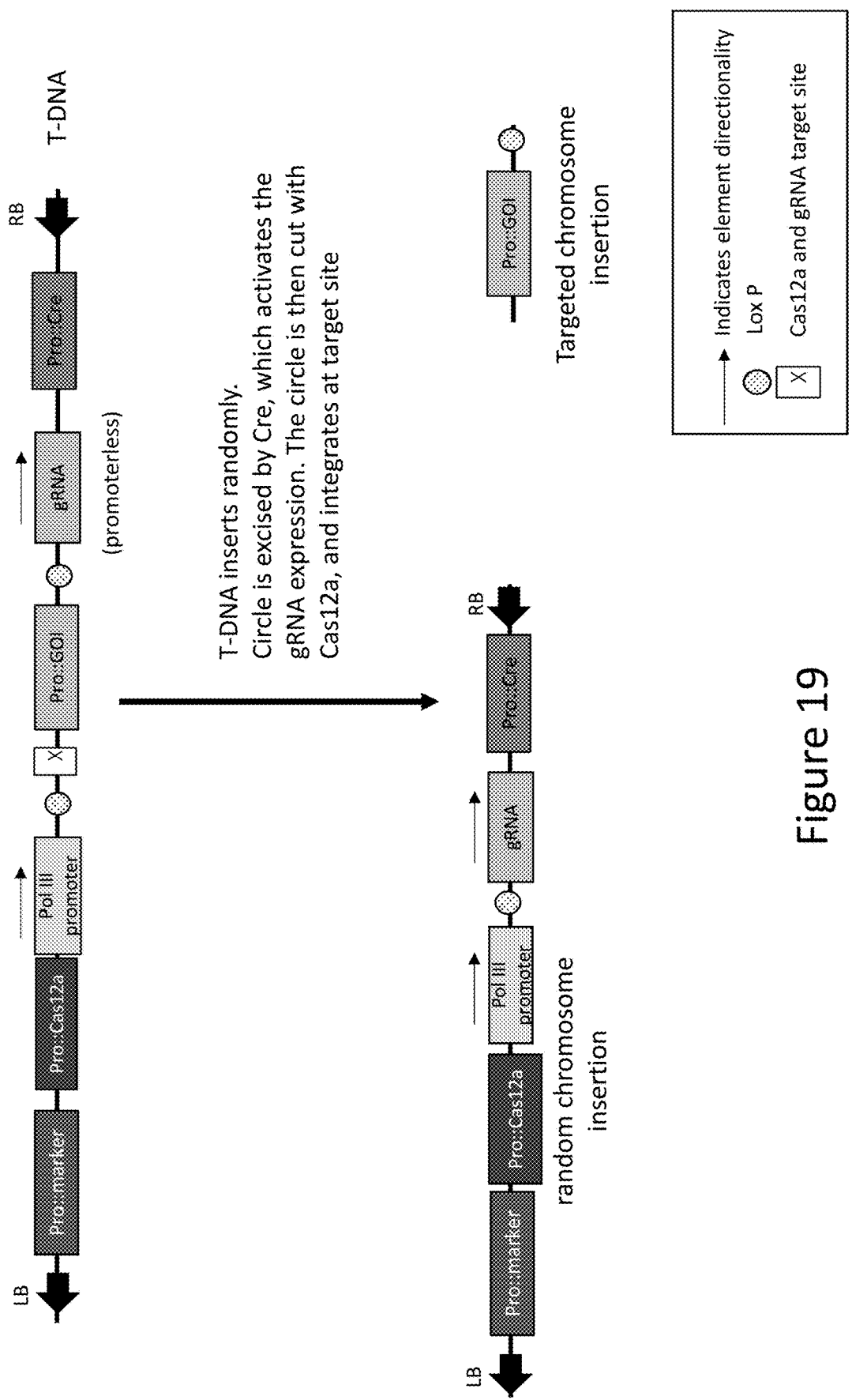
FIG. 19: depicts a schematic illustrating configuration of an *Agrobacterium* T-DNA vector designed to produce circular substrates in vivo by Cre/lox recombination system to promote targeted integration of a GOI cassette at a genomic locus. Cre-mediated excision of the P::GOI cassette activates the gRNA expression. LB and RB indicate the left border and right border sequences of the T-DNA. Pro=Promoter; GOI=Gene of Interest. Horizontal arrows indicate the directionality of an element when directionality is critical.

A T-DNA is produced that comprises, in 5' to 3' order, a left border (LB) sequence; a promoter operably linked to a sequence encoding a selectable marker gene; a promoter operably linked to a sequence encoding a Cas12a nuclease; a Polymerase III promoter in forward orientation; a first lox site; a Cas12a target site; a gene of interest; a second lox site, a sequence encoding a guide RNA in forward orientation; a promoter operably linked to a sequence encoding Cre recombinase; and a right border (RB) sequence. See FIG. 19.

The construct is introduced into plant cells via *Agrobacterium*-mediated transformation, and the T-DNA inserts randomly in the genome of the plant cell. Once Cre recombinase activates, it excises and circularizes a fragment of the T-DNA comprising the Cas12a target site and the promoter operably linked to a sequence encoding a gene of interest. After the excision, the Polymerase III promoter in forward orientation can drive the expression of guide RNA at the random chromosome insertion site. The expression of Cas12a and gRNA allows the circularized T-DNA fragment to be cut as well as cleave the target site in the genome, thereby allowing the promoter operably linked to a sequence encoding a gene of interest to integrate at the targeted chromosome location.

Figure 20:
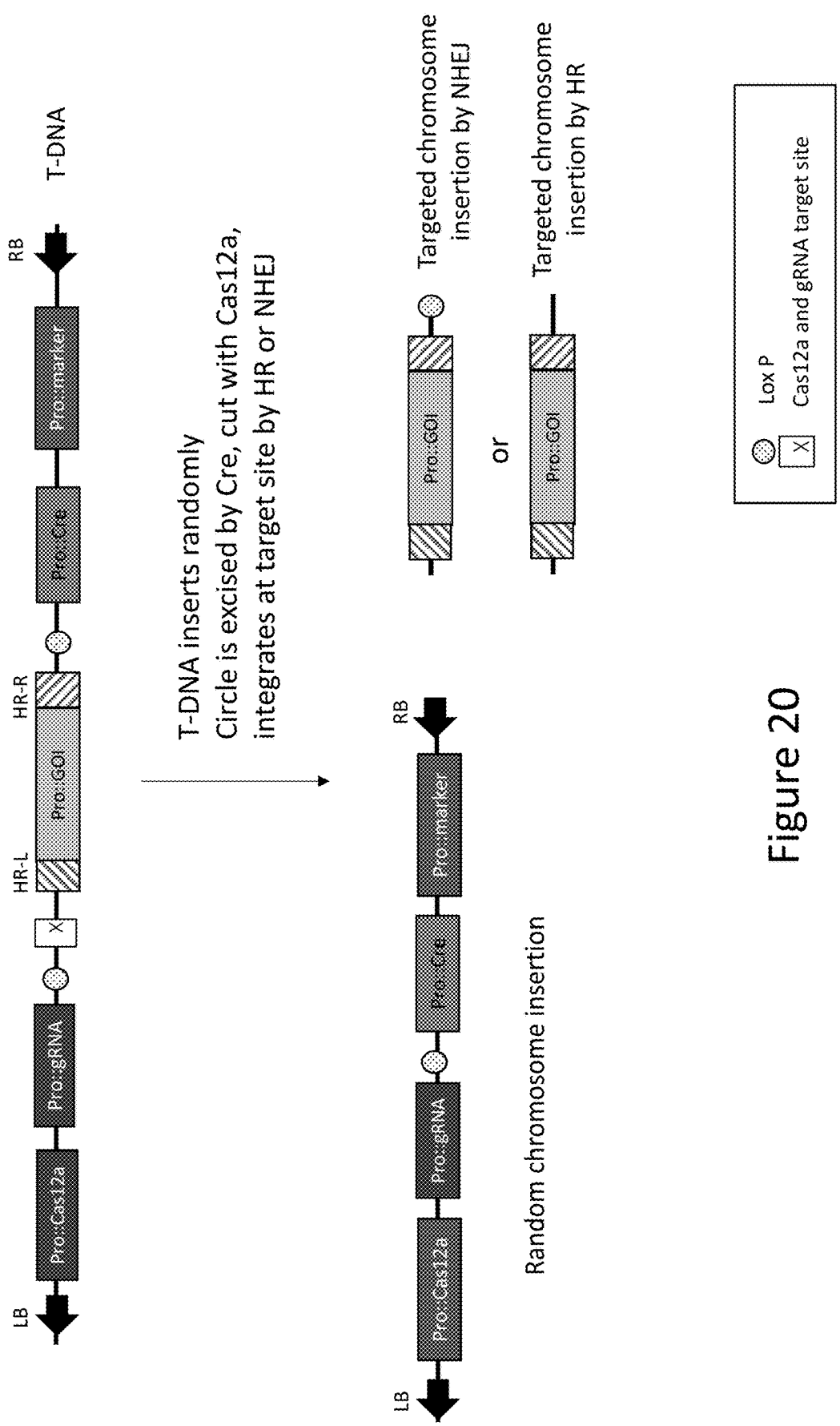
FIG. 20: depicts a schematic illustrating configuration of a vector for directional site-directed integration by homologous recombination. HR-L: left homology arm, HR-R: right homology arm.

Example 16. Using Cre/Lox to Make Targeted Insertions Via Homologous Recombination A T-DNA is produced that comprises, in 5' to 3' order, a left border (LB) sequence; a promoter operably linked to a sequence encoding a Cas12a nuclease; a Polymerase III promoter operably linked to a sequence encoding a guide RNA; a first lox site; a Cas12a target site; a left homology arm (HR-L) comprising a sequence showing homology to the left flank of the genomic target site; a gene of interest; a right homology arm (HR-R) comprising a sequence showing homology to the right flank of the genomic target site; a second lox site; a promoter operably linked to a sequence encoding Cre recombinase; a promoter operably linked to a sequence encoding a selectable marker gene; and a right border (RB) sequence. See FIG. 20.

interest flanked by HR-L and HR-R. The expression of Cas12a and gRNA allows the circularized T-DNA fragment to be cut as well as the target site in the genome, thereby allowing the gene of interest to integrate at the targeted chromosome location. The T-DNA fragment can integrate at the target site via Non Homologous End Joining mechanisms (NHEJ) which would result in the retention of the second lox site in the integrated fragment. Alternatively, the presence of the homology arms may promote the integration of the gene of interest into the genomic target site via Homologous Recombination (HR) mechanisms whereby the second Lox site is not present in the integrated fragment.

Figure 21:
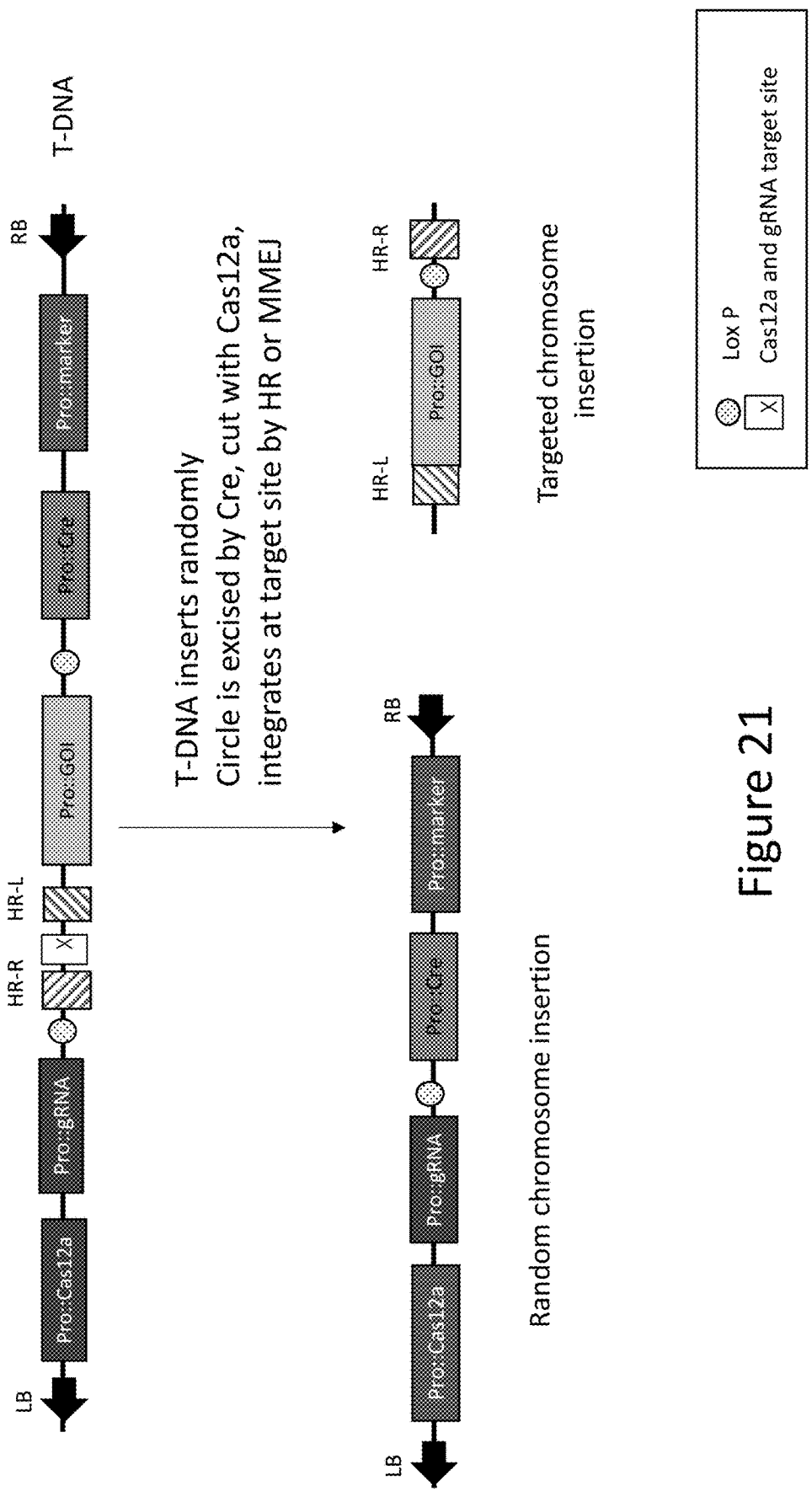
FIG. 21: depicts a schematic illustrating configuration of a vector for directional site-directed integration by homologous recombination. HR1: homology arm 1, HR2: homology arm 2.

Example 17. Using Cre/Lox to Make Targeted Insertions Via Homologous Recombination A T-DNA is produced that comprises, in 5' to 3' order, a left border (LB) sequence; a promoter operably linked to a sequence encoding a Cas12a nuclease; a Polymerase III promoter operably linked to a sequence encoding a guide RNA; a first lox site; a right Homologous Recombination arm (HR-R) comprising a sequence showing homology to the right flank of the genomic target site; a Cas12a target site; a left Homologous Recombination arm (HR-L) comprising a sequence showing homology to the left flank of the genomic target site; promoter operably linked to a sequence encoding a gene of interest; a second lox site; a promoter operably linked to a sequence encoding Cre recombinase; a promoter operably linked to a sequence encoding a selectable marker gene; and a right border (RB) sequence. See FIG. 21.

The construct is introduced into plant cells via *Agrobacterium*-mediated transformation, and the T-DNA inserts randomly in the genome of the plant cell. Once Cre recombinase activates, it excises and circularizes a fragment of the T-DNA comprising the Cas12a target site and the promoter operably linked to a sequence encoding a gene of interest flanked by HR-L and HR-R. The expression of Cas12a and gRNA allows the circularized T-DNA fragment to be cut as well as cleave the target site in the genome, thereby allowing the promoter operably linked to a sequence encoding a gene of interest to integrate at the targeted chromosome location. The presence of the exposed HR arms may promote the integration of the gene of interest cassette into the genomic target site via Homologous Recombination (HR) mechanisms or via Microhomology Mediated End Joining (MMEJ).

Example 18. Using TALE to Induce Cre Expression and Cre/Lox to Make Targeted Insertions This example describes a T-DNA vector design that utilizes TALE (Transcription Activator-Like Effector) protein to induce expression of Cre recombinase resulting in T-strand circle formation which results in the inactivation of Cre thereby limiting the expression of recombinase. Transcription Activator-Like Effectors (TALEs), are transcription factors that comprise a C-terminal Activation domain that can activate or increase the expression of a gene once they bind to the TALE Binding Site (TBS) DNA at or near the gene's promoter.

Figure 22:
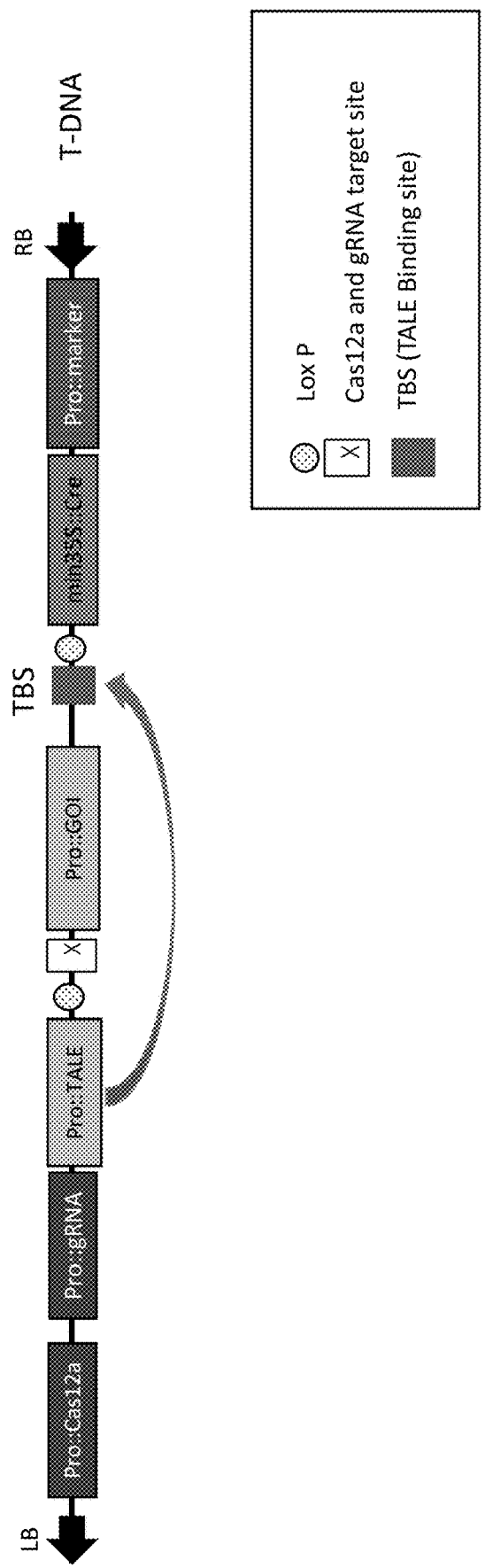
FIG. 22: depicts a schematic illustrating configuration of an *Agrobacterium* T-DNA vector designed to produce circular substrates in vivo by Cre/lox recombination system to promote targeted integration of a GOI cassette at a genomic locus. Following T-DNA integration, the TALE (Transcription activator-like effector) protein binds to the TALE Binding Site (TBS) and drives the transcription of the Cre recombinase via a 35S Minimal promoter (min35S). Cre mediated excision of the Pro::GOI cassette unlinks the TBS from the Cre cassette thereby limiting Cre expression.

A T-DNA is produced that comprises, in 5' to 3' order, a left border (LB) sequence; a promoter operably linked to a sequence encoding a Cas12a nuclease; a Polymerase III promoter operably linked to a sequence encoding a guide RNA; a promoter operably linked to a sequence encoding a TALE protein comprising an Activation domain; a first lox site; a Cas12a target site; a gene of interest; a TALE Binding site (TBS); a second lox site; a minimal promoter (e.g., 35S minimal promoter) operably linked to a sequence encoding Cre recombinase; a promoter operably linked to a sequence encoding a selectable marker gene; and a right border (RB) sequence. See FIG. 22.

The construct is introduced into plant cells via *Agrobacterium*-mediated transformation, and the T-DNA inserts randomly in the genome of the plant cell. The TALE protein is expressed and binds to the TBS located adjacent to the minimal promoter leading to the expression of Cre. Cre recombinase excises and circularizes a fragment of the T-DNA comprising the Cas12a target site; the gene of interest and the TBS. The expression of Cas12a and gRNA allows the circularized T-DNA fragment to be cut as well as cleave the target site in the genome, thereby allowing the gene of interest to integrate at the targeted chromosome location. The excision of the T-DNA fragment leads to the unlinking of the TBS from the Cre cassette and as a result Cre is no longer expressed. Limiting Cre expression may help prevent unwanted recombination events between the Gene of Interest after integration into the genomic target site and the rest of the T-DNA, which is situated at another locus in the genome. Limited Cre expression may also reduce negative phenotypes that have been attributed to Cre expression in some dicot species, e.g. soy.

While the preferred embodiment uses a TALE to activate Cre expression, a catalytically inactive Cas12a (dCas12a) fused to a Transcription Factor (TF) activation domain (dCas12a-TF) may be used in lieu of the TALE protein. dCas12a comprises a R1226A mutation in the Nuc domain resulting in a protein that lacks the nuclease activity but retains the ability to bind to a target site in the presence of the appropriate gRNA. dCas12a-TF may be used to activate the expression of Cre operably associated with a minimal promoter and an appropriate dCas12a Target Binding site. In another embodiment, it may be possible to take advantage of a native transcription factor, eliminating the need for a TALE or dCas12a-TFcassette in the T-DNA. In such a scenario the TBS in the T-DNA is replaced with a binding site for an appropriate native transcription factor.

Example 19: Generating Multiple Circularized T-DNA Fragments from a Single T-DNA This example describes a T-DNA vector designed to increase the frequency of SDI by generating multiple Cre-mediated circularized T-DNA fragments from a single T-DNA vector.

Figure 23:
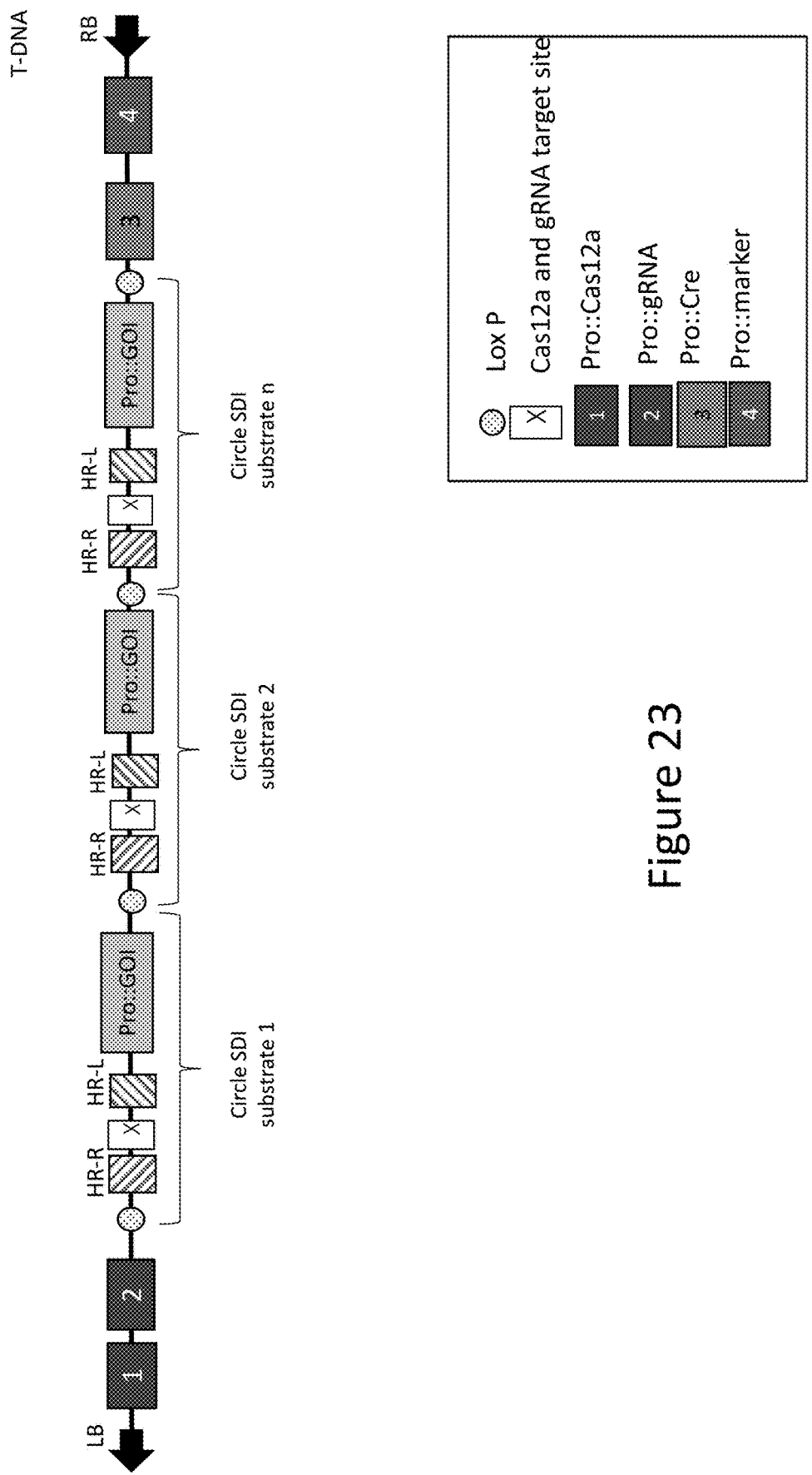
FIG. 23: depicts a schematic illustrating configuration of an *Agrobacterium* T-DNA vector designed to produce multiple circular substrates in vivo by Cre/lox recombination system to promote targeted integration of a GOI cassette at a genomic locus vector.

A T-DNA is produced that comprises, in 5' to 3' order, a left border (LB) sequence; a promoter operably linked to a sequence encoding a Cas12a nuclease; a Polymerase III promoter operably linked to a sequence encoding a guide RNA; a first lox site; a first right homology arm (HR-R) comprising a sequence showing homology to the right flank of the genomic target site; a first Cas12a target site; a first left homology arm (HR-L) comprising a sequence showing homology to the left flank of the genomic target site; a first Gene of Interest; a second lox site; a second HR-R arm, a second Cas12a target site; a second gene of interest; a third lox site; a third HR-R sequence; a third Cas12a target site; a third HR-L sequence; a third GOI; a fourth lox site; promoter operably linked to a sequence encoding Cre recombinase; a promoter operably linked to a sequence encoding a selectable marker gene; and a right border (RB) sequence. See FIG. 23. In the design described above, each T-DNA sequence flanked by lox sites can be excised and circularized to provide a T-DNA fragment SDI substrate. Thus, the design above produces 3 circularized T-DNA fragment SDI substrates.

The construct is introduced into plant cells via *Agrobacterium*-mediated transformation, and the T-DNA inserts randomly in the genome of the plant cell. Following expression, Cre recombinase excises and circularizes a fragment of the T-DNA flanked by the lox sites. Excision of T circles can happen in many ways, either each T-Circle substrate can be excised individually, or one big circularized T-DNA fragment could be excised that then gets resolved down to 3 individual circles each comprising the Cas12a target site and the gene of interest flanked by HR-L and HR-R. The expression of Cas12a and gRNA allows the circularized T-DNA fragment to be cut as well as cleave the target site in the genome, thereby allowing the gene of interest to integrate at the chromosomal target site. The presence of the exposed homology arms may promote the integration of the gene of interest cassette into the genomic target site via Homologous Recombination (HR) mechanisms or via Microhomology Mediated End Joining (MMEJ). The presence of multiple circularized T-DNA fragments may lead to more substrates for SDI, thereby increasing the SDI frequency.

Example 20: Using Viral Replicons to Make Targeted Insertions

This example describes T-DNA vector designs that utilize replicase and Long Intergenic Region (LIR) elements from Nanoviruses and Geminiviruses to provide circularized fragments in sufficiently high copy number for efficient SDI.

Geminiviridae and Nanoviridae families of ssDNA plant viruses replicate via a rolling circle mechanism. The replication initiation protein/replicase (Rep) recognizes a domain in the large intergenic region (LIR) of the viral DNA and nicks the DNA at a conserved site found on the hairpin structure of the LIR to promote rolling circle replication and the generation of circular replicons. It has previously been reported that Geminivirus and Nanovirus replicases can recognize and circularize DNA carrying a donor sequence flanked by their cognate LIRs (see Aronson et al., 2002, The Plant Journal., 31(6)., 767-775; see Baltes et al. 2014, The Plant Cell, 26:1, 151-163). Furthermore, engineered geminiviral replicons comprising a donor DNA, when combined with targeted chromosome cutting has been shown to promote targeted integration of the donor DNA sequence (see Aronson et al., 2002, The Plant Journal., 31(6)., 767-775).

Geminiviral T-DNA vectors: A T-DNA is produced that comprises, in 5' to 3' order, a left border (LB) sequence; a promoter operably linked to a sequence encoding a selectable marker gene; a promoter operably linked to a sequence encoding a Cas12a nuclease; a first sequence comprising the LIR from the Soybean Chlorotic Spot Virus Geminivirus (SCSV) (SEQ ID NO: 64); a Cas12a target site; a first Gene of Interest; a second sequence comprising the LIR from SCSV; an SCSV Rep (Replicase) cassette comprising a promoter operably linked to a DNA sequence encoding the SCSV Rep (SEQ ID NO 65); a Polymerase III promoter operably linked to a sequence encoding a guide RNA; and a right border (RB) sequence. A control vector identical in design but lacking the Rep cassette is also generated.

Figure 24:
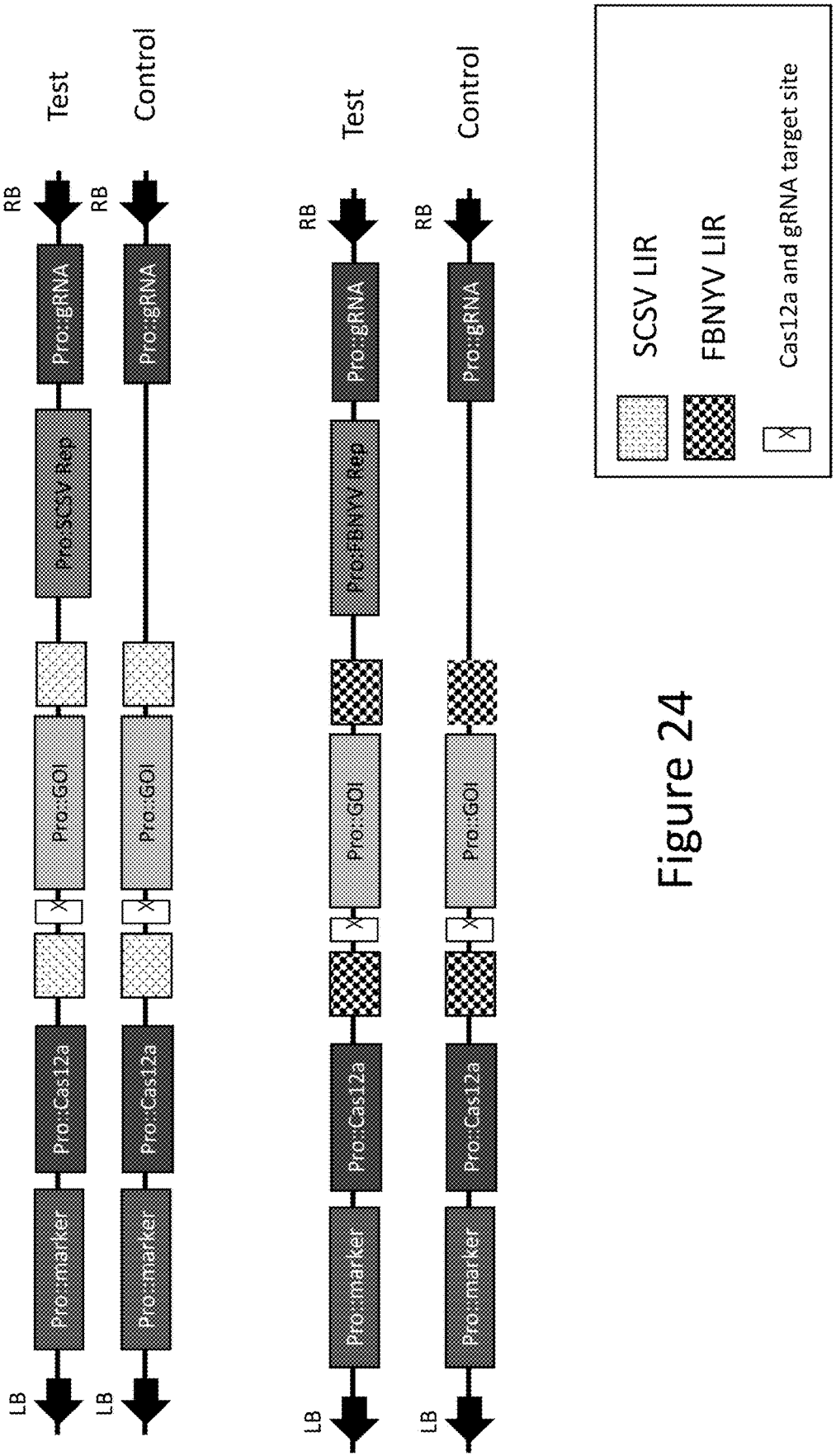
FIG. 24: depicts a schematic illustrating configuration of an *Agrobacterium* T-DNA vector designed to produce circular substrates in vivo using viral replicons to promote targeted integration of a GOI cassette at a genomic locus vector.

Nanoviral T-DNA vectors: A T-DNA is produced that comprises, in 5' to 3' order, a left border (LB) sequence; a promoter operably linked to a sequence encoding a selectable marker gene; a promoter operably linked to a sequence encoding a Cas12a nuclease; a first sequence comprising the LIR from the (Faba Bean necrotic Yellow Virus (FBNYV) (SEQ ID NO: 66); a Cas12a target site; a first Gene of Interest; a second sequence comprising the LIR from FBNYV; an FBNYV Rep cassette comprising a promoter operably linked to a DNA sequence encoding the FBNYV Rep (SEQ ID NO 67); a Polymerase III promoter operably linked to a sequence encoding a guide RNA; and a right border (RB) sequence. A control vector identical in design but lacking the Rep cassette is also generated. See FIG. 24.

The test and control constructs are introduced into plant cells via Agrobacterium-mediated transformation. The T-DNA inserts randomly in the genome of the plant cell. Successful expression of the Viral Rep protein from the Test constructs is expected to circularize the fragment of the constructs comprising the gene of interest flanked by LIRs. The expression of Cas12a and gRNA allows the circularized T-DNA fragment to be cut as well as cleave the target site in the genome, thereby allowing the Gene of Interest to integrate at the targeted chromosomal location.

An advantage of using T-DNA vectors comprising viral replicase-LIR elements is the possibility of generating a high copy number of the circular fragments comprising the GOI cassette within the cell nucleus in the presence of the viral replicase protein. This in turn could improve SDI rates. Viral replicase mediated enrichment in SDI may be evidenced by higher integration rates in tests versus controls in a statistically meaningful manner.

Example 21: Introns for Split Marker Vectors

This example provides examples of monocot introns that may be used in place of the Actin intron (SEQ ID NO:22) used in Corn Split marker vectors described in Example 3.

TABLE 15

Monocot Introns

| Intron name | Intron size | SEQ ID NO |
|---|---|---|
| I-SETit.Act4 | 1364 | 68 |
| I-SETit.NAB | 1379 | 69 |
| I-CI.DnaK1 | 1025 | 70 |
| I-SETit.DnaK9 | 1801 | 71 |
| I-SETvi.DnaK2 | 1159 | 72 |
| I-SETit.DnaK5 | 899 | 73 |
| I-SETit.TubA2 | 934 | 74 |
| I-SETit.eIF5A2 | 910 | 75 |
| I-SETit.eIF5A3 | 1014 | 76 |
| I-SETit.14-3-3C | 1152 | 77 |
| I-SETit.eEF2-1 | 1336 | 78 |
| I-SETit.eEF1g | 1190 | 79 |
| I-SETit.eEF1g_3 | 906 | 80 |
| I-SETit.Act6 | 1201 | 81 |
| I-SETit.14-3-3B | 1012 | 82 |

The invention claimed is:

1. A recombinant nucleic acid construct comprising:
(a) a left border (LB) sequence;
(b) a first recombination site and a second recombination site;
(c) a target site for a guided nuclease;
(d) a sequence of interest; (e) a right border (RB) sequence; and
(f) a single intron sequence, wherein the intron sequence is split into a 5' portion of the intron sequence and a 3' portion of the intron sequence, wherein the 5' portion of the intron sequence is positioned 5' to the RB sequence, wherein the 3' portion of the intron sequence is positioned 3' to the LB sequence, and wherein the 5' portion of the intron sequence and the 3' portion of the intron sequence are not adjacent to each other, wherein the target site for the guided nuclease and the sequence of interest are positioned between the first recombination site and the second recombination site.

2. The recombinant nucleic acid construct of claim 1, wherein the sequence of interest comprises a promoter operably linked to a sequence encoding a herbicide tolerance protein or a pesticidal protein.

3. The recombinant nucleic acid construct of claim 1, wherein the construct further comprises an expression cassette encoding at least one selectable marker.

4. The recombinant nucleic acid construct of claim 3, wherein the selectable marker is selected from the group consisting of nptII, aph IV, aadA, aac3, aacC4, bar, pat, DMO, EPSPS, aroA, luciferase, GFP, and GUS.

5. The recombinant nucleic acid construct of claim 1, wherein the recombinant nucleic acid construct further comprises a sequence encoding a guided nuclease operably linked to a promoter.

6. The recombinant nucleic acid construct of claim 3, wherein the expression cassette encoding at least one selectable marker comprises (a) a promoter; (b) at least one intron; and (c) a protein-coding sequence.

7. The expression cassette of claim 6, wherein the promoter is positioned between the sequence of interest and the RB sequence, and wherein the protein-coding sequence is positioned between the LB sequence and the sequence of interest.

8. The expression cassette of claim 1, wherein the single intron sequence is selected from SEQ ID NOs: 22, 68, 69, 70, 71, and 72.

9. The expression cassette of claim 6, wherein the promoter is selected from the group consisting of a constitutive promoter, an inducible promoter, and a tissue-specific promoter.

10. The recombinant nucleic acid construct of claim 1, wherein (a) the LB is a truncated LB sequence, (b) the RB is a truncated RB sequence, or (c) both (a) and (b).

11. The recombinant nucleic acid construct of claim 1, wherein the construct further comprises a sequence encoding at least one recombinase.

12. The recombinant nucleic acid construct of claim 3, wherein the construct comprises the following components in 5' to 3' order: a second promoter, the first recombination site, the target site for the guided nuclease, the sequence of interest, the second recombination site, and the at least one sequence encoding a selectable marker, wherein the second promoter and the at least one sequence encoding a selectable marker are in the same orientation.

13. The recombinant nucleic acid construct of claim 5, wherein the guided nuclease is selected from the group consisting of an RNA-guided nuclease, a zinc-finger nuclease, a meganuclease, a transcription activator-like effector (TALE) nuclease, and a TALE-like protein.

14. The recombinant nucleic acid construct of claim 1, wherein the construct further comprises a sequence encoding one or more guide RNAs (gRNAs) operably linked to a Pol III promoter.

15. The recombinant nucleic acid construct of claim 14, wherein the sequence encoding one or more gRNAs encodes a first gRNA that is capable of hybridizing with the target site for the guided nuclease in the recombinant nucleic acid construct.

16. The recombinant nucleic acid construct of claim 1, wherein a guided nuclease generates a 4-nucleotide overhang after cleaving the construct at the target site for the guided nuclease.

17. The recombinant nucleic acid construct of claim 1, wherein the target site for a guided nuclease in the recombinant nucleic acid construct comprises a 4 bp PAM and a 23 bp spacer-complementary sequence.

18. The recombinant nucleic acid construct of claim 1, wherein the construct further comprises a first homology arm (HR1) and a second homology arm (HR2).

19. A recombinant nucleic acid construct comprising, from 5' to 3':
  (a) a left border (LB) sequence or a truncated LB (tLB) sequence;
  (b) a 3' portion of a single intron sequence;
  (c) a sequence encoding at least one selectable marker;
  (d) a first recombination site;
  (e) a sequence of interest;
  (f) a target site for a guided nuclease;
  (g) a second recombination site;
  (h) a promoter operably linked to a 5' portion of the single intron sequence; and
  (i) a right border (RB) sequence or a truncated RB (tRB) sequence,
wherein the promoter, the 3' portion of the single intron sequence, the 5' portion of the single intron sequence, and the sequence encoding at least one selectable marker are in the same orientation.

20. The recombinant nucleic acid construct of claim 19, wherein the recombinant nucleic acid construct further comprises:
  (j) a promoter operably linked to a sequence encoding a guided nuclease; or
  (k) a promoter operably linked to a sequence encoding a guide RNA; or
  (l) both (j) and (k),
wherein (j), (k), or (l) are positioned between the LB or tLB sequence and the RB or tRB sequence, and wherein (j), (k), or (l) are not positioned between the first recombination site and the second recombination site.

* * * * *

SEQUENCE LISTING

<160> NUMBER OF SEQ ID NOS: 82

<210> SEQ ID NO 1
<211> LENGTH: 505
<212> TYPE: DNA
<213> ORGANISM: Agrobacterium tumefaciens

<400> SEQUENCE: 1

```
cgaagctcgg tcccgtgggt gttctgtcgt ctcgttgtac aacgaaatcc attcccattc      60
cgcgctcaag atggcttccc ctcggcagtt catcagggct aaatcaatct agccgacttg     120
tccggtgaaa tgggctgcac tccaacagaa acaatcaaac aaacatacac agcgacttat     180
tcacacgagc tcaaattaca acggtatata tcctgccagt cagcatcatc acaccaaaag     240
ttaggcccga atagtttgaa attagaaagc tcgcaattga ggtctacagg ccaaattcgc     300
tcttagccgt acaatattac tcaccggtgc gatgccccc atcgtaggtg aaggtggaaa     360
ttaatgatcc atcttgagac cacaggccca caacagctac cagtttcctc aagggtccac     420
caaaaacgta agcgcttacg tacatggtcg ataagaaaag gcaatttgta gatgttaaca     480
tccaacgtcg ctttcaggga tcctt                                            505
```

<210> SEQ ID NO 2
<211> LENGTH: 442
<212> TYPE: DNA
<213> ORGANISM: Agrobacterium tumefaciens

<400> SEQUENCE: 2

```
ctcatctaag cccccatttg gacgtgaatg tagacacgtc gaaataaaga tttccgaatt    60
agaataattt gtttattgct ttcgcctata aatacgacgg atcgtaattt gtcgttttat   120
caaaatgtac tttcatttta taataacgct gcggacatct acatttttga attgaaaaaa   180
aattggtaat tactctttct tttctccat attgaccatc atactcattg ctgatccatg    240
tagatttccc ggacatgaag ccatttacaa ttgaatatat cctgccgccg ctgccgcttt   300
gcacccggtg gagcttgcat gttggttttct acgcagaact gagccggtta ggcagataat   360
ttccattgag aactgagcca tgtgcacctt cccccaaca cggtgagcga cggggcaacg    420
gagtgatcca catgggactt tt                                             442
```

<210> SEQ ID NO 3
<211> LENGTH: 2525
<212> TYPE: DNA
<213> ORGANISM: Artificial Sequence
<220> FEATURE:
<223> OTHER INFORMATION: Synthetic sequence

<400> SEQUENCE: 3

```
actagtcaac aattggccaa tctttgttct aaattgctaa taaacgacca tttccgtcaa    60
ttctccttgg ttgcaacagt ctacccgtca atgtttact aatttataag tgtgaagttt    120
gaattatgaa agacgaaatc gtattaaaaa ttcacaagaa taaacaactc catagatttt   180
caaaaaaaca gtcacgagaa aaaaccaca gtccgtttgt ctgctcttct agttttatt    240
atttttctat taatagtttt ttgttatttc gagaataaaa tttgaacgat gtccgaacca   300
caaaagccga gccgataaat cctaagccga gcctaacttt agccgtaacc atcagtcacg   360
gctcccgggc taattcattt gaaccgaatc ataatcaacg gtttagatca aactcaaaac   420
aatctaacgg caacatagac gcgtcggtga gctaaaaaga gtgtgaaagc caggtcacca   480
tagcattgtc tctcccagat ttttatttg ggaaataata aagaaaatag aaaaaaataa    540
aagagtgaga aaaatcgtag agctatatat tcgcacatgt actcgtttcg ctttccttag   600
tgttagctgc tgccgctgtt gtttctcctc catttctcta tctttctctc tcgctgcttc   660
tcgaatcttc tgtatcatct tcttcttctt caaggtgagt ctctagatcc gttcgcttga   720
ttttgctgct cgttagtcgt tattgttgat tctctatgcc gatttcgcta gatctgttta   780
gcatgcgttg tggttttatg agaaaatctt tgttttgggg gttgcttgtt atgtgattcg   840
atccgtgctt gttggatcga tctgagctaa ttcttaaggt ttatgtgtta gatctatgga   900
gtttgaggat tcttctcgct tctgtcgatc tctcgctgtt atttttgttt ttttcagtga   960
agtgaagttg tttagttcga aatgacttcg tgtatgctcg attgatctgg ttttaatctt  1020
cgatctgtta ggtgttgatg tttacaagtg aattctagtg ttttctcgtt gagatctgtg  1080
aagtttgaac ctagttttct caataatcaa catatgaagc gatgtttgag tttcaataaa  1140
cgctgctaat cttcgaaact aagttgtgat ctgattcgtg tttacttcat gagcttatcc  1200
aattcatttc ggtttcattt actttttttt ttagtgaacc atggcgcaag ttagcagaat  1260
ctgcaatggt gtgcagaacc catctcttat ctccaatctc tcgaaatcca gtcaacgcaa  1320
atctccctta tcggtttctc tgaagacgca gcagcatcca cgagcttatc cgatttcgtc  1380
```

```
gtcgtgggga ttgaagaaga gtgggatgac gttaattggc tctgagcttc gtcctcttaa    1440
ggtcatgtct tctgtttcca cggcgtgcat gggggaagcg gtgatcgccg aagtatcgac    1500
tcaactatca gaggtagttg gcgtcatcga gcgccatctc gaaccgacgt tgctggccgt    1560
acatttgtac ggctccgcag tggatggcgg cctgaagcca cacagtgata ttgatttgct    1620
ggttacggtg accgtaaggc ttgatgaaac aacgcggcga gctttgatca cgacctttt     1680 ggaaacttcg gcttcccctg agagagcga gattctccgc gctgtagaag tcaccattgt     1740
tgtgcacgac gacatcattc cgtggcgtta ccagctaag cgcgaactgc aatttggaga     1800
atggcagcgc aatgacattc ttgcaggtat cttcgagcca ccacgatcg acattgatct     1860 ggctatcttg ctgacaaaag caagagaaca tagcgttgcc ttggtaggtc agcggcgga    1920 ggaactcttt gatccggttc ctgaacagga tctatttgag gcgctaaatg aaacttaac    1980 gctatggaac tcgccgcccg actgggctgg cgatgagcga aatgtagtgc ttacgttgtc    2040
ccgcatttgg tacagcgcag taaccggcaa atcgcgccg aaggatgtcg ctgccgactg     2100
ggcaatggag cgcctgccgg cccagtatca gcccgtcata cttgaagcta gacaggctta    2160
tcttggacaa gaagaagatc gcttggcctc gcgcgcagat cagttggaag aatttgtcca    2220
ctacgtgaaa ggcgagatca ccaaggtagt cggcaaataa ggatcaattc ccgatcgttc    2280
aaacatttgg caataaagtt tcttaagatt gaatcctgtt gccggtcttg cgatgattat    2340
catataattt ctgttgaatt acgttaagca tgtaataatt aacatgtaat gcatgacgtt    2400
atttatgaga tgggttttta tgattagagt cccgcaatta tacatttaat acgcgataga    2460
aaacaaaata tagcgcgcaa actaggataa attatcgcgc gcggtgtcat ctatgttact    2520
agatc                                                               2525

<210> SEQ ID NO 4
<211> LENGTH: 600
<212> TYPE: DNA
<213> ORGANISM: Arabidopsis thaliana

<400> SEQUENCE: 4
actagtcaac aattggccaa tctttgttct aaattgctaa taaacgacca tttccgtcaa     60
ttctccttgg ttgcaacagt ctacccgtca aatgtttact aatttataag tgtgaagttt    120
gaattatgaa agacgaaatc gtattaaaaa ttcacaagaa taaacaactc catagatttt    180
caaaaaaaca gtcacgagaa aaaaaccaca gtccgtttgt ctgctcttct agtttttatt    240 attttctat taatagtttt ttgttatttc gagaataaaa tttgaacgat gtccgaacca    300
caaaagccga gccgataaat cctaagccga gcctaacttt agccgtaacc atcagtcacg    360
gctcccgggc taattcattt gaaccgaatc ataatcaacg gtttagatca aactcaaaac    420
aatctaacgg caacatagac gcgtcggtga gctaaaaaga gtgtgaaagc caggtcacca    480
tagcattgtc tctcccagat ttttttattttg ggaaataata gaagaaatag aaaaaaataa    540
aagagtgaga aaaatcgtag agctatatat tcgcacatgt actcgtttcg ctttccttag    600

<210> SEQ ID NO 5
<211> LENGTH: 94
<212> TYPE: DNA
<213> ORGANISM: Arabidopsis thaliana

<400> SEQUENCE: 5
tgttagctgc tgccgctgtt gtttctcctc catttctcta tctttctctc tcgctgcttc     60
```
tcgaatcttc tgtatcatct tcttcttctt caag        94

<210> SEQ ID NO 6
<211> LENGTH: 544
<212> TYPE: DNA
<213> ORGANISM: Arabidopsis thaliana

<400> SEQUENCE: 6
gtgagtctct agatccgttc gcttgatttt gctgctcgtt agtcgttatt gttgattctc        60
tatgccgatt tcgctagatc tgtttagcat gcgttgtggt tttatgagaa aatctttgtt       120
ttggggttg cttgttatgt gattcgatcc gtgcttgttg gatcgatctg agctaattct        180
taaggtttat gtgttagatc tatggagttt gaggattctt ctcgcttctg tcgatctctc       240
gctgttattt tgtttttttt cagtgaagtg aagttgttta gttcgaaatg acttcgtgta       300
tgctcgattg atctggtttt aatcttcgat ctgttaggtg ttgatgttta caagtgaatt       360
ctagtgtttt ctcgttgaga tctgtgaagt ttgaacctag ttttctcaat aatcaacata       420
tgaagcgatg tttgagtttc aataaacgct gctaatcttc gaaactaagt tgtgatctga       480
ttcgtgttta cttcatgagc ttatccaatt catttcggtt tcattttact tttttttag       540
tgaa       544

<210> SEQ ID NO 7
<211> LENGTH: 228
<212> TYPE: DNA
<213> ORGANISM: Arabidopsis thaliana

<400> SEQUENCE: 7
atggcgcaag ttagcagaat ctgcaatggt gtgcagaacc catctcttat ctccaatctc        60
tcgaaatcca gtcaacgcaa atctcccttta tcggtttctc tgaagacgca gcagcatcca       120
cgagcttatc cgatttcgtc gtcgtgggga ttgaagaaga gtgggatgac gttaattggc       180
tctgagcttc gtcctcttaa ggtcatgtct tctgtttcca cggcgtgc       228

<210> SEQ ID NO 8
<211> LENGTH: 792
<212> TYPE: DNA
<213> ORGANISM: Escherichia coli

<400> SEQUENCE: 8
atgggggaag cggtgatcgc cgaagtatcg actcaactat cagaggtagt tggcgtcatc        60
gagcgccatc tcgaaccgac gttgctggcc gtacatttgt acggctccgc agtggatggc       120
ggcctgaagc cacacagtga tattgatttg ctggttacgg tgaccgtaag gcttgatgaa       180
acaacgcggc gagctttgat caacgacctt ttggaaactt cggcttcccc tggagagagc       240
gagattctcc gcgctgtaga agtcaccatt gttgtgcacg acgacatcat tccgtggcgt       300
tatccagcta agcgcgaact gcaatttgga gaatggcagc gcaatgacat tcttgcaggt       360
atcttcgagc cagccacgat cgacattgat ctggctatct tgctgacaaa agcaagagaa       420
catagcgttg ccttggtagg tccagcggcg gaggaactct tgatccggt tcctgaacag       480
gatctatttg aggcgctaaa tgaaacctta acgctatgga actcgccgcc cgactgggct       540
ggcgatgagc gaaatgtagt gcttacgttg tcccgcattt ggtacagcgc agtaaccggc       600
aaaatcgcgc cgaaggatgt cgctgccgac tgggcaatgg agcgcctgcc ggcccagtat       660
cagcccgtca tacttgaagc tagacaggct tatcttggac aagaagaaga tcgcttggcc       720
tcgcgcgcag atcagttgga agaatttgtc cactacgtga aaggcgagat caccaaggta       780

```
gtcggcaaat aa                                                          792
```

<210> SEQ ID NO 9
<211> LENGTH: 253
<212> TYPE: DNA
<213> ORGANISM: Agrobacterium tumefaciens

<400> SEQUENCE: 9

```
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggtttttatg attagagtcc cgcaattata catttaatac     180
gcgatagaaa acaaaatata gcgcgcaaac taggataaat tatcgcgcgc ggtgtcatct     240
atgttactag atc                                                         253
```

<210> SEQ ID NO 10
<211> LENGTH: 964
<212> TYPE: DNA
<213> ORGANISM: Arabidopsis thaliana

<400> SEQUENCE: 10

```
actagtcaac aattggccaa tctttgttct aaattgctaa taaacgacca tttccgtcaa      60
ttctccttgg ttgcaacagt ctacccgtca aatgtttact aatttataag tgtgaagttt     120
gaattatgaa agacgaaatc gtattaaaaa ttcacaagaa taaacaactc catagatttt     180
caaaaaaaca gtcacgagaa aaaaaccaca gtccgtttgt ctgctcttct agttttattt     240
attttttctat taatagttttt tgttattttc gagaataaaa tttgaacgat gtccgaacca     300
caaaagccga ccgataaaat cctaagccga gcctaacttt agccgtaacc atcagtcacg     360
gctcccgggc taattcattt gaaccgaatc ataatcaacg gtttagatca aactcaaaac     420
aatctaacgg caacatagac gcgtcggtga gctaaaaaga gtgtgaaagc caggtcacca     480
tagcattgtc tctcccagat ttttttatttg ggaaataata gaagaaatag aaaaaaataa     540
aagagtgaga aaaatcgtag agctatatat tcgcacatgt actcgtttcg ctttccttag     600
tgttagctgc tgccgctgtt gtttctcctc catttctcta tctttctctc tcgctgcttc     660
tcgaatcttc tgtatcatct tcttcttctt caaggtgagt ctctagatcc gttcgcttga     720
ttttgctgct cgttagtcgt tattgttgat tctctatgcc gatttcgcta gatctgttta     780
gcatgcgttg tggttttatg agaaaatctt tgttttgggg gttgcttgtt atgtgattcg     840
atccgtgctt gttggatcga tctgagctaa ttcttaaggt ttatgtgtta gatctatgga     900
gtttgaggat tcttctcgct tctgtcgatc tctcgctgtt attttttgttt ttttcagtga     960
agtg                                                                   964
```

<210> SEQ ID NO 11
<211> LENGTH: 1561
<212> TYPE: DNA
<213> ORGANISM: Artificial Sequence
<220> FEATURE:
<223> OTHER INFORMATION: Synthetic sequence

<400> SEQUENCE: 11

```
aagttgttta gttcgaaatg acttcgtgta tgctcgattg atctggtttt aatcttcgat      60
ctgttaggtg ttgatgttta caagtgaatt ctagtgtttt ctcgttgaga tctgtgaagt     120
ttgaacctag ttttctcaat aatcaacata tgaagcgatg tttgagtttc aataaacgct     180
```

```
gctaatcttc gaaactaagt tgtgatctga ttcgtgttta cttcatgagc ttatccaatt    240
catttcggtt tcattttact ttttttttag tgaaccatgg cgcaagttag cagaatctgc    300
aatggtgtgc agaacccatc tcttatctcc aatctctcga aatccagtca acgcaaatct    360
cccttatcgg tttctctgaa gacgcagcag catccacgag cttatccgat ttcgtcgtcg    420
tggggattga agaagagtgg gatgacgtta attggctctg agcttcgtcc tcttaaggtc    480
atgtcttctg tttccacggc gtgcatgggg aagcggtga tcgccgaagt atcgactcaa     540
ctatcagagg tagttggcgt catcgagcgc catctcgaac cgacgttgct ggccgtacat    600
ttgtacggct ccgcagtgga tggcggcctg aagccacaca gtgatattga tttgctggtt    660
acggtgaccg taaggcttga tgaaacaacg cggcgagctt tgatcaacga ccttttggaa    720
acttcggctt ccctggaga gagcgagatt ctccgcgctg tagaagtcac cattgttgtg     780
cacgacgaca tcattccgtg gcgttatcca gctaagcgcg aactgcaatt tggagaatgg    840
cagcgcaatg acattcttgc aggtatcttc gagccagcca cgatcgacat tgatctggct    900
atcttgctga caaaagcaag agaacatagc gttgccttgg taggtccagc ggcggaggaa    960
ctctttgatc cggttcctga acaggatcta tttgaggcgc taaatgaaac cttaacgcta    1020
tggaactcgc cgcccgactg ggctggcgat gagcgaaatg tagtgcttac gttgtcccgc    1080
atttggtaca gcgcagtaac cggcaaaatc gcgccgaagg atgtcgctgc cgactgggca    1140
atggagcgcc tgccggccca gtatcagccc gtcatacttg aagctagaca ggcttatctt    1200
ggacaagaag aagatcgctt ggcctcgcgc gcagatcagt tggaagaatt tgtccactac    1260
gtgaaaggcg agatcaccaa ggtagtcggc aaataaggat caattcccga tcgttcaaac    1320
atttggcaat aaagtttctt aagattgaat cctgttgccg gtcttgcgat gattatcata    1380
taatttctgt tgaattacgt taagcatgta ataattaaca tgtaatgcat gacgttattt    1440
atgagatggg ttttatgat tagagtcccg caattataca tttaatacgc gatagaaaac     1500
aaaatatagc gcgcaaacta ggataaatta tcgcgcgcgg tgtcatctat gttactagat    1560
c                                                                   1561

<210> SEQ ID NO 12
<211> LENGTH: 181
<212> TYPE: DNA
<213> ORGANISM: Agrobacterium tumefaciens

<400> SEQUENCE: 12
catttacaat tgaatatatc ctgccgccgc tgccgctttg cacccggtgg agcttgcatg     60
ttggtttcta cgcagaactg agccggttag gcagataatt tccattgaga actgagccat    120
gtgcaccttc cccccaacac ggtgagcgac ggggcaacgg agtgatccac atgggacttt    180
t                                                                    181

<210> SEQ ID NO 13
<211> LENGTH: 218
<212> TYPE: DNA
<213> ORGANISM: Agrobacterium tumefaciens

<400> SEQUENCE: 13
cgaagctcgg tcccgtgggt gttctgtcgt ctcgttgtac aacgaaatcc attcccattc     60
cgcgctcaag atggcttccc ctcggcagtt catcagggct aaatcaatct agccgacttg    120
tccggtgaaa tgggctgcac tccaacagaa acaatcaaac aaacatacac agcgacttat    180
tcacacgagc tcaaattaca acggtatata tcctgcca                           218
```

<210> SEQ ID NO 14
<211> LENGTH: 25
<212> TYPE: DNA
<213> ORGANISM: Agrobacterium tumefaciens

<400> SEQUENCE: 14
atttacaatt gaatatatcc tgccg                                          25

<210> SEQ ID NO 15
<211> LENGTH: 25
<212> TYPE: DNA
<213> ORGANISM: Agrobacterium tumefaciens

<400> SEQUENCE: 15
aattacaacg gtatatatcc tgcca                                          25

<210> SEQ ID NO 16
<211> LENGTH: 261
<212> TYPE: DNA
<213> ORGANISM: Agrobacterium tumefaciens

<400> SEQUENCE: 16
ctcatctaag ccccatttg gacgtgaatg tagacacgtc gaaataaaga tttccgaatt      60
agaataattt gtttattgct ttcgcctata aatacgacgg atcgtaattt gtcgttttat   120
caaaatgtac tttcatttta taataacgct gcggacatct acattttga attgaaaaaa   180 aattggtaat tactctttct tttctccat attgaccatc atactcattg ctgatccatg   240
tagatttccc ggacatgaag c                                            261

<210> SEQ ID NO 17
<211> LENGTH: 3272
<212> TYPE: DNA
<213> ORGANISM: Artificial Sequence
<220> FEATURE:
<223> OTHER INFORMATION: Synthetic sequence

<400> SEQUENCE: 17
tcgaggtcat tcatatgctt gagaagagag tcgggatagt ccaaaataaa acaaaggtaa    60
gattacctgg tcaaaagtga aaacatcagt taaaggtgg tataaagtaa aatatcggta   120
ataaaaggtg gcccaaagtg aaatttactc ttttctacta ttataaaaat tgaggatgtt   180
tttgtcggta ctttgatacg tcattttgt atgaattggt ttttaagttt attcgctttt   240
ggaaatgcat atctgtattt gagtcgggtt ttaagttcgt ttgcttttgt aaatacagag   300
ggatttgtat aagaaatatc tttagaaaaa cccatatgct aatttgacat aattttgag   360 aaaaatatat attcaggcga attctcacaa tgaacaataa taagattaaa atagctttcc   420
cccgttgcag cgcatgggta ttttttctag taaaaataaa agataaactt agactcaaaa   480
catttacaaa acaaccccct aaagttccta aagcccaaag tgctatccac gatccatagc   540
aagcccagcc caacccaacc caacccaacc caccccagtc cagccaactg acaatagtc    600 tccacacccc cccactatca ccgtgagttg tccgcacgca ccgcacgtct cgcagccaaa   660 aaaaaaaga aagaaaaaaa agaaaaagaa aaaacagcag gtgggtccgg gtcgtggggg   720
ccggaaacgc gaggaggatc gcgagccagc gacgaggccg gccctccctc cgcttccaaa   780
gaaacgcccc ccatcgccac tatatacata ccccccctc tcctcccatc ccccaaccc    840 taccaccacc accaccacca cctccacctc ctcccccctc gctgccggac gacgagctcc   900

```
tcccccctcc ccctccgccg ccgccgcgcc ggtaaccacc ccgcccctct cctctttctt    960
tctccgtttt ttttccgtc tcggtctcga tctttggcct tggtagtttg ggtgggcgag   1020
aggcggcttc gtgcgcgccc agatcggtgc gcgggagggg cgggatctcg cggctggggc   1080
tctcgccggc gtggatccgg cccggatctc gcggggaatg gggctctcgg atgtagatct   1140
gcgatccgcc gttgttgggg gagatgatgg ggggtttaaa atttccgccg tgctaaacaa   1200
gatcaggaag aggggaaaag ggcactatgg tttatatttt tatatatttc tgctgcttcg   1260
tcaggcttag atgtgctaga tctttctttc ttcttttttgt gggtagaatt tgaatccctc   1320
agcattgttc atcggtagtt tttcttttca tgatttgtga caaatgcagc ctcgtgcgga   1380
gcttttttgt aggtagaagt gatcaaccat ggcgcaagtt agcagaatct gcaatggtgt   1440
gcagaaccca tctcttatct ccaatctctc gaaatccagt caacgcaaat ctcccttatc   1500
ggtttctctg aagacgcagc agcatccacg agcttatccg atttcgtcgt cgtggggatt   1560
gaagaagagt gggatgacgt taattggctc tgagcttcgt cctcttaagg tcatgtcttc   1620
tgtttccacg gcgtgcatgc ttcacggtgc aagcagccgg cccgcaaccg cccgcaaatc   1680
ctctggcctt tccggaaccg tccgcattcc cggcgacaag tcgatctccc accggtcctt   1740
catgttcggc ggtctcgcga gcggtgaaac gcgcatcacc ggccttctgg aaggcgagga   1800
cgtcatcaat acgggcaagg ccatgcaggc gatgggcgcc cgcatccgta aggaaggcga   1860
cacctggatc atcgatggcg tcggcaatgg cggcctcctg gcgcctgagg cgccgctcga   1920
tttcggcaat gccgccacgg gctgccgcct gacgatgggc ctcgtcgggg tctacgattt   1980
cgacagcacc ttcatcggcg acgcctcgct cacaaagcgc ccgatgggcc gcgtgttgaa   2040
cccgctgcgc gaaatgggcg tgcaggtgaa atcggaagac ggtgaccgtc ttcccgttac   2100
cttgcgcggg ccgaagacgc cgacgccgat cacctaccgc gtgccgatgg cctccgcaca   2160
ggtgaagtcc gccgtgctgc tcgccggcct caacacgccc ggcatcacga cggtcatcga   2220
gccgatcatg acgcgcgatc atacggaaaa gatgctgcag ggctttggcg ccaaccttac   2280
cgtcgagacg gatgcggacg gcgtgcgcac catccgcctg gaaggccgcg gcaagctcac   2340
cggccaagtc atcgacgtgc cgggcgaccc gtcctcgacg gccttcccgc tggttgcggc   2400
cctgcttgtt ccgggctccg acgtcaccat cctcaacgtg ctgatgaacc ccacccgcac   2460
cggcctcatc ctgacgctgc aggaaatggg cgccgacatc gaagtcatca cccgcgcct   2520 tgccggcggc gaagacgtgg cggacctgcg cgttcgctcc tccacgctga agggcgtcac   2580
ggtgccggaa gaccgcgcgc cttcgatgat cgacgaatat ccgattctcg ctgtcgccgc   2640
cgccttcgcg gaagggcga ccgtgatgaa cggtctggaa gaactccgcg tcaaggaaag   2700
cgaccgcctc tcggccgtcg ccaatggcct caagctcaat ggcgtggatt gcgatgaggg   2760
cgagacgtcg ctcgtcgtgc gtggccgccc tgacggcaag gggctcggca cgcctcggg   2820 cgccgccgtc gccacccatc tcgatcaccg catcgccatg agcttcctcg tcatgggcct   2880
cgtgtcggaa aaccctgtca cggtggacga tgccacgatg atcgccacga gcttcccgga   2940
gttcatggac ctgatggccg ggctgggcgc gaagatcgaa ctctccgata cgaaggctgc   3000
ctgatgagct cgaattcccg atcgttcaaa catttggcaa taaagtttct taagattgaa   3060
tcctgttgcc ggtcttgcga tgattatcat ataatttctg ttgaattacg ttaagcatgt   3120
aataattaac atgtaatgca tgacgttatt tatgagatgg gttttatga ttagagtccc   3180 gcaattatac atttaatacg cgatagaaaa caaaatatag cgcgcaaact aggataaatt   3240
atcgcgcgcg gtgtcatcta tgttactaga tc                                 3272
```

<210> SEQ ID NO 18
<211> LENGTH: 841
<212> TYPE: DNA
<213> ORGANISM: Oryza sativa

<400> SEQUENCE: 18

```
tcgaggtcat tcatatgctt gagaagagag tcgggatagt ccaaaataaa acaaaggtaa        60
gattacctgg tcaaaagtga aaacatcagt taaaagtgg tataaagtaa aatatcggta       120
ataaaaggtg gcccaaagtg aaatttactc ttttctacta ttataaaaat tgaggatgtt       180
tttgtcggta ctttgatacg tcattttgt atgaattggt ttttaagttt attcgctttt       240
ggaaatgcat atctgtattt gagtcgggtt ttaagttcgt ttgcttttgt aaatacagag       300
ggatttgtat aagaaatatc tttagaaaaa cccatatgct aatttgacat aattttgag       360
aaaaatatat attcaggcga attctcacaa tgaacaataa taagattaaa atagctttcc       420
cccgttgcag cgcatgggta tttttctag taaaaataaa agataaactt agactcaaaa       480
catttacaaa acaacccct aaagttccta agcccaaag tgctatccac gatccatagc        540
aagcccagcc caaccaacc caacccaacc caccccagtc cagccaactg gacaatagtc       600
tccacacccc cccactatca ccgtgagttg tccgcacgca ccgcacgtct cgcagccaaa       660
aaaaaaaaga agaaaaaaa agaaaaagaa aaaacagcag gtgggtccgg gtcgtgggg       720
ccggaaacgc gaggaggatc gcgagccagc gacgaggccg gccctccctc cgcttccaaa       780
gaaacgcccc ccatcgccac tatatacata ccccccctc cctcccatc ccccaaccc        840
t                                                                      841
```

<210> SEQ ID NO 19
<211> LENGTH: 80
<212> TYPE: DNA
<213> ORGANISM: Oryza sativa

<400> SEQUENCE: 19

```
accaccacca ccaccaccac ctccacctcc tccccctcg ctgccggacg acgagctcct        60
ccccctccc cctccgccgc                                                    80
```

<210> SEQ ID NO 20
<211> LENGTH: 478
<212> TYPE: DNA
<213> ORGANISM: Oryza sativa

<400> SEQUENCE: 20

```
cgccgcgccg gtaaccaccc cgcccctctc ctctttcttt ctccgttttt ttttccgtct        60
cggtctcgat ctttggcctt ggtagtttgg gtgggcgaga ggcggcttcg tgcgcgccca       120
gatcggtgcg cgggagggc gggatctcgc ggctggggct ctcgccggcg tggatccggc       180
ccggatctcg cggggaatgg ggctctcgga tgtagatctg cgatccgccg ttgttggggg       240
agatgatggg gggtttaaaa tttccgccgt gctaaacaag atcaggaaga ggggaaaagg       300
gcactatggt ttatattttt atatatttct gctgcttcgt caggcttaga tgtgctagat       360
ctttctttct tcttttgtg ggtagaattt gaatccctca gcattgttca tcggtagttt       420
ttcttttcat gatttgtgac aaatgcagcc tcgtgcggag cttttttgta ggtagaag        478
```

<210> SEQ ID NO 21
<211> LENGTH: 1596
<212> TYPE: DNA

<213> ORGANISM: Artificial Sequence
<220> FEATURE:
<223> OTHER INFORMATION: Synthetic sequence

<400> SEQUENCE: 21

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat gcttcacggt     240
gcaagcagcc ggcccgcaac cgcccgcaaa tcctctggcc tttccggaac cgtccgcatt     300
cccggcgaca agtcgatctc ccaccggtcc ttcatgttcg gcggtctcgc gagcggtgaa     360
acgcgcatca ccggccttct ggaaggcgag gacgtcatca atacgggcaa ggccatgcag     420
gcgatgggcg cccgcatccg taaggaaggc gacacctgga tcatcgatgg cgtcggcaat     480
ggcggcctcc tggcgcctga ggcgccgctc gatttcggca atgccgccac gggctgccgc     540
ctgacgatgg gcctcgtcgg ggtctacgat ttcgacagca ccttcatcgg cgacgcctcg     600
ctcacaaagc gcccgatggg ccgcgtgttg aacccgctgc gcgaaatggg cgtgcaggtg     660
aaatcggaag acggtgaccg tcttcccgtt accttgcgcg ggccgaagac gccgacgccg     720
atcacctacc gcgtgccgat ggcctccgca caggtgaagt ccgccgtgct gctcgccggc     780
ctcaacacgc ccggcatcac gacggtcatc gagccgatca tgacgcgcga tcatacggaa     840
aagatgctgc agggctttgg cgccaacctt accgtcgaga cggatgcgga cggcgtgcgc     900
accatccgcc tggaaggccg cggcaagctc accggccaag tcatcgacgt gccgggcgac     960
ccgtcctcga cggccttccc gctggttgcg gccctgcttg ttccgggctc cgacgtcacc    1020
atcctcaacg tgctgatgaa ccccacccgc accggcctca tcctgacgct gcaggaaatg    1080
ggcgccgaca tcgaagtcat caacccgcgc cttgccggcg gcgaagacgt ggcggacctg    1140
cgcgttcgct cctccacgct gaagggcgtc acggtgccgg aagaccgcgc gccttcgatg    1200
atcgacgaat atccgattct cgctgtcgcc gccgccttcg cggaaggggc gaccgtgatg    1260
aacggtctgg aagaactccg cgtcaaggaa agcgaccgcc tctcggccgt cgccaatggc    1320
ctcaagctca atggcgtgga ttgcgatgag ggcgagacgt cgctcgtcgt gcgtggccgc    1380
cctgacggca aggggctcgg caacgcctcg ggcgccgccg tcgccaccca tctcgatcac    1440
cgcatcgcca tgagcttcct cgtcatgggc ctcgtgtcgg aaaaccctgt cacggtggac    1500
gatgccacga tgatcgccac gagcttcccg gagttcatgg acctgatggc cgggctgggc    1560
gcgaagatcg aactctccga tacgaaggct gcctga                             1596
```

<210> SEQ ID NO 22
<211> LENGTH: 1160
<212> TYPE: DNA
<213> ORGANISM: Artificial Sequence
<220> FEATURE:
<223> OTHER INFORMATION: Synthetic sequence

<400> SEQUENCE: 22

```
tcgaggtcat tcatatgctt gagaagagag tcgggatagt ccaaaataaa acaaaggtaa      60
gattacctgg tcaaaagtga aaacatcagt taaaaggtgg tataaagtaa aatatcggta     120
ataaaaggtg gcccaaagtg aaatttactc ttttctacta ttataaaaat tgaggatgtt     180
tttgtcggta ctttgatacg tcatttttgt atgaattggt tttaagtttt attcgctttt     240
ggaaatgcat atctgtattt gagtcgggtt ttaagttcgt ttgcttttgt aaatacagag     300
```

```
ggatttgtat aagaaatatc tttagaaaaa cccatatgct aatttgacat aattttttgag    360 aaaaatatat attcaggcga attctcacaa tgaacaataa taagattaaa atagctttcc    420
cccgttgcag cgcatgggta tttttttctag taaaaataaa agataaaactt agactcaaaa   480 catttacaaa aacaaccccct aaagttccta agcccaaag tgctatccac gatccatagc    540
aagcccagcc caacccaacc caacccaacc caccccagtc cagccaactg acaatagtc     600 tccacacccc cccactatca ccgtgagttg tccgcacgca ccgcacgtct cgcagccaaa    660 aaaaaaaga aagaaaaaaa agaaaaagaa aaaacagcag gtgggtccgg gtcgtggggg    720
ccggaaacgc gaggaggatc gcgagccagc gacgaggccg gccctccctc cgcttccaaa    780
gaaacgcccc ccatcgccac tatatacata ccccccccctc tcctcccatc ccccaaccc    840 taccaccacc accaccacca cctccacctc ctcccccctc gctgccggac gacgagctcc    900
tcccccctcc ccctccgccg ccgccgcgcc ggtaaccacc ccgcccctct cctctttctt   960
tctccgtttt tttttccgtc tcggtctcga tctttggcct tggtagtttg ggtgggcgag   1020
aggcggcttc gtgcgcgccc agatcggtgc gcgggagggg cgggatctcg cggctggggc   1080
tctcgccggc gtggatccgg cccgatctc gcggggaatg gggctctcgg atgtagatct   1140
gcgatccgcc gttgttgggg                                              1160
```

<210> SEQ ID NO 23
<211> LENGTH: 2112
<212> TYPE: DNA
<213> ORGANISM: Artificial Sequence
<220> FEATURE:
<223> OTHER INFORMATION: Synthetic sequence

<400> SEQUENCE: 23

```
gagatgatgg ggggtttaaa atttccgccg tgctaaacaa gatcaggaag aggggaaaag    60
ggcactatgg tttatatttt tatatatttc tgctgcttcg tcaggcttag atgtgctaga   120
tctttctttc ttcttttttgt gggtagaatt tgaatccctc agcattgttc atcggtagtt   180
tttcttttca tgatttgtga caaatgcagc ctcgtgcgga gcttttttgt aggtagaagt    240
gatcaaccat ggcgcaagtt agcagaatct gcaatggtgt gcagaaccca tctcttatct    300
ccaatctctc gaaatccagt caacgcaaat ctcccttatc ggtttctctg aagacgcagc    360
agcatccacg agcttatccg atttcgtcgt cgtggggatt gaagaagagt gggatgacgt    420
taattggctc tgagcttcgt cctcttaagg tcatgtcttc tgtttccacg gcgtgcatgc    480
ttcacggtgc aagcagccgg cccgcaaccg cccgcaaatc ctctggcctt ccggaaccg    540 tccgcattcc cggcgacaag tcgatctccc accggtcctt catgttcggc ggtctcgcga   600
gcggtgaaac gcgcatcacc ggccttctgg aaggcgagga cgtcatcaat acgggcaagg   660
ccatgcaggc gatgggcgcc cgcatccgta aggaaggcga cacctggatc atcgatggcg   720
tcggcaatgg cggcctcctg gcgcctgagg cgccgctcga tttcggcaat gccgccacgg   780
gctgccgcct gacgatgggc ctcgtcgggg tctacgattt cgacagcacc ttcatcggcg   840
acgcctcgct cacaaagcgc ccgatgggcc gcgtgttgaa cccgctgcgc gaaatgggcg    900
tgcaggtgaa atcggaagac ggtgaccgtc ttcccgttac cttgcgcggg ccgaagacgc   960
cgacgccgat cacctaccgc gtgccgatgg cctccgcaca ggtgaagtcc gccgtgctgc   1020
tcgccggcct caacacgccc ggcatcacga cggtcatcga gccgatcatg acgcgcgatc   1080
atacggaaaa gatgctgcag ggctttggcg ccaaccttac cgtcgagacg gatgcggacg   1140
```

| | |
|---|---|
| gcgtgcgcac catccgcctg gaaggccgcg gcaagctcac cggccaagtc atcgacgtgc | 1200 |
| cgggcgaccc gtcctcgacg gccttcccgc tggttgcggc cctgcttgtt ccgggctccg | 1260 |
| acgtcaccat cctcaacgtg ctgatgaacc ccacccgcac cggcctcatc ctgacgctgc | 1320 |
| aggaaatggg cgccgacatc gaagtcatca acccgcgcct tgccggcggc gaagacgtgg | 1380 |
| cggacctgcg cgttcgctcc tccacgctga agggcgtcac ggtgccggaa gaccgcgcgc | 1440 |
| cttcgatgat cgacgaatat ccgattctcg ctgtcgccgc cgccttcgcg gaaggggcga | 1500 |
| ccgtgatgaa cggtctggaa gaactccgcg tcaaggaaag cgaccgcctc tcggccgtcg | 1560 |
| ccaatggcct caagctcaat ggcgtggatt gcgatgaggg cgagacgtcg ctcgtcgtgc | 1620 |
| gtggccgccc tgacggcaag gggctcggca acgcctcggg cgccgccgtc gccacccatc | 1680 |
| tcgatcaccg catcgccatg agcttcctcg tcatgggcct cgtgtcggaa aaccctgtca | 1740 |
| cggtggacga tgccacgatg atcgccacga gcttcccgga gttcatggac ctgatggccg | 1800 |
| ggctgggcgc gaagatcgaa ctctccgata cgaaggctgc ctgatgagct cgaattcccg | 1860 |
| atcgttcaaa catttggcaa taaagtttct taagattgaa tcctgttgcc ggtcttgcga | 1920 |
| tgattatcat ataatttctg ttgaattacg ttaagcatgt aataattaac atgtaatgca | 1980 |
| tgacgttatt tatgagatgg gttttttatga ttagagtccc gcaattatac atttaatacg | 2040 |
| cgatagaaaa caaaatatag cgcgcaaact aggataaatt atcgcgcgcg gtgtcatcta | 2100 |
| tgttactaga tc | 2112 |

<210> SEQ ID NO 24
<211> LENGTH: 21
<212> TYPE: DNA
<213> ORGANISM: Lachnospiraceae bacterium ND2006

<400> SEQUENCE: 24

| | |
|---|---|
| taatttctac taagtgtaga t | 21 |

<210> SEQ ID NO 25
<211> LENGTH: 946
<212> TYPE: DNA
<213> ORGANISM: Artificial
<220> FEATURE:
<223> OTHER INFORMATION: Synthetic sequence

<400> SEQUENCE: 25

| | |
|---|---|
| aagttgttta gttcgaaatg acttcgtgta tgctcgattg atctggtttt aatcttcgat | 60 |
| ctgttaggtg ttgatgttta caagtgaatt ctagtgtttt ctcgttgaga tctgtgaagt | 120 |
| ttgaacctag ttttctcaat aatcaacata tgaagcgatg tttgagtttc aataaacgct | 180 |
| gctaatcttc gaaactaagt tgtgatctga ttcgtgttta cttcatgagc ttatccaatt | 240 |
| catttcggtt tcattttact ttttttttag tgaaccatgg cgcaagttag cagaatctgc | 300 |
| aatggtgtgc agaacccatc tcttatctcc aatctctcga atccagtca acgcaaatct | 360 |
| cccttatcgg tttctctgaa gacgcagcag catccacgag cttatccgat tcgtcgtcg | 420 |
| tggggattga agaagagtgg gatgacgtta attggctctg agcttcgtcc tcttaaggtc | 480 |
| atgtcttctg tttccacggc gtgcatgggg aagcggtga tcgccgaagt atcgactcaa | 540 |
| ctatcagagg tagttggcgt catcgagcgc catctcgaac cgacgttgct ggccgtacat | 600 |
| ttgtacggct ccgcagtgga tggcggcctg aagccacaca gtgatattga tttgctggtt | 660 |
| acggtgaccg taaggcttga tgaaacaacg cggcagctt tgatcaacga ccttttggaa | 720 |
| acttcggctt cccctggaga gagcgagatt ctccgcgctg tagaagtcac cattgttgtg | 780 |

| | |
|---|---|
| cacgacgaca tcattccgtg gcgttatcca gctaagcgcg aactgcaatt tggagaatgg | 840 |
| cagcgcaatg acattcttgc aggtatcttc gagccagcca cgatcgacat tgatctggct | 900 |
| atcttgctga caaaagcaag agaacatagc gttgccttgg taggtc | 946 |

<210> SEQ ID NO 26
<211> LENGTH: 6062
<212> TYPE: DNA
<213> ORGANISM: Artificial Sequence
<220> FEATURE:
<223> OTHER INFORMATION: Synthetic sequence

<400> SEQUENCE: 26

| | |
|---|---|
| gtcgtgcccc tctctagaga taaagagcat tgcatgtcta aagtataaaa aattaccaca | 60 |
| tattttttg tcacacttat ttgaagtgta gtttatctat ctctatacat atatttaaac | 120 |
| ttcactctac aaataatata gtctataata ctaaataat attagtgttt tagaggatca | 180 |
| tataaataaa ctgctagaca tggtctaaag gataattgaa tattttgaca atctacagtt | 240 |
| ttatctttt agtgtgcatg tgatctctct gttttttttg caaatagctt gacctatata | 300 |
| atacttcatc cattttatta gtacatccat ttaggattta gggttgatgg tttctataga | 360 |
| ctaatttta gtacatccat tttattctt ttagtctcta aatttttaa aactaaaact | 420 |
| ctattttagt tttttattta ataatttaga tataaaatga aataaaataa attgactaca | 480 |
| aataaaacaa atacccttta agaaataaaa aaactaagca acatttttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| acccctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acgggggatt cctttcccac cgctccttcg cttccctc ctcgcccgcc | 840 |
| gtaataaata gacacccct ccacaccctc tttccccaac ctcgtgttcg ttcggagcgc | 900 |
| acacacacgc aaccagatct cccccaaatc cagccgtcgg cacctccgct tcaaggtacg | 960 |
| ccgctcatcc tcccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt taagatgatg gatggaaata tcgatctagg ataggtatac atgttgatgc | 1260 |
| gggttttact gatgcatata cagagatgct ttttttctcg cttggttgtg atgatatggt | 1320 |
| ctggttgggc ggtcgttcta gatcggagta gaatactgtt tcaaactacc tggtggattt | 1380 |
| attaaaggat aaagggtcgt tctagatcgg agtagaatac tgtttcaaac tacctggtgg | 1440 |
| atttattaaa ggatctgtat gtatgtgcct acatcttcat agttacgagt ttaagatgat | 1500 |
| ggatggaaat atcgatctag gataggtata catgttgatg cgggttttac tgatgcatat | 1560 |
| acagagatgc ttttttcgc ttggttgtga tgatgtggtc tggttgggcg gtcgttctag | 1620 |
| atcggagtag aatactgttt caaactacct ggtggattta ttaattttgt atctttatgt | 1680 |
| gtgtgccata catcttcata gttacgagtt taagatgatg gatggaaata ttgatctagg | 1740 |
| ataggtatac atgttgatgt gggttttact gatgcatata catgatggca tatgcggcat | 1800 |
| ctattcatat gctctaacct tgagtaccta tctattataa taaacaagta tgttttataa | 1860 |

```
ttattttgat cttgatatac ttggatgatg gcatatgcag cagctatatg tggattttt       1920
agccctgcct tcatacgcta tttatttgct tggtactgtt tcttttgtcc gatgctcacc       1980
ctgttgtttg gtgatacttc tgcaggtcgc cgccatggcg ggatctaaga agagaagaat       2040
taaacaagat tcgaagctcg agaagttcac caactgctac tcgctgagca agacgctgcg       2100
gttcaaggcg atccccgtcg ggaagaccca ggagaacatc gacaacaagc ggctcctggt       2160
cgaggacgag aagcgcgccg aggactacaa gggcgtcaag aagctgctgg accggtacta       2220
cctctccttc atcaacgacg tcctgcactc gatcaagctc aagaacctga caactacat        2280
ctcgctgttc cgcaagaaga cacggaccga aaggagaac aaggagctcg agaacctcga        2340
gatcaacctg cgcaaggaga tcgcgaaggc gttcaagggc aacgaggggt acaagagcct       2400
gttcaagaaa gacatcatcg agaccatcct gccggagttc ctggacgaca aggacgagat       2460
cgcgctggtg aactcgttca cgggttcac cacggccttc accgggtttt tcgacaaccg        2520
ggagaacatg ttcagcgagg aggccaagtc gaccagcatc gccttccggt gcatcaacga       2580
gaacctcacc cgctacatca gcaacatgga catcttcgag aaggtggacg ccatcttcga      2640
caagcacgag gtccaggaga tcaaggaaaa gatcctgaac tcggactacg acgtggaaga       2700
cttctttgag ggcgagttct tcaacttcgt cctcacccag gagggcatcg acgtctacaa       2760
cgccatcatc ggcggcttcg tgacggagag cggcgagaag atcaagggcc tcaacgagta      2820
catcaacctc tacaaccaga agactaagca gaagctcccg aagttcaagc cgctgtacaa      2880
gcaagtcctg agcgaccggg agtccctctc gttctacggc gagggctaca cgagcgacga      2940
ggaggtgctg gaggtgttcc gcaacacgct gaacaagaac agcgagatct tcagctcgat       3000
caagaaactc gagaagctgt tcaagaactt cgacgagtac agcagcgccg gcatcttcgt       3060
caagaacggg cccgcgatca gcaccatcag caaggacatc ttcggggagt ggaacgtgat       3120
ccgcgacaag tggaacgccg agtacgacga catccacctc aagaaaaagg cggtggtcac       3180
ggagaagtac gaggacgacc gccggaagtc cttcaagaaa atcggagct tcagcctcga       3240
gcagctccag gagtacgcgg acgccgacct gagcgtggtg gagaagctca aggagatcat       3300
catccagaag gtcgacgaga tctacaaggt ctacggctcg agcgagaagc tgttcgacgc       3360
ggacttcgtg ctggagaagt ccctcaagaa gaacgacgcc gtggtggcca tcatgaagga       3420
tctgctcgac agcgtgaagt cgttcgagaa ctacatcaag gcattctttg ggagggcaa       3480
ggagacgaac cgggacgagt ccttctacgg ggacttcgtg ctcgcgtacg acatcctcct      3540
gaaggtcgac cacatctacg acgcgatccg gaactacgtc acgcagaagc cctacagcaa      3600
ggacaagttc aagctctact tccagaaccc gcagttcatg ggcgggtggg acaaggacaa      3660
ggagaccgac taccgggcca cgatcctgcg gtacgggtcc aagtactacc tcgccatcat       3720
ggacaagaag tacgccaagt gcctccagaa gattgacaag gacgacgtga acgggaacta      3780
cgagaagatc aactacaagc tcctcccggg gcccaacaag atgctgccga aggtgttctt       3840
cagcaagaag tggatggcct actacaaccc ctcggaggac atccagaaga tatacaagaa      3900
cggcacgttc aaaaagggg acatgttcaa cctgaacgac tgccacaagc tgatcgactt       3960
tttcaaggac agcatcagcc gctacccgaa gtggtcgaac gcctacgact tcaacttctc       4020
ggagacggag aagtacaagg acattgcggg cttctaccgg gaggtggagg agcagggcta      4080
caaggtctcc ttcgagagcg cctccaagaa agaggtggac aagctcgtgg aggagggcaa      4140
gctgtacatg ttccagatct acaacaagga cttctcggac aagtcgcacg caccccgaa       4200
cctccacacg atgtacttca agctgctgtt cgacgagaac aaccacgggc agatccgcct       4260
```

```
cagcggcggg gcggagctgt tcatgcgccg cgcgtccctc aagaaggagg agctggtcgt    4320
gcaccccgcc aactcccega tcgcgaacaa gaacccegac aaccccaaga agacaaccac    4380
cctctcgtac gacgtctaca aggacaagcg gttctcggag gaccagtacg agctgcacat    4440
cccgatcgcc atcaacaagt gccccaagaa catcttcaag atcaacaccg aggtgcgggt    4500
gctgctcaag cacgacgaca acccctacgt catcgggatc gaccgcggcg agcggaacct    4560
gctctacatc gtggtcgtgg acgggaaggg aacatcgtg gagcagtaca gcctgaacga    4620
gatcatcaac aacttcaacg gcatccgcat caagacggac taccacagcc tcctggacaa    4680
gaaggagaag gagcggttcg aggcgcggca gaactgacc tccatcgaga acatcaagga    4740
gctgaaggcc ggctacatca gccaggtcgt gcacaagatc tgcgagctcg tggagaagta    4800
cgacgcggtg atcgcgctgg aggacttgaa cagcgggttc aagaactccc gggtcaaggt    4860
cgagaagcag gtctaccaga agttcgagaa gatgctgatc gacaagctca actacatggt    4920
ggacaagaag tccaacccct gcgccaccgg cggcgccctc aagggctacc agatcaccaa    4980
caagttcgag tccttcaagt cgatgtctac gcagaacggg ttcattttct acatcccggc    5040
gtggctcacc agcaagatcg acccgagcac gggcttcgtc aacctcctga agaccaagta    5100
caccagcatc gcggacagca agaagttcat ctcctcgttc gaccgcatca tgtacgtccc    5160
cgaggaagac ctgttcgagt tcgccctcga ctacaagaac ttctcccgga cggacgccga    5220
ctacatcaaa aagtggaagc tctacagcta cggcaaccgg atccgcatct tccgcaaccc    5280
caagaagaac aatgtgttcg actgggagga ggtgtgcctg acgagcgcct acaaggagct    5340
cttcaacaag tacggcatca actaccagca agggacatc cgcgcgctgc tctgcgagca    5400
gtccgacaag gcgttctact cgtcgttcat ggccctgatg agcctcatgc tccagatgcg    5460
caacagcatc accggccgga cggacgtgga cttcctgatc agcccggtca agaacagcga    5520
cggcattttc tacgacagcc ggaactacga ggcccaggag aacgccatcc tccccaagaa    5580
cgccgacgcg aacggcgcct acaacatcgc gcggaaggtg ctgtgggcca tcggccagtt    5640
taaaaaggcg gaggacgaga agctggacaa ggtcaagatc gccatcagca acaaggagtg    5700
gctcgagtac gcgcagacga gcgtgaagca cggatctaag aagagaagaa ttaaacaaga    5760
ttgataatcg atcctccgat cccttaatta ccataccatt acaccatgca tcaatatcca    5820
tatatatata aacccttcg cacgtactta tactatgttt tgtcatacat atatatgtgt    5880
cgaacgatcg atctatcact gatatgatat gattgatcca tcagcctgat ctctgtatct    5940
tgttatttgt ataccgtcaa ataaaagttt cttccacttg tgttaataat tagctactct    6000
catctcatga accctatata taactagttt aatttgctgt caattgaaca tgatgatcga    6060
tg                                                                  6062
```

<210> SEQ ID NO 27
<211> LENGTH: 23
<212> TYPE: DNA
<213> ORGANISM: Glycine max

<400> SEQUENCE: 27
gcaacaccaa ttaacagttc aat                                              23

<210> SEQ ID NO 28
<211> LENGTH: 23
<212> TYPE: DNA
<213> ORGANISM: Artificial Sequence
<220> FEATURE:

<223> OTHER INFORMATION: Synthetic sequence

<400> SEQUENCE: 28
gcaacaccaa ttaacagtta ttg 23

<210> SEQ ID NO 29
<211> LENGTH: 23
<212> TYPE: DNA
<213> ORGANISM: Artificial Sequence
<220> FEATURE:
<223> OTHER INFORMATION: Synthetic sequence

<400> SEQUENCE: 29
gtataatatg atggcatgca ttg 23

<210> SEQ ID NO 30
<211> LENGTH: 23
<212> TYPE: DNA
<213> ORGANISM: Glycine max

<400> SEQUENCE: 30
gtccgggttg atatggtgaa aga 23

<210> SEQ ID NO 31
<211> LENGTH: 23
<212> TYPE: DNA
<213> ORGANISM: Artificial Sequence
<220> FEATURE:
<223> OTHER INFORMATION: Synthetic sequence

<400> SEQUENCE: 31
gtccgggttg atatggtgat ctt 23

<210> SEQ ID NO 32
<211> LENGTH: 23
<212> TYPE: DNA
<213> ORGANISM: Artificial Sequence
<220> FEATURE:
<223> OTHER INFORMATION: Synthetic sequence

<400> SEQUENCE: 32
gtataatatg atggcatgct ctt 23

<210> SEQ ID NO 33
<211> LENGTH: 5856
<212> TYPE: DNA
<213> ORGANISM: Artificial Sequence
<220> FEATURE:
<223> OTHER INFORMATION: Synthetic sequence

<400> SEQUENCE: 33
actgttaata atttttaaac gtcagcgcac taaaaaaacg aaaagacgga cacgtgaaaa 60
taaaaaacac acactagttt atgacgcaat actattttac ttatgatttg ggtacattag 120
acaaaaccgt gaaagagatg tatcagctat gaaacctgta tacttcaata cagagacgta 180
ctcatatcgg atacgtacgc acgaagtatc atattaatta ttttaatttt taataaatat 240
tttatcggat acttatgtga tactctacat atacacaagg atatttctaa gatactttat 300
agatacgtat cctagaaaaa catgaagagt aaaaaagtga gacaatgttg taaaaattca 360
ttataaatgt atatgattca attttagata tgcatcagta taattgattc tcgatgaaac 420
acttaaaatt atatttcttg tggaagaacg tagcgagaga ggtgattcag ttagacaaca 480
ttaaataaaa ttaatgttaa gttcttttaa tgatgtttct ctcaatatca catcatatga 540

```
aaatgtaata tgatttataa gaaaattttt aaaaaattta ttttaataat cacatgtact    600 atttttaaa  aattgtatct  tttataataa  tacaataata  aagagtaatc  agtgttaatt    660
tttcttcaaa tataagtttt attataaatc attgttaacg tatcataagt cattaccgta    720
tcgtatctta attttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagc tgccgttggc gtaatataac    960
agccaatcga ttttgctat  aaaagcaaat caggtaaact aaacttcttc attcttttct   1020
tccccatcgc tacaaaaccg gttcctttgg aaaagagatt cattcaaacc tagcacccaa   1080
ttccgtttca aggtataatc tactttctat tcttcgatta ttttattatt attagctact   1140
atcgtttaat cgatcttttc ttttgatccg tcaaatttaa attcaattag gttttgttc    1200 ttttctttca tctgattgaa atccttctga attgaaccgt ttacttgatt ttactgttta   1260
ttgtatgatt taatcctttg tttttcaaag acagtcttta gattgtgatt aggggttcat   1320 ataaatttt  agatttggat ttttgtattg tatgattcaa aaaatacgtc ctttaattag   1380
attagtacat ggatatttt  tacccgattt attgattgtc agggagaatt tgatgagcaa   1440
gtttttttga tgtctgttgt aaattgaatt gattataatt gctgatctgc tgcttccagt   1500
tttcataacc catattcttt taaccttgtt gtacacacaa tgaaaaattg gtgattgatt   1560
catttgtttt tctttgtttt ggattataca gggtaccaaa aaatggcggg atctaagaag   1620
agaagaatta acaagattc  gaagctcgag aagttcacca actgctactc gctgagcaag   1680
acgctgcggt tcaaggcgat ccccgtcggg aagacccagg agaacatcga caacaagcgg   1740
ctcctggtcg aggacgagaa gcgcgccgag gactacaagg gcgtcaagaa gctgctggac   1800
cggtactacc tctccttcat caacgacgtc ctgcactcga tcaagctcaa gaacctgaac   1860
aactacatct cgctgttccg caagaagaca cggaccgaga aggagaacaa ggagctcgag   1920
aacctcgaga tcaacctgcg caaggagatc gcgaaggcgt tcaagggcaa cgaggggtac   1980
aagagcctgt tcaagaaaga catcatcgag accatcctgc cggagttcct ggacgacaag   2040
gacgagatcg cgctggtgaa ctcgttcaac gggttcacca cggccttcac cgggtttttc   2100
gacaaccggg agaacatgtt cagcgaggag gccaagtcga ccagcatcgc cttccggtgc   2160
atcaacgaga acctcacccg ctacatcagc aacatggaca tcttcgagaa ggtggacgcc   2220
atcttcgaca agcacgaggt ccaggagatc aaggaaaaga tcctgaactc ggactacgac   2280
gtggaagact tctttgaggg cgagttcttc aacttcgtcc tcacccagga gggcatcgac   2340
gtctacaacg ccatcatcgg cggcttcgtg acggagagcg gcgagaagat caagggcctc   2400
aacgagtaca tcaacctcta caaccagaag actaagcaga agctcccgaa gttcaagccg   2460
ctgtacaagc aagtcctgag cgaccgggag tccctctcgt tctacggcga gggctacacg   2520
agcgacgagg aggtgctgga ggtgttccgc aacacgctga caagaacag cgagatcttc    2580 agctcgatca agaaactcga gaagctgttc aagaacttcg acgagtacag cagcgccggc   2640
atcttcgtca gaacgggcc  cgcgatcagc accatcagca aggacatctt cggggagtgg   2700
aacgtgatcc gcgacaagtg gaacgccgag tacgacgaca tccacctcaa gaaaaaggcg   2760
gtggtcacgg agagtacga  ggacgaccgc cggaagtcct tcaagaaaat cgggagcttc   2820
agcctcgagc agctccagga gtacgcggac gccgacctga gcgtggtgga aagctcaag    2880
```

```
gagatcatca tccagaaggt cgacgagatc tacaaggtct acggctcgag cgagaagctg    2940
ttcgacgcgg acttcgtgct ggagaagtcc ctcaagaaga cgacgccgt ggtggccatc    3000 atgaaggatc tgctcgacag cgtgaagtcg ttcgagaact acatcaaggc attctttggg    3060
gagggcaagg agacgaaccg ggacgagtcc ttctacgggg acttcgtgct cgcgtacgac    3120
atcctcctga aggtcgacca catctacgac gcgatccgga actacgtcac gcagaagccc    3180
tacagcaagg acaagttcaa gctctacttc cagaacccgc agttcatggg cgggtgggac    3240
aaggacaagg agaccgacta ccgggccacg atcctgcggt acgggtccaa gtactacctc    3300
gccatcatgg acaagaagta cgccaagtgc ctccagaaga ttgacaagga cgacgtgaac    3360
gggaactacg agaagatcaa ctacaagctc ctcccggggc ccaacaagat gctgccgaag    3420
gtgttcttca gcaagaagtg gatggcctac acaaccccct cggaggacat ccagaagata    3480
tacaagaacg gcacgttcaa aaagggggac atgttcaacc tgaacgactg ccacaagctg    3540
atcgactttt tcaaggacag catcagccgc tacccgaagt ggtcgaacgc ctacgacttc    3600
aacttctcgg agacggagaa gtacaaggac attgcgggct tctaccggga ggtggaggag    3660
cagggctaca aggtctcctt cgagagcgcc tccaagaaag aggtggacaa gctcgtggag    3720
gagggcaagc tgtacatgtt ccagatctac aacaaggact tctcggacaa gtcgcacggc    3780
accccgaacc tccacacgat gtacttcaag ctgctgttcg acgagaacaa ccacgggcag    3840
atccgcctca gcggcggggc ggagctgttc atggccgcg cgtccctcaa gaaggaggag    3900
ctggtcgtgc accccgccaa ctccccgatc gcgaacaaga ccccgacaa ccccaagaag    3960 acaaccaccc tctcgtacga cgtctacaag gacaagcggt tctcggagga ccagtacgag    4020
ctgcacatcc cgatcgccat caacaagtgc cccaagaaca tcttcaagat caacaccgag    4080
gtgcgggtgc tgctcaagca cgacgacaac ccctacgtca tcgggatcga ccgcggcgag    4140
cggaacctgc tctacatcgt ggtcgtggac gggaagggga acatcgtgga gcagtacagc    4200
ctgaacgaga tcatcaacaa cttcaacggc atccgcatca agacggacta ccacagcctc    4260
ctggacaaga aggagaagga gcggttcgag gcgcggcaga actggaccctc catcgagaac    4320 atcaaggagc tgaaggccgg ctacatcagc caggtcgtgc acaagatctg cgagctcgtg    4380
gagaagtacg acgcggtgat cgcgctggag gacttgaaca gcgggttcaa gaactcccgg    4440
gtcaaggtcg agaagcaggt ctaccagaag ttcgagaaga tgctgatcga caagctcaac    4500
tacatggtgg acaagaagtc caaccccctgc gccaccggcg gcgccctcaa gggctaccag    4560
atcaccaaca agttcgagtc cttcaagtcg atgtctacgc agaacgggtt catttttctac    4620 atcccggcgt ggctcaccag caagatcgac ccgagcacgg gcttcgtcaa cctcctgaag    4680
accaagtaca ccagcatcgc ggacagcaag aagttcatct cctcgttcga ccgcatcatg    4740
tacgtccccg aggaagacct gttcgagttc gccctcgact acaagaactt ctccccggacg    4800 gacgccgact acatcaaaaa gtggaagctc tacagctacg gcaaccggat ccgcatcttc    4860 cgcaaccccca agaagaacaa tgtgttcgac tgggaggagg tgtgcctgac gagcgcctac    4920
aaggagctct tcaacaagta cggcatcaac taccagcaag gggacatccg cgcgctgctc    4980
tgcgagcagt ccgacaaggc gttctactcg tcgttcatgg ccctgatgag cctcatgctc    5040
cagatgcgca acagcatcac cggccggacg gacgtggact tcctgatcag cccggtcaag    5100
aacagcgacg gcattttcta cgacagccgg aactacgagg cccaggagaa cgccatcctc    5160
cccaagaacg ccgacgcgaa cggcgcctac aacatcgcgc ggaaggtgct gtgggccatc    5220
ggccagttta aaaggcgga ggacgagaag ctggacaagg tcaagatcgc catcagcaac    5280
```

```
aaggagtggc tcgagtacgc gcagacgagc gtgaagcacg gatctaagaa gagaagaatt    5340
aaacaagatt gattaattaa tcatctgaaa ctgttcacca tgcatgcaat cttgtgaaat    5400
atatggtttt aattagactt caatcttatg ttggctattg tactaataaa agcatgtcat    5460
gttattttca tttgatttta tctgtacttt ggtttgtttg aagaataaag atgagcttgc    5520
tatgcatgca tgcatgccat cgattatcag ggtttccttt tttctttttct ggcttcccat   5580 caatttggtg tgaattagtg tgtgtgatat attatattat gctatttatg aaataaattg    5640
ttggttatat ttgatctaca atctacatac atgtgatttt tatcaacaaa atatctcggg    5700
aaacaatacc ttttttggtag caaaattcaa ataatactat tttaaataaa tcaaagttaa   5760 ccaataccttt attcaagttg gaggggtctc aaacaagcaa agaattcaa gttgttaatg    5820 aacttcggtt aatgataaaa gaattcgcat ttaaaa                              5856

<210> SEQ ID NO 34
<211> LENGTH: 427
<212> TYPE: DNA
<213> ORGANISM: Glycine max

<400> SEQUENCE: 34
cgataaaaat gttttaaacg atatatatta taaaaaaaaa cgtttcaaaa ataaatacaa      60
aaatgttttt aaatatatat aatttaactc attaaagaaa ataaaatgc aagtgcggtg     120 acaagacaag ctaaaagttg caaaagaaat ggcagggcta taaggctcac ctactcctgg    180
atttaccaaa ttttggttcg tccctatact cgaaaaataa aacaaaataa atttcagtat    240
cttcgttttt gtatgctttg actgtgaggc gaggccaact ttcttcttct gtctgagatg    300
aattttgttt gcctcctgtg aaggatgtat cattcaaagt gaatgtttg caactgccag     360 tagtcccaca tcgaccaaat attcttatta cagtgtgttt atatagcacc tggagaagga    420
atgggtt                                                              427

<210> SEQ ID NO 35
<211> LENGTH: 200
<212> TYPE: DNA
<213> ORGANISM: Zea mays

<400> SEQUENCE: 35
cggcgtatgt gccaaaaact tcgtcacaga gagggccata agaaacatgg cccacggccc      60
aatacgaagc accgcgacga agcccaaaca gcagtccgta ggtggagcaa agcgctgggt    120
aatacgcaaa cgttttgtcc caccttgact aatcacaaga gtggagcgta ccttataaac    180
cgagccgcaa gcaccgaatt                                                200

<210> SEQ ID NO 36
<211> LENGTH: 930
<212> TYPE: DNA
<213> ORGANISM: Erwinia herbicola

<400> SEQUENCE: 36
atgagccaac cgccgctgct tgaccacgcc acgcagacca tggccaacgg ctcgaaaagt      60
tttgccaccg ctgcgaagct gttcgacccg gccaccgcc gtagcgtgct gatgctctac     120
acctggtgcc gccactgcga tgacgtcatt gacgaccaga cccacggctt cgccagcgag    180
gccgcggcgg aggaggaggc cacccagcgc ctggcccggc tgcgcacgct gacctggcg     240 gcgtttgaag gggccgagat gcaggacccg gccttcgctg cctttcagga ggtggcgctg    300
```

```
acccacggta ttacgccccg catggcgctc gatcacctcg acggctttgc gatggacgtg    360
gctcagaccc gctatgtcac ctttgaggat acgctgcgct actgctatca cgtggcgggc    420
gtggtgggtc tgatgatggc cagggtgatg ggcgtgcggg atgagcgggt gctggatcgc    480
gcctgcgatc tggggctggc cttccagctg acgaatatcg cccgggatat tattgacgat    540
gcggctattg accgctgcta tctgcccgcc gagtggctgc aggatgccgg gctgaccccg    600
gagaactatg ccgcgcggga gaatcgggcc gcgctgcgc gggtggcgga gcggcttatt    660
gatgccgcag agccgtacta catctcctcc caggccgggc tacacgatct gccgccgcgc    720
tgcgcctggg cgatcgccac cgcccgcagc gtctaccggg agatcggtat taaggtaaaa    780
gcggcgggag gcagcgcctg ggatcgccgc cagcacacca gcaaaggtga aaaaattgcc    840
atgctgatgg cggcaccggg gcaggttatt cgggcgaaga cgacgagggt gacgccgcgt    900
ccggccggtc tttggcagcg tcccgtttag                                     930
```

```
<210> SEQ ID NO 37
<211> LENGTH: 15
<212> TYPE: DNA
<213> ORGANISM: Artificial Sequence
<220> FEATURE:
<223> OTHER INFORMATION: Synthetic sequence

<400> SEQUENCE: 37
cattagacca ttgcc                                                      15

<210> SEQ ID NO 38
<211> LENGTH: 15
<212> TYPE: DNA
<213> ORGANISM: Artificial Sequence
<220> FEATURE:
<223> OTHER INFORMATION: Synthetic sequence

<400> SEQUENCE: 38
gtaatctggt aacgg                                                      15

<210> SEQ ID NO 39
<211> LENGTH: 16
<212> TYPE: DNA
<213> ORGANISM: Artificial Sequence
<220> FEATURE:
<223> OTHER INFORMATION: Synthetic sequence

<400> SEQUENCE: 39
accttcgcca ttcgag                                                     16

<210> SEQ ID NO 40
<211> LENGTH: 16
<212> TYPE: DNA
<213> ORGANISM: Artificial Sequence
<220> FEATURE:
<223> OTHER INFORMATION: synthetic sequence

<400> SEQUENCE: 40
tggaagcggt aagctc                                                     16

<210> SEQ ID NO 41
<211> LENGTH: 20
<212> TYPE: DNA
<213> ORGANISM: Artificial Sequence
<220> FEATURE:
<223> OTHER INFORMATION: synthetic sequence

<400> SEQUENCE: 41
```
cattagacca gccattcgag                                                           20

<210> SEQ ID NO 42
<211> LENGTH: 20
<212> TYPE: DNA
<213> ORGANISM: Artificial Sequence
<220> FEATURE:
<223> OTHER INFORMATION: Synthetic sequence

<400> SEQUENCE: 42
gtaatctggt cggtaagctc                                                           20

<210> SEQ ID NO 43
<211> LENGTH: 16
<212> TYPE: DNA
<213> ORGANISM: Artificial Sequence
<220> FEATURE:
<223> OTHER INFORMATION: synthetic sequence

<400> SEQUENCE: 43
cattagacca ttcgag                                                               16

<210> SEQ ID NO 44
<211> LENGTH: 16
<212> TYPE: DNA
<213> ORGANISM: Artificial Sequence
<220> FEATURE:
<223> OTHER INFORMATION: Synthetic sequence

<400> SEQUENCE: 44
gtaatctggt aagctc                                                               16

<210> SEQ ID NO 45
<211> LENGTH: 12
<212> TYPE: DNA
<213> ORGANISM: Artificial Sequence
<220> FEATURE:
<223> OTHER INFORMATION: synthetic sequence

<400> SEQUENCE: 45
gtaatctggt aa                                                                   12

<210> SEQ ID NO 46
<211> LENGTH: 10
<212> TYPE: DNA
<213> ORGANISM: Artificial Sequence
<220> FEATURE:
<223> OTHER INFORMATION: Synthetic sequence

<400> SEQUENCE: 46
gtaatctggt                                                                      10

<210> SEQ ID NO 47
<211> LENGTH: 35
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (32)..(35)
<223> OTHER INFORMATION: n is a, c, g, or t

```
<400> SEQUENCE: 47
nnnntttvgt ggtctccaga tttatgaagt tnnnn                              35

<210> SEQ ID NO 48
<211> LENGTH: 35
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (32)..(35)
<223> OTHER INFORMATION: n is a, c, g, or t

<400> SEQUENCE: 48
nnnnaaabca ccagaggtct aaatacttca annnn                              35

<210> SEQ ID NO 49
<211> LENGTH: 27
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(4)
<223> OTHER INFORMATION: n is a, c, g, or t

<400> SEQUENCE: 49
nnnntttvgt ggtctccaga tttatga                                       27

<210> SEQ ID NO 50
<211> LENGTH: 31
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(4)
<223> OTHER INFORMATION: n is a, c, g, or t

<400> SEQUENCE: 50
nnnnaaabca ccagaggtct aaatacttca a                                  31

<210> SEQ ID NO 51
<211> LENGTH: 31
<212> TYPE: DNA
<213> ORGANISM: Artificial Sequence
<220> FEATURE:
<223> OTHER INFORMATION: syntheitc sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 51
nntttvgtgg tctccagatt tatgaagttn n                                  31

<210> SEQ ID NO 52
<211> LENGTH: 31
```

```
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 52
nnaaabcacc agaggtctaa atacttcaan n                                31

<210> SEQ ID NO 53
<211> LENGTH: 25
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t

<400> SEQUENCE: 53
nntttvgtgg tctccagatt tatga                                      25

<210> SEQ ID NO 54
<211> LENGTH: 29
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t

<400> SEQUENCE: 54
nnaaabcacc agaggtctaa atacttcaa                                  29

<210> SEQ ID NO 55
<211> LENGTH: 31
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t

<400> SEQUENCE: 55
nntttvgtgg tctctggaga ccacbaaann n                               31

<210> SEQ ID NO 56
<211> LENGTH: 31
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
```

```
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t

<400> SEQUENCE: 56
nnaaabcacc agagacctct ggtgvtttnn n                                            31

<210> SEQ ID NO 57
<211> LENGTH: 31
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (5)..(23)
<223> OTHER INFORMATION: n is a, c, g, or t
<220> FEATURE:
<221> NAME/KEY: misc_feature
<222> LOCATION: (28)..(31)
<223> OTHER INFORMATION: n is a, c, g, or t

<400> SEQUENCE: 57
tttvnnnnnn nnnnnnnnnn nnnagtcnnn n                                            31

<210> SEQ ID NO 58
<211> LENGTH: 31
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (5)..(23)
<223> OTHER INFORMATION: n is a, c, g, or t
<220> FEATURE:
<221> NAME/KEY: misc_feature
<222> LOCATION: (28)..(31)
<223> OTHER INFORMATION: n is a, c, g, or t

<400> SEQUENCE: 58
aaabnnnnnn nnnnnnnnnn nnntcagnnn n                                            31

<210> SEQ ID NO 59
<211> LENGTH: 31
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (5)..(23)
<223> OTHER INFORMATION: n is a, c, g, or t
<220> FEATURE:
<221> NAME/KEY: misc_feature
<222> LOCATION: (28)..(31)
<223> OTHER INFORMATION: n is a, c, g, or t

<400> SEQUENCE: 59
tttvnnnnnn nnnnnnnnnn nnngactnnn n                                            31

<210> SEQ ID NO 60
<211> LENGTH: 31
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
```

<222> LOCATION: (5)..(23)
<223> OTHER INFORMATION: n is a, c, g, or t
<220> FEATURE:
<221> NAME/KEY: misc_feature
<222> LOCATION: (28)..(31)
<223> OTHER INFORMATION: n is a, c, g, or t

<400> SEQUENCE: 60
aaabnnnnnn nnnnnnnnnn nnnctgannn n 31

<210> SEQ ID NO 61
<211> LENGTH: 23
<212> TYPE: DNA
<213> ORGANISM: Glycine max

<400> SEQUENCE: 61
gactttagct cctctgttga gtc 23

<210> SEQ ID NO 62
<211> LENGTH: 23
<212> TYPE: DNA
<213> ORGANISM: Artificial Sequence
<220> FEATURE:
<223> OTHER INFORMATION: Synthetic sequence

<400> SEQUENCE: 62
gactttagct cctctgttgg act 23

<210> SEQ ID NO 63
<211> LENGTH: 91
<212> TYPE: DNA
<213> ORGANISM: Artificial Sequence
<220> FEATURE:
<223> OTHER INFORMATION: Synthetic sequence

<400> SEQUENCE: 63
ttattatttc tttccttcgt tctgtcttta gactttagct cctctgttgg acttaaacaa 60
cactacatct gacctaagaa tgagcggccg c 91

<210> SEQ ID NO 64
<211> LENGTH: 291
<212> TYPE: DNA
<213> ORGANISM: Soybean chlorotic spot virus

<400> SEQUENCE: 64
caccaattcg ctccgctcta aaactctata gcaattggtg aattggtgac aatatatact 60
agaaccctca atagaacttc taatcctgtt cgcacacgtg gcggccatcc gctataatat 120
taccggatgg ccgcgcgatt ttttatggcc cttttctttt gggctcgttc ttttggaccg 180
agtgtatttg aattaaagta aagttattcc cctgtccaat gaaaatttgt ctgagtggtc 240
tagataagcc caacttggta cccaagttgg ttctaacggt tatatattca a 291

<210> SEQ ID NO 65
<211> LENGTH: 1056
<212> TYPE: DNA
<213> ORGANISM: Soybean chlorotic spot virus

<400> SEQUENCE: 65
atgccaccac caaagcgttt ccgtataaat gccaaaaact atttcctcac atatccccag 60
tgctccttat caaaagaggc tgctcttgaa caaattatct cgttgcagac acctagcagt 120
aagaagttta tcaagatagc aagagaactt cacgacgatg ggcagcctca tctccatgtc 180

| | |
|---|---|
| ctgcttcaat tcgaagggaa gttctgctgc acaaataaca gattgttcga cttggtttcc | 240 |
| ccaacaaggt cagcacattt ccatccaaac atacagggag ctaagtcgag ctccgacgtc | 300 |
| aagtcctacg tcgacaagga tggagacacc attgaatggg gagaattcca ggtcgacgct | 360 |
| cgttctgcaa gaggtggtca acagactgca aacgagtcat acgccaaggt tctgaacgca | 420 |
| gacaacctag aaagagccct tcaaatatta aagaagaac agccgaagga cttcgtcctt | 480 |
| catcaccaca acatacgctc taacctagag cgtatctttg ctaaggctcc ggagccatgg | 540 |
| gctcctccgt ttcacctctc ctcgttcact ttagttccac aggagatgca agattgggtc | 600 |
| aatgattatt tgggagagg tgccgctgcg cggccggaaa gacctattag tataataatc | 660 |
| gagggtgact ctcgaacggg gaagaccatg tgggcacgtg cgctagggtc ccataactac | 720 |
| ttgtccggtc acctcgattt caattcgcgg gtctattcaa atgatgtgca gtacaacgta | 780 |
| atagatgaca tcgcaccgca atatctaaag ttaaagcatt ggaaggaatt gataggtgct | 840 |
| caaaaagact ggcaatcaaa ctgcaaatac ggaaagccag ttcaaattaa aggaggggtt | 900 |
| ccttgcatta ctttgcaa tcctggcgag ggctccagct ataaatcttt cctcgacaaa | 960 |
| gaggaaaacg caggattgaa aggttggacc cttcacaatg cgaaattcgt cttcctcaac | 1020 |
| tcccccctct atcaaagttc aacacagagc agctaa | 1056 |

<210> SEQ ID NO 66
<211> LENGTH: 203
<212> TYPE: DNA
<213> ORGANISM: Faba bean necrotic yellow virus

<400> SEQUENCE: 66

| | |
|---|---|
| tgttttttaa acttagcgaa gcgggaaatt tcccgctctt tgttcattt agcaaaacgt | 60 |
| tgtcgttttc accttggacc aaggcgggta tagtattacc ccgccttgga acaccctcct | 120 |
| tggaactggt ataaatagat ttatttaatt cataaattaa atatggcttg ttcgaattgg | 180 |
| gttttcacac gcaacttcca agg | 203 |

<210> SEQ ID NO 67
<211> LENGTH: 837
<212> TYPE: DNA
<213> ORGANISM: Faba bean necrotic yellow virus

<400> SEQUENCE: 67

| | |
|---|---|
| atggcttgtt cgaattgggt tttcacacgc aacttccaag gagctctccc tcttctctcg | 60 |
| ttcgacgaga gagttcaata cgctgtctgg caacacgaaa gaggaactca tgaccatatc | 120 |
| cagggagtaa ttcaattgaa gaagaaagct cgattctcga ctgttaagga gataattggg | 180 |
| ggaaatcctc atgtagagaa aatgaaaggt acaattgaag aagcatcagc ttatgttcag | 240 |
| aaagaagaaa caagagttgc aggtccctgg agttatggtg acttattgaa gagaggatct | 300 |
| cacaggagga gacgatgga gagatattta gaagacccag aagaaatgca attgaaggat | 360 |
| ccagatactg ctcttcgatg taacgcgaag agattgaaag aagattttat gaaagaaaaa | 420 |
| acgaagcttc agcttcgtcc atggcagaaa gagttacacg atttaattct aactgaacca | 480 |
| gatgatcgta ctatcatctg ggtttatgga ccagatggag gagaaggaaa atcgatgttc | 540 |
| gcgaaagaat taatcaagta tggatggttt tacactgccg gaggaaagac ccaggacata | 600 |
| ctgtatatgt atgctcaaga tccagagaga aatattgcat tgatgtacc cagatgttca | 660 |
| tccgaaatga tgaactatca agcgatggag atgatgaaga atagatgctt tgcaagtacg | 720 |
| aaatatagat ctgtagatct tgttgtaat aaaaatgttc atttagttgt ttttgccaac | 780 |

```
gtggcatatg accccacaaa aataagtgag gataggattg taattatcaa ttgttga         837
```

<210> SEQ ID NO 68
<211> LENGTH: 1365
<212> TYPE: DNA
<213> ORGANISM: Setaria italica

<400> SEQUENCE: 68

```
tccccggtaa tctcctcctc cccctcccct ccgctccctg gagccctct actcgcgatc      60
tccccacgca ctagctcctg ctccagcatt tttcgagtgt ttggcgctca gatctgagcg    120
gcctggctcg agatctgcgg tttgctcatg cgttctggtc acttgcctcc ggtgctcccg    180
ccagatccgg ggcgggtacc gcgcgatccg ccagcggatc gtgcttcgtg gttggtgcta    240
gggtgttcgt ctgacgtctg tgcttgatga actccgtcct gttcctgatc tgtagcgttt    300
ctgcgtgccg atgcgtctga ttttgtgcgc acgcctgatg tgtgtttgcg ggactgccgt    360
gcgaggaggc tctctgagct acgtacctag gaatggtgac tgtgatgtgc ctgaatgcgc    420
ttacgtgttg ctggcgatgc acgagccctt ggggtgtgac tgcttgacta cttcccagct    480
ccgacgttct agtttcctgc ttgactggga gtctgggaga gcttcgtgat gctctgtcta    540
gcaagtccag atagttgcgg taactggtaa catggttgga tgaaagtcgc ggatagttaa    600
tttggtgtga ttgaactacc agagtgtaaa aatccgtgtg tggttcattc ggagagagct    660
atttggaaag catatctgca tgttaggatg tttccttgtc atgaatagct attgagcaca    720
taccacccaa aattagtgac aacttagtga tgtttcatgg caccaaatgt taggctgaaa    780
agttcagcat gtgattttttg ttgctctgca ggtcacattt tagacaacaa aaaagcttgt    840
tagattggcc agtacatgta cactactttt tcaaagcaat gctagtcttt tcctatcatg    900
tttagttata cgaatgtttg gttatggtac tttacacatt tttataaatg ttggaaacaa    960
cagtccgcaa gttatcagat tatttcttac tctctccgtt ccaaattgta ggtcgttttg   1020
acttttgtag gttcatagat attattatgc atctagatat agtgtatgtc taggtgcata   1080
ataatatcta tgaatctaga aaagtcaaaa cgacctacaa tttggaacgg agggagtaca   1140
acattagcct agtcggtgaa atgaatccca cttttgcctg gcagtaagct ctgtacatat   1200
gttgttttta ttgacttata gatgcacaaa tataaaggtt cagttgatat gccttcaaaa   1260
cttttatgtt tacgatgctt actggttccc ttgtacagct actatctagc aggatacact   1320
tgctgttaac tgataccccct ttttgctac ctcttgcagg gtagc                    1365
```

<210> SEQ ID NO 69
<211> LENGTH: 1161
<212> TYPE: DNA
<213> ORGANISM: Setaria italica

<400> SEQUENCE: 69

```
cgcttcgtaa gtccaccttt gaattttttgt ttatccatga cctttctag ctgtatgctt      60
gattgaaacg agagcgccga ttgaggaact ggtgtgggta atatgtgggg aattaatctg    120
agatttgtat cggtcgcctc ttgatggttg tgtagactgc ttagaaaaga aaattgtcat    180
ggtctcccgt gttaatttct tctatttttcg cctgctttat ctgatctggg ccctatatga    240
taaagataaa agggtttttt tttttttttgt agaggaggct cttgaggtat ggggaaaggg    300
cgatacatga gggatttgag atcccttgat cgggaatctt tgttcttcgg ctcgggttgc    360
tttgctctat gttcttgaaa ttcatcaagg ggcaacgaaa taagtggttt tacttatttt    420
```

```
tttgtttgat taggagattt gggatttggg atcttcgatt tgatctcttt gatcgaactg    480
aaccattagc gctcgattcc ctcatcattc atttgtttag tagaccttgt gctgcgttta    540
ttgaagtttt catccatcct tgattgaac tgaaccatta gtactcgatc ccctcatcat    600
tcatttgttt agtagacctt gtgctgcgtt tattaaagtt ttcatccatc attttgattg    660
cctctactag gtttcaagct cttttactag atgttgctaa ggtctgagtt ttgggtgcat    720
actattctgg ccacagatct gttggtgcgt tcagattaga ttgttgactt gtcttttagt    780
gaagatctcg agaagtagaa cagtattcgg taaaaatatt gggcttcctg aaatactaag    840
acatgatgag cgaagtagtg gtctgattct gactagtaag cctggctagc tggtgaacct    900
atcgttttaa cctcccagtt gattcctgaa ataagtttcc tgcatgttcc ctgtttctgg    960
tatgttatac atctgaaata agaggtagg acagtatatc ttttacaact agaaataggt    1020
gctgttcttt tttcttttga acaagaaagg ccatttctgc tggtgactag tcatagcttc    1080
cttccagctt tggttatgag tatgtctcat atttatcttt ctgcaaccta taatctctga    1140
atctctccgt tgcagggttc c                                              1161

<210> SEQ ID NO 70
<211> LENGTH: 1025
<212> TYPE: DNA
<213> ORGANISM: Coix lacryma-jobi

<400> SEQUENCE: 70
acttcggtac gtgctcgctc ctcgctctag ctttgttact gccacgtttc cctgaatgct     60
tagagcccct tgtttgctct ggagtggttt agttggatct acagattaaa ctatgaaatc    120
gtgttctctc tgtgctgatt gagtactgtg ctttgtagca gcaaaattag ggtcatggta    180
ggacgaaagc ttagtggtat gtatagtata ggcacctgtt gctgttatag gacaattaga    240
ttctgaagtt tgctgtcaag tttgcgataa ggattcatac tatagttctg cttagtgtta    300
tttaagcacc tgttgctgtt ttagggcact tagattcaga agtttgctgt taaactcgcg    360
atacggtttc atactatagt tctgcttagt gttatttaag cacctgttgc tgttataggg    420
cacttagatt cagaagtttg ctgttaaact cgcgatacgg tttcatactg tataggtgaa    480
tagtatagcg attcatacta tatataggtg aatatgaata ctataattgg ttcgtctgca    540
gagcttatta tttgccaaaa ttagatactc ctaatctgtt cttgtttgcg tgctgttaaa    600
ttgttagtgg ctgaaataaa tattgtaata attgacgtaa ttttgatgtt tatccctgct    660
tgtctgttgt ggcgaaatta aggtgaagtg tccttgttgt aaattattgt tgcctgaaga    720
aacaagtaac tgacagtatt ttgatgcatt gacctgctca tttgttgtga caaataaaga    780
agaaggtgtt ctgttgctat aataatattt ttgttgctct gcttgccttt tgtagttctg    840
ttagtatctg agaaacgcag taaaatgatg atgcttgttt tttttcatat tgtagctcta    900
cactgttttc agttataatg cccacaatta gttgaactga ttggaagata tcttatgctt    960
tctccctatt gctaccact gttactcaca caaccttgc tcatttcatt gtgatgcagg    1020
tgccg                                                                1025

<210> SEQ ID NO 71
<211> LENGTH: 1801
<212> TYPE: DNA
<213> ORGANISM: Setaria italica

<400> SEQUENCE: 71
actctggtga gcacctcctc gatccccctc gctacttgct cttcgtcaga tctgtttttgt     60
```

```
ttggcgcgac ttgtacttcg atctggtcga tctgtcgctg ctttggctgg atctgtgtta    120
gtgctaggtt tgtttatgct gttggtcaga tccaatatag tttttgcttg gatctagcat    180
agttcctttt gacttagatc cgttactagt tgtattaagt ttgtgttggt atcgagatcc    240
gtagtctgta gcacctagtc gtgtgtggcc agatgccata atttttttata gtacctgaca    300 tcaacacttc aatctgttgt tacagtagat cttgtgaaat ttgtttgtcc tatgctgctc    360
ttatgttaga tctgttaata cttaaagggc tatgccatat cctatcttaa gcgaagttta    420
aaccacgtag cctgatactt tgttaaagca tttgttttg tctgttatgc ttgcttcctt    480
gatataagct gacagttatc agtgcatcat tattagatta tttcttgtct gaatgatttg    540
tcccccacct attgtgttga ctcggatttg ttgcatttcg gtgattatgt agacgatttg    600
ttataaaagc atttgatcag ttgtttaaag agtagcatat tttatttgtc aactcttgag    660
ctggcagatt aatgatgaaa caattacccc aagcgcttta ttccactgat ttcagtgtga    720
tggaaagcta tgttatcata gcttttgtgg ttttcaatct gaaacatctg cagttcaagc    780
attacttaac ttttcagttt ttttcctttg atgttatgct agtattttt tgcttcttcc    840 tcttgtgtca aacaaaatta agtttattag aataatgttt ggaatctctt gggttcagta    900
atgagagaag tgatgagatc atatccacac gagatatctg cattcattat gatgatcact    960
atcatgcact accatctgat ctctcatcac tgttttaatt ttttgttttc attagaaact   1020
tttgattccc tagtttcttt gaatattgac cagtaaattt aaagggtatt catcttatgt   1080
ggtttgcaac accacatttc ctaataagtt ctctgttta aatgttcttg tgagtctgac   1140
attcatctca aagtttacta ggatagtagt cacacattgc tgttcaatct taatggggaa   1200
atgatgatac catatccaca cgagatatct gcagtcatta tgatgatcac atcatgcact   1260
accatctgat atccttgttt gtccatatta cttccattat tattttttta atacttgagt   1320
tgaaaagttt cattttttatg tgcaatctgt gatgcaacta ttcccattac atgaatcact   1380
gtgattatta tgaaaaaaat caccatcttt cggctgagat tgcacaacct aagttacatt   1440
ttcttaaatt acatactatt tgtttcttta cattttgcaa tcaatgccat ttggtatctg   1500
atgcacagtc ttttttggct gtgtgtctcg aaacgtggca aaaaactagg gggaacggat   1560
cttgcgacac tggtcactca tttatgagct tccagttact atatgcccgt ttacattaat   1620
actagtatta tgatatcttt ggtcagatct ttgcaatatg ttgttgtagt gttgactgca   1680
aaactgatgt gcatacattt gattagttag gttcagttat gtacacagtg atttatttgt   1740
atgcttatgt agcatttgaa atgttgcaat ctctgacaaa attgttctca tgcaggtgcc   1800
g                                                                  1801
```

<210> SEQ ID NO 72
<211> LENGTH: 1159
<212> TYPE: DNA
<213> ORGANISM: Setaria viridis

<400> SEQUENCE: 72

```
acttcggtga gtgccgtccg agtcttcttt gccttgctag ctccctcctc gatcggctcc     60
tcgcagatct tccccattcc tttgactact gtactgctac cttttttct agttcttgaa    120 cttggtaatc tgagggtgta cttggtaatc ttctactcgt ttagaactgc atgccgattc    180
tgattttact tgctgcagtt ttgtgcggct ttctgttgca tttgggcgct tattatgtct    240
atatattgtc tgtgttatgc tggcagtgtt attgttctca acccatgtcc atgtggttta    300
```

```
ttgctttggc aacttagatc tgtgcatggt tactggatat ctcgctctga ttaattctgc    360
atcgcaccat ggttagttga ctttactatt gttgtgcgta tgcttttgtg tggcaccatg    420
ttttttttc tgtaacagca atgtcttaca tgcgttcttt ttgctacacc actagtacta    480
ttcatccctt gactactgtt cggccatcaa tctgttttac cttgatgatg aacagagtat    540
tctttgaaag aagaaatacc tgcagctcag atgatgataa ctctggatta tgatctgatc    600
tccccctctg tacatctttt ttttgaccca aaaaaaggc ttcttctgtg gctatgagta    660
tggcaaataa caaggggca ctgatcgtct tgcggcactg cttgctccta aatgaacctt    720
ctgttactat atagccctag ctttcctagt tagtaagtaa ttcggtgtaa cctacctgct    780
tggcgcttta ttttgggct ctaggttgga acaaacgcgg ggcctaatat ttcgttaagg    840
tcagttttaa atgcaagatg attcttctaa gttctttaca attttttaa gaaagttttt    900
tcgtctgcgt gacagtgttt gctaaatgtt acctactgcc atttatagaa catcgttgca    960
tcctatagaa tataatgcac tcggattgca ggaagttatt attgcctgca ctcgagtaac   1020
attaagtaat ttgtcttgcc ctctattcaa gtttgggtga ttaatttgta ttggtgatgt   1080
tttatatttg ccccaagcac catttcttcg tgaaattagt actgcagtta ctgacgtcaa   1140
atacttgctg caggttccg                                                1159

<210> SEQ ID NO 73
<211> LENGTH: 899
<212> TYPE: DNA
<213> ORGANISM: Setaria italica

<400> SEQUENCE: 73
acttcggtac gtgctcgctg ctccgactcc tccagctttt gttggtgctg cgtttctgtg     60
aatgcttacg gcctctagga tacgtgactg gtttagttag atttagatta acctctgaaa    120
ttcgattcgt aaatctccgt gctgattata ccgtgttctc tagatagatg ctaacgtaat    180
aacagtagga atcaatgata gaaccttccc agaattatgt ttgtgataga acatacaatt    240
tgtttctaaa ataacagaga gagacataca atttagtgct taaatttaga ttcagaaatt    300
ttctgtaaaa tacattttgg gtgcttagtg gtatgtttaa catctgctaa ttttagattt    360
agagttctgt taaatttagc agcagggatt catagtccag gttaattgta tagtcgtttg    420
gtccgtcgag cttattttgt gacgaaatta gataaataaa caactccttg ctgtaatggt    480
ctcctgttat tgcttgaaga aataaataac tgagagcatt tcaacgcatt gctctgctcg    540
tttttttgttg tgaatttgtt tgttgcctga agaaataaat aattaagtga tggattgctc    600
tgctcattta ttgggacaac gtctattaag cagagcaact tgttgtaatt ttttgttgct    660
gtgctttgtc tgctgtcaat gaaacagggt taactgatag tctgacaggt tacatatgct    720
tgttgtgaca tgttgcaagc ctttagatct ctgtttgctg taattctgaa gttgaattga    780
gtggcactct gttctgtgta attccgaata agttgaattg attggaagag atctccttct    840
tcctgataat gaatactgtg aactcacaat cttgttcgtt ctttatattg caggtgcac     899

<210> SEQ ID NO 74
<211> LENGTH: 937
<212> TYPE: DNA
<213> ORGANISM: Setaria italica

<400> SEQUENCE: 74
ccgcaggtat tatcacaata atctcatacc attcctgtat gcatcatttt gtcatcatat     60
ttgcatctat gcagtcacca ttttcatgtt ttcttgtgga caataaattg ccaatcaatt    120
```

```
accacccaag aaaaaactgt agtattcagt gtgtaacatt aaaaacaaaa tgaattcagt      180
ggtagttatg agttgtgatt tggtgaaact atggatatga aatagtacca gtgacaaaaa      240
aaaacattcc catgttctta tcagttttat tagacgacaa aatctcaatt taaccaatat      300
gattaatcaa atatcttata gtaatttcat aagggaagtt tagatacgag tcatactttc      360
attctttata taagctactt atctatgttg cttttgtcga gtttctggaa gagctccaat      420
aaagtataaa tttcattgcc actacagttg agctaccttt gtcagtgagc agacctcttt      480
atttgttctt acagtaagat atagcttatc tacagaaaaa tatccttccg tggccgacat      540
tcacctatca ttgattggac caaaagtaat tttctcaaca gaacttcttg agagttacta      600
tattaagtat aagcctggat atcatgtgat cccatatata tctaaacaga gcaaagatgt      660
gagtgaatat cagtaagaat tttatgccct atcacagaga acagtcattc ttcttattgt      720
ctacataaag gttataggac aagatctaaa tctgtatact tgagtctagg gtgagtaaac      780
agacttcatt tgtattctca acagtactat ttatgtacct agctatagat gtagttgttt      840
cttctcagtc tgataacaaa agcttgcaaa ggaggtttac ctgttattgt aaagtacaag      900
tactctgtac tgaaaccatt tcttgttgca gatttca                              937

<210> SEQ ID NO 75
<211> LENGTH: 765
<212> TYPE: DNA
<213> ORGANISM: Setaria italica

<400> SEQUENCE: 75
cgcaaggtac agatccctgt ttcccgcctc agcctatttc gttagattca gtggattttg       60
gcgatgtccc cttacgagcg gtgtgctgag ctgtctagcc tttagtagac cgtaacgcga      120
gaagttgctg gtcgaatacc ttttgtgct ggttagtctg tggcatgtgc tgttgtggtg      180
gatatctggt caatcgtacc tattgtgtgt gcttatgcat tttcgtgcct tttaattgtg      240
gcgatagcag gtcctgtggc ggttcataga ttgcttcctg acccttagtt acgcagtact      300
gtgattacat aaattattca ttctctgaaa tgccagcttc tactgtgatg ttcttttgtc      360
cctgctctgc attgaagatc ttttagtaca ctattctaat atctagtacc aactgcttgc      420
atttgtgtga agttcctgta tatcatatta ttatgtcgag tttatattcc attgtatatt      480
ggttgcgaaa tgtgtaattg ccatctaact cctatggttt ctttcactgt actttgtttc      540
actttattat tgatgtaatt cacgtgctaa tttaggtgtt gactggtctt gttgtggaag      600
tctcttaatt atgaatcaaa gttattgctt taaatcccat ttgcattcct tcaatggccc      660
ttggaatgcc attctttaga ttttgtggca tcttgatggc ttgattgttg cagccaaatg      720
atggtgttta ctgtcttact ctttccctct tcattgcagg ttgtt                      765

<210> SEQ ID NO 76
<211> LENGTH: 1012
<212> TYPE: DNA
<213> ORGANISM: Setaria italica

<400> SEQUENCE: 76
cgcaaggtac ggtaccggtg catccccctc tcgcttgtta cgacccataa agaattaatg       60
gcaacacaaa tctcctattg tttgttgatt tagaggtgtc gcggacaaac tgctttgata      120
tctattttgt tttcccgtac tgatttgtgc gctctgaaac ttgcggttac ttgcggattc      180
agaggcgtcc caagtgtgag acggatccag tagattcacc cgcaagacga ctttgcagtg      240
```

```
tagtagaaag ctttgatctt tcgatgcgct ttgtatagtt tcagtcttgg tcatgatttg    300
tatctgaatt acgtgatctt tggggctgct taggcatctg cggctcccct gttgtggttc    360
tggatgtctt cctttgaatc tgtctagatt tttttttttg tttaatgatg aatggttcaa    420
ccacaaatta accctggctg tcaacaagat acctgtcttg accgtcaatg aatatgtttc    480
agttacatat ttgtaatact gcaaaaaaat ccagcaaggt tctttggaga aagcggagag    540
ttcatatctt ttttgcaaga atttaatgct ccttgcactg tttattctgc agttctgaac    600
gacatgttta gatctgcaat gctggttaaa ctaggactat ttccatgtag tttgtatggc    660
ttctacttgc caagggagtt cttttttatc acttttgctc ccagcacctt ccctccgtat    720
agttgctatc tgtagcaatg tccttcatgc atgaaatatt gtctgaattc attatctgtt    780
catgctggta tgagttgaca tgccattcaa tttgtgtcat cagtgtctgg attgatacat    840
gttttcatac tggaatactg gatttcaata tttcttacta ccctatgttt gcttgccaca    900
ccatattcct ttatagtttg tacatccggt ggccatattc tctctttaga tcttgcaatc    960
caacaagtct tgatctgaca ataattcctg tatactcttt ctttaggttg tg           1012

<210> SEQ ID NO 77
<211> LENGTH: 1152
<212> TYPE: DNA
<213> ORGANISM: Setaria italica

<400> SEQUENCE: 77
cgggaggtta gggttcccga tttatccagc tttcttttt gattgagaaa ttaatcttgc      60
gtgctgtcaa gagtgctgtc ctgcttgatc tagttgcgtg ttgcgtgttc gtggtacggg    120
agatacggga gtgcggcggg agtgcggcga gttttctccg ccttttttct tcttctgttt    180
tttttcgggt ggcgttctgc gatgcggcta gatccgcttt gtctcgggtg ctggtccgtg    240
ggtttgttag agctcgatcc acgagatctg aggcttggag cgcacggggg gcgtagatcc    300
gcctgatttg ggaatagttt gatgcgagga ctgaatgctg atcacctccc gggtttccgt    360 tcccatttg gggttagcaa ccgtgcctgt tatctgttgg aggcttggag cggggacacg    420
gatggttgaa tgtagaattt ctggagtgaa gtagcttgtt cagatatttg atctggatgt    480
acacgtgcct tcacggttag tagtgtatta aagggtagct ctatctgttg ctgctaggtg    540
ttggatgtga tttctcgatt tatgtactgt tcggtgtgtc ggattttggg tcatgtttca    600
cctgtttaag gaattatggt tgggtaacct gttgatctgg ggttttgaat gatgatgaat    660
tgctgttgaa ttaaataatt cattaatgat aaccttgtca aggatagatc cggttggtcc    720
ttttcagtga tctgtttggc agtagtttaa ataggttagt tctgtctgat tgcttaatt    780 gatggatttg gggatcacaa cagaatgaac agatcatatt acctgcattg tgtgggtct    840 gttattgcga tttttgaacc tgaacgtggg tgctgtaagc tagtgttcga ttagatggtg    900
ctgcttggtg tggctgtatt gcttttttga gaatggtgtg gctttattgc tggttcaatc    960
aggtttgtat gacccttca tatttctcag aaatgttatt aataagcttg ctcttaccaa   1020
acatggaggg gcttaatggc ttaagtcgag tttagtggcc agccatgtac ctttaccatg   1080
tagtcatttt agttgatatc ttgtaccttt ttgaggcaat ggcttatcag ttccctttg    1140 ttgcaggaag tt                                                       1152

<210> SEQ ID NO 78
<211> LENGTH: 1237
<212> TYPE: DNA
<213> ORGANISM: Setaria italica
```

<400> SEQUENCE: 78

```
acccaggtga ctgacctcat cctctttccc ccaccctccg tctctggttg ctatagctaa      60
gttcatccat gcgatgtcct gctagctgat tagtatttct actagtggag ttcgagtcgt     120
tttggttcca ttcagtagtg cttgtgttga ttggattgaa tcggaggact cgaagtggtt     180
tgctgctcga atcgcaagtt tgttgggcta atctcgatgc aatttatgtc aattcgttgt     240
tttagtggtc cttggcagtt ctctctgtga caggtccgtc cgatctgtag agatgcggtg     300
gaatcctggt ttactcaaaa cggttctaga ttcctctgtt gttcccttaa ttttttgttta    360
cgttaggagc ctatgaagtg gatatgctcg gatcctttc tgaaactcat ctgtttactc     420
agatctgctg gcagctcaca gttccagggt agttacgttg atggtctagt tttggtagtt     480
tcatgttcta tttctgtcca tttttgtgat gttcagtatg ttaaaatact atctgtgctt    540
ctgaatatct tgttatatga attcattgga caaactatgc attccttttg gcatcttaaa    600
tattttcctg aaggttagaa tcgacttcga aatgtttgtc taaattaatc ttctggtgtt    660
tccctatgcc agtctgttaa tatgtctgta ttatagtgtt ttgtttgaag tggtaatgta    720
catggtgcac cctgcagttt ttcatgtcta atattggatc tccttgtttg ctgtatgtat    780
taaggattag tttcacttct aatagcttac tgctgatgct ttcttgtttg tgtaatatgc    840
tgtgtaatca tgttgaccct gaggtttgta agaattcctc ttatttgatt attgcatgga    900
ttagtgtcct gaaggatgtg gctccttttgt acaattaaga taattcactt tttttttttct  960
caactttat atgcttacta gcccattagg ttgtgtaaac attagagtgc tttagcctgg    1020
taaagatgag ttaagcattt taaataaatt tttggatttg gttgatatca tccttaacac   1080
ctgcatttaa acaatttgtc tcttttgatc ctgactatta cagtgggtgt tactttcttt   1140
agtcattctg tggtatcaaa gtttctggtg tagttgtgta attatggttt tggttggatt   1200
cttactagta ttttctacct ttaaacagca ggaagtc                            1237
```

<210> SEQ ID NO 79
<211> LENGTH: 1190
<212> TYPE: DNA
<213> ORGANISM: Setaria italica

<400> SEQUENCE: 79

```
acgctggtga gttccttcgc gcttccacct ctgggttttg ttcctgctgt ttcagaagtg     60
gctctgtggt tcatcgcgca tcggactgcc tgtgcggatc ctatggtggc cgcggctgtt    120
gggctgatgg ggttttgatg cttgaggatt catgccatgt agttagcttg atgtacgcgg    180
gtcacttggg tgtggaaact gtagatgcga acggggtgtg gtaggctgcc tagatcctcg    240
actctgcttt cggtcaggcg tgtcttcagt gaaacatcac cgatcccctg gttcgtttca    300
acttcaacag cacaaaaaac ttcggccttc agaaagtgca gcgataggtc atttgtccgc    360
ttcgcttctt tacaaccggg ggttaggggg gtgatgcctt agtgctaatg atgtgattca    420
gagtcgctga cctactagta gaatggttgg gtgtgcattt gtatagggcc tttgacccttt    480
gatccagggt gatcatgata ttttggtagg gtgtataacc gttttatgtg caactcaagt    540
agaataatgt atttgaacca ttggattcaa ttaggagcta atatctggtc atcccaaccc    600
aagtcatttt aagcttctgg tccttagttg taattgagtt gtaagttttg aggaaattgt    660
tgcacacata gcagtctctt tgggtgacc ttgaaaggaa aataagggtg ttttagagtg    720
tttatcatga tgcagctcag ctacagtgcg taggaggaat tgaagttgag aggtgaagca    780
```

| | |
|---|---|
| tgaattgtgg tttattttga taatttcgca gttaggcaat tcaaaacaag tactgtttgc | 840 |
| tattctagtc ccacctgcac attcctttac ctagttgtat ttctaaacca tcttgattgg | 900 |
| cttaatttgc atgataaatg ctcctatgtc ttgttgggaa acagagattt cactgaccat | 960 |
| ttccgagtat aaacacacaa tctgggcaat tggtgtcttt gcttgtgtat ttttccctac | 1020 |
| tatagtgaaa cacatctgtc aagtggataa tgtttatgtt ctggttcttc acttagataa | 1080 |
| tggtctagat gtcattactt ggcttgcatg tgtaccatta aattaacatt cacagaggac | 1140 |
| ttccaatttt taactctatg tctaatataa ttttcgttgc ataggtattg | 1190 |

<210> SEQ ID NO 80
<211> LENGTH: 906
<212> TYPE: DNA
<213> ORGANISM: Setaria italica

<400> SEQUENCE: 80

| | |
|---|---|
| acgctcgtga gttccttctc ccttcctcct ccgtgttttg ttcctgctgc ttcggtctgc | 60 |
| tttgtagttc atcacgcatc gcgagtgcct gtggggatct gtggggcgt atacatagtt | 120 |
| tggttgggcg atgcacggtg ctagtggtgc cattcatgtt gcttgttact agtagaacgg | 180 |
| ctggctgtgc atttgtaaaa ggtgtgatca tggtaatttt ggcgagggaa tttcttcgtg | 240 |
| gacaaccatt tgcgcacatc taagtcaatc atgtatttga gctgttggat tcgtttaaga | 300 |
| gaatattatt ccaacccaag tgattttaag gctccgatcc atagttctat ttgggttgta | 360 |
| agttgtaaga aacttgctgt acttgtagca gcgctctttt ggtcggtgaa ggaaaagcag | 420 |
| ggtgttttag ggtggttatt atcatgatgc agcgcagctg gcgataagta tagatgagga | 480 |
| attgaagttg ggtgatgaag catgaccatg ttgatgttta tttgataatt tagccattgt | 540 |
| atgggaactc atatctagta ctgtttgcta ttgtagttct ctccctgcac atgcctttac | 600 |
| ttagttgcat tgctaaaacc gtatttcttt gcttaatctg tatgaaaaag gctcctctat | 660 |
| cttgttggga aacagagatt tcattgaatg cttgagacta caaacactcg atctggacac | 720 |
| ttgtgtgttt gcttatgtat ttgtccctac tagtgaaaca cgtgttttgt ggtttatgta | 780 |
| tatgttctgt ttcttttcact tagataaggg tctagatgtc attgcttgtc tttgtactgt | 840 |
| ttgattacca tccaaagtat caacttgtaa cacaatatgt ctgtattttt tgttccatag | 900 |
| gtattc | 906 |

<210> SEQ ID NO 81
<211> LENGTH: 1201
<212> TYPE: DNA
<213> ORGANISM: Setaria italica

<400> SEQUENCE: 81

| | |
|---|---|
| cttcaggtga gcgcatcgag gtccccttct gtttatactc ctttaatgct gctgtttctt | 60 |
| gttgctgccg aggatgttta gatgtctagg ggctgggttg ggtggtaggg tgcagtgggg | 120 |
| ttcgccgatc gtcttgggtt ctggttggct atcaggggct ggatccgtag taggagtaag | 180 |
| ggccgcaatg ttgctgagac tttcttggtg acttgtgtgg atgcttcgat cttgtgtgtt | 240 |
| gaggtggact agtagtattg acagtatatc ccttggtaat tttgtgatat ggtattagtt | 300 |
| tgtgctaatg gatgcctggt tcttctgaat tgcaagtgaa ttccgcaggg ttccttgtgc | 360 |
| ttagaaatgg aatttgtgat cttagtgttc agacagagtc actttgcttc aagtcaccac | 420 |
| cgacgtatta gttttcaatt tttgagcaaa ttttgtgctt ctatagaata cggttacaaa | 480 |
| caattatagc cagatattac ttctttgact tcttaaattg ttaagaaaat tgttccaaga | 540 |

-continued

```
tcgaaaatct cctttccacg aatcatgtag atgggactct tttcccccca aaagagaaca      600
ggtcatgatt tttaatatat tggaaattga tgcgcattgt ctggatagct tcagctgctg      660
atgcctagcg gtccttctga tccgaaaatg ctaaattctt cagatcgtca gctgtgagga      720
atcatgaatt tggttcctgc aattgaccat gtgtttgact aaatccttca tggattggcg      780
aatgccttgc actattacac caagagtttg catgcactgg acagcctgat ttgtttgtat      840
acatgcaact gaaacctaac tactattaa taccagctgg aaagcgaacg gttttggtgt       900
tgtaagacta gctgttgctg tttacaacta ttttttttctt ttgtttgaat atagtccctg     960
ttacagttag aattgcttgt atagttgtat ttggcttcct gtttgataag tactctaaag     1020
gaatgtttag aggtattagg atcttttctct cagttaatag atttagtctg tcaagatgta    1080
actctagtct tctgttgata gtaggaagac caacttttttc tcttcttgct gaagtaactt    1140
tagcgcatat tggtctaagt cttggtaaat gctgttttca ttcttgaaca ttgcaggtca     1200
c                                                                    1201

<210> SEQ ID NO 82
<211> LENGTH: 1011
<212> TYPE: DNA
<213> ORGANISM: Setaria italica

<400> SEQUENCE: 82
aagcaggtct gcttctgctc cctctgcctc cctttactgt gcatggcatg tgaggtttca       60
ctgtatgaga taatgtgttc tagatttgca ttgttggaca cttggctgag cacataaatg      120
cttttatcac cttttttactt tgttgaagac aggatttcct ttgtttagta gaatatgata    180
tcaaggaaat aatttgtagc tgctgatata tgaagtcata gattcataga tgctaacctt     240
tcttttaaaa gacaatcaag gttgcaagga aaacacagca agtctgtgac atatatgctg     300
tcagagtctt ttatagccaa tcaccggctt ttgaatcata gtggtgtata ctgaagtaat     360
ttgcatggca tgacaaattt tgcaagacct gaactgtcgg aatactatta gcaaggttta    420
gtgctattag caaaaaagaa aaggcttagt gcatataatc tgtgctagtt tttgttcatg     480
cgtaatcacg gaaacggtac ctcttactat taagtgtaac aagttctagt agaggcactg    540
tttactttga agtggcaaca atgtttcata tctcctcatt ttatgtttca agttcgtgtt    600
cctgtttcat atttcaccca tttgtttatt gcaatttcca tttatattct tattctgtga    660
aatctaagat gcttaactgt ctttgctgtt ggttctccac tgaaattgac atgtcttgct    720
gcatacattt ctactttata ttactaaatt acaaccaaat ggtgaaaatt aacttagtta    780
tgctattaca aaactgttta ttactgacag atggtctaga atacataagg caccacatat    840
gcataaccag ctgttttctaa ttctaatttg tggaatttgc tatgtttgtc caaaactgag    900
acaatctcaa ttctcaacta cattgcatcg aagtacgctt gatgttatga tatttttact   960
tcacatttta tttgctggag ttgacttgga atttaatgtc tgtaggctgt c              1011
```